(12) United States Patent
Drnek et al.

(10) Patent No.: US 11,123,222 B2
(45) Date of Patent: Sep. 21, 2021

(54) METHODS AND DEVICES FOR APPLYING LOCALIZED THERMAL THERAPY

(71) Applicant: Neuraxis, LLC, Traverse City, MI (US)

(72) Inventors: Michael Drnek, Hampstead, NH (US); Dan Farley, Traverse City, MI (US); John Sullivan, Pelham, NH (US)

(73) Assignee: NEURAXIS, LLC, Sandown, NH (US)

( * ) Notice: Subject to any disclaimer, the term of this patent is extended or adjusted under 35 U.S.C. 154(b) by 159 days.

(21) Appl. No.: 16/414,312

(22) Filed: May 16, 2019

(65) Prior Publication Data

US 2019/0336333 A1    Nov. 7, 2019

Related U.S. Application Data

(63) Continuation of application No. 15/056,260, filed on Feb. 29, 2016, now abandoned, which is a
(Continued)

(51) Int. Cl.
*A61F 7/12* (2006.01)
*A61B 17/70* (2006.01)
(Continued)

(52) U.S. Cl.
CPC ............ *A61F 7/12* (2013.01); *A61B 17/7049* (2013.01); *A61B 17/7059* (2013.01);
(Continued)

(58) Field of Classification Search
CPC ........................................ A61B 17/7001–7046
See application file for complete search history.

(56) References Cited

U.S. PATENT DOCUMENTS 3,130,991 A    4/1964   Piragino
3,281,093 A   10/1966   Barber
(Continued)

FOREIGN PATENT DOCUMENTS

CN    203244447 U    10/2013
WO    2009/103758 A2    8/2009
WO    2011/162910 A1   12/2011

OTHER PUBLICATIONS

Hansebout et al., Local cooling for traumatic spinal cord injury: outcomes in 20 patients and review of the literature. J Neurosurg: Spine. Mar. 14, 2014, pp. 1-12.
(Continued)

*Primary Examiner* — Jan Christopher L Merene
(74) *Attorney, Agent, or Firm* — Hayes Soloway PC

(57) ABSTRACT

Methods and devices are disclosed herein that generally involve applying thermal therapy to tissue (e.g., localized cooling or heating of tissue), and in particular applying thermal therapy to the spinal canal, tissue disposed within the spinal canal, and/or nerve roots extending from the spinal canal. In some embodiments, tissue can be cooled or heated by implanting or positioning a thermal device in proximity to the targeted tissue. A number of exemplary thermal devices are disclosed, including bone anchors, inserts for use with bone anchors, K-wires, bone anchor extensions or towers, cross-connectors, spinous process plates, spinal rods, pedicle markers, bone taps, drill bits, bone plugs, bone plates, clamps, interbody or disc implants, thermal pads, and tubing loops. The thermal device can be left in place following surgery to facilitate application of post-surgical thermal therapy. In some embodiments, the thermal device can be removed post-surgery in a minimally- or non-invasive manner.

11 Claims, 43 Drawing Sheets

Related U.S. Application Data continuation of application No. 14/487,802, filed on Sep. 16, 2014, now Pat. No. 9,308,123.

(60) Provisional application No. 61/878,168, filed on Sep. 16, 2013, provisional application No. 61/878,166, filed on Sep. 16, 2013.

(51) Int. Cl.
 *A61F 7/00* (2006.01)
 *A61B 17/56* (2006.01)

(52) U.S. Cl.
 CPC ........ *A61F 7/123* (2013.01); *A61B 2017/564* (2013.01); *A61F 2007/0024* (2013.01); *A61F 2007/0054* (2013.01); *A61F 2007/0059* (2013.01); *A61F 2007/0096* (2013.01); *A61F 2007/126* (2013.01)

(56) References Cited

U.S. PATENT DOCUMENTS

| | | |
|---|---|---|
| 3,326,585 A | 6/1967 | Piecha et al. |
| 3,369,550 A | 2/1968 | Thomas |
| 4,183,689 A | 1/1980 | Wirges et al. |
| 4,217,677 A | 8/1980 | Sumikawa |
| 4,286,656 A | 9/1981 | Felder |
| 4,303,150 A | 12/1981 | Olsson |
| 4,619,261 A | 10/1986 | Guerriero |
| 4,745,922 A | 5/1988 | Taylor |
| 4,781,193 A | 11/1988 | Pagden |
| 4,784,126 A | 11/1988 | Hourahane |
| 4,958,953 A | 9/1990 | Charondiere |
| 5,108,390 A | 4/1992 | Potocky et al. |
| 5,196,015 A | 3/1993 | Neubardt |
| 5,201,842 A | 4/1993 | Elsner |
| 5,205,665 A | 4/1993 | Aronne |
| 5,415,624 A | 5/1995 | Williams |
| 5,433,739 A | 7/1995 | Sluijter et al. |
| 5,474,558 A | 12/1995 | Neubardt |
| 5,531,776 A | 7/1996 | Ward et al. |
| 5,549,559 A | 8/1996 | Eshel |
| 5,571,147 A | 11/1996 | Sluijter et al. |
| 5,616,143 A | 4/1997 | Schlapfer et al. |
| 5,653,692 A | 8/1997 | Masterson et al. |
| 5,693,099 A | 12/1997 | Harle |
| 5,837,003 A | 11/1998 | Ginsburg |
| 5,855,446 A | 1/1999 | Disborg |
| 5,855,588 A | 1/1999 | Young |
| 5,891,094 A | 4/1999 | Masterson et al. |
| 5,899,898 A | 5/1999 | Arless et al. |
| 5,921,979 A | 7/1999 | Kovac et al. |
| 6,083,148 A | 7/2000 | Williams |
| 6,238,427 B1 | 5/2001 | Matta |
| 6,343,644 B1 | 2/2002 | Huang et al. |
| 6,613,044 B2 | 9/2003 | Carl |
| 6,629,975 B1 | 10/2003 | Kilpela et al. |
| 6,635,076 B1 | 10/2003 | Ginsburg |
| 6,699,240 B2 | 3/2004 | Francischelli |
| 6,733,442 B1 | 5/2004 | Larnard |
| 6,749,605 B2 | 6/2004 | Ashley et al. |
| 6,796,985 B2 | 9/2004 | Bolger et al. |
| 6,818,011 B2 | 11/2004 | Dobak, III |
| 6,899,694 B2 | 5/2005 | Kadziauskas et al. |
| 6,918,910 B2 | 7/2005 | Smith et al. |
| 6,964,667 B2 | 11/2005 | Shaolian et al. |
| 7,044,946 B2 | 5/2006 | Nahon et al. |
| 7,083,588 B1 | 8/2006 | Shmulewitz et al. |
| 7,144,394 B2 | 12/2006 | Carl |
| 7,182,726 B2 | 2/2007 | Williams et al. |
| 7,220,951 B2 | 5/2007 | Truckai et al. |
| 7,241,297 B2 | 7/2007 | Shaolian et al. |
| 7,347,856 B2 | 3/2008 | Wittenberger et al. |
| 7,449,019 B2 | 11/2008 | Uchida et al. |
| 7,645,282 B2 | 1/2010 | Huxel et al. |
| 7,651,496 B2 | 1/2010 | Keegan et al. |
| 7,722,620 B2 | 5/2010 | Truckai et al. |
| 7,744,630 B2 | 6/2010 | Lancial |
| 7,753,054 B2 | 7/2010 | Okano et al. |
| 7,819,826 B2 | 10/2010 | Diederich et al. |
| 7,819,860 B2 | 10/2010 | Wittenberger et al. |
| 7,905,923 B2 | 3/2011 | Keith et al. |
| 7,963,716 B2 | 6/2011 | Yamasaki |
| 8,048,129 B2 | 11/2011 | Forton et al. |
| 8,070,782 B2 | 12/2011 | McKay |
| 8,211,149 B2 | 7/2012 | Justis |
| 8,241,330 B2 | 8/2012 | Lamborne et al. |
| 8,252,057 B2 | 8/2012 | Fox |
| 8,348,952 B2 | 1/2013 | Sanders et al. |
| 8,398,677 B2 | 3/2013 | Lafontaine et al. |
| 8,454,693 B2 | 6/2013 | Malandain et al. |
| 8,475,505 B2 | 7/2013 | Nebosky et al. |
| 8,491,636 B2 | 7/2013 | Abboud et al. |
| 8,523,930 B2 | 9/2013 | Saunders et al. |
| 8,626,300 B2 | 1/2014 | Demarais et al. |
| 8,641,609 B2 | 2/2014 | Hestad et al. |
| 8,690,907 B1 | 4/2014 | Janardhan et al. |
| 8,715,314 B1 | 5/2014 | Janardhan et al. |
| 8,721,642 B1 | 5/2014 | Sullivan |
| 8,801,757 B2 | 8/2014 | Abdou |
| 8,911,486 B1 | 12/2014 | Drnek et al. |
| 9,358,056 B2 | 6/2016 | Stalcup et al. |
| 9,433,775 B2 | 9/2016 | Boyden et al. |
| 9,561,354 B2 | 2/2017 | Nebosky et al. |
| 9,616,205 B2 | 4/2017 | Nebosky et al. |
| 2001/0004710 A1 | 6/2001 | Felt et al. |
| 2002/0068975 A1 | 6/2002 | Teitelbaum et al. |
| 2002/0095144 A1 | 7/2002 | Carl |
| 2002/0198526 A1 | 12/2002 | Shaolian et al. |
| 2003/0014016 A1 | 1/2003 | Purdy |
| 2003/0018331 A1 | 1/2003 | Dycus et al. |
| 2003/0055427 A1 | 3/2003 | Graf |
| 2003/0130577 A1 | 7/2003 | Purdy et al. |
| 2003/0216721 A1 | 11/2003 | Diederich et al. |
| 2004/0034399 A1 | 2/2004 | Ginsburg |
| 2004/0039430 A1 | 2/2004 | Gonzales |
| 2004/0102825 A1 | 5/2004 | Daoud |
| 2004/0210226 A1 | 10/2004 | Trieu |
| 2004/0210286 A1 | 10/2004 | Saadat |
| 2005/0065584 A1 | 3/2005 | Schiff et al. |
| 2005/0090901 A1 | 4/2005 | Studer |
| 2005/0149007 A1 | 7/2005 | Carl |
| 2005/0251259 A1 | 11/2005 | Suddaby |
| 2006/0015160 A1 | 1/2006 | Larnard |
| 2006/0064093 A1 | 3/2006 | Thramann et al. |
| 2006/0084983 A1 | 4/2006 | Kim |
| 2006/0241576 A1 | 10/2006 | Diederich et al. |
| 2006/0241768 A1 | 10/2006 | Trieu |
| 2006/0247776 A1 | 11/2006 | Kim |
| 2006/0247780 A1 | 11/2006 | Bert |
| 2006/0271046 A1 | 11/2006 | Kwak et al. |
| 2007/0050002 A1 | 3/2007 | Elefteriades |
| 2007/0112428 A1 | 5/2007 | Lancial |
| 2007/0162007 A1 | 7/2007 | Shoham |
| 2007/0191831 A1 | 8/2007 | Sanders et al. |
| 2007/0198050 A1 | 8/2007 | Ravenscroft et al. |
| 2007/0203579 A1 | 8/2007 | Vittur et al. |
| 2007/0225781 A1 | 9/2007 | Saadat et al. |
| 2007/0233148 A1 | 10/2007 | Truckai et al. |
| 2007/0233226 A1 | 10/2007 | Kochamba et al. |
| 2007/0233249 A1 | 10/2007 | Shadduck |
| 2007/0260232 A1 | 11/2007 | Carl |
| 2007/0260250 A1 | 11/2007 | Wisnewski et al. |
| 2007/0282447 A1 | 12/2007 | Yedlicka et al. |
| 2008/0065062 A1 | 3/2008 | Leung et al. |
| 2008/0065083 A1 | 3/2008 | Truckai et al. |
| 2008/0154307 A1 | 6/2008 | Colleran et al. |
| 2008/0154373 A1 | 6/2008 | Protopsaltis et al. |
| 2008/0183211 A1 | 7/2008 | Lamborne et al. |
| 2008/0208256 A1 | 8/2008 | Thramann |
| 2008/0215151 A1 | 9/2008 | Kohm et al. |
| 2008/0249532 A1 | 10/2008 | Schoutens et al. |
| 2008/0269761 A1 | 10/2008 | Truckai et al. |
| 2008/0294222 A1 | 11/2008 | Schechter |

(56) References Cited

U.S. PATENT DOCUMENTS

| | | |
|---|---|---|
| 2008/0300687 A1 | 12/2008 | Lin et al. |
| 2009/0012618 A1 | 1/2009 | Ahrens et al. |
| 2009/0036893 A1 | 2/2009 | Kartalian et al. |
| 2009/0112262 A1 | 4/2009 | Pool et al. |
| 2009/0222093 A1 | 9/2009 | Liu et al. |
| 2009/0299327 A1 | 12/2009 | Tilson et al. |
| 2010/0274286 A1 | 10/2010 | Blain et al. |
| 2010/0312318 A1 | 12/2010 | D'Ambrosio et al. |
| 2010/0322702 A1 | 12/2010 | Yrjo |
| 2011/0004248 A1 | 1/2011 | Abdou |
| 2011/0034975 A1 | 2/2011 | Ferree |
| 2011/0040384 A1 | 2/2011 | Junn et al. |
| 2011/0066216 A1 | 3/2011 | Ting et al. |
| 2011/0071569 A1 | 3/2011 | Black |
| 2011/0077687 A1 | 3/2011 | Thompson et al. |
| 2011/0144753 A1 | 6/2011 | Marchek et al. |
| 2011/0282418 A1 | 11/2011 | Saunders et al. |
| 2011/0319946 A1 | 12/2011 | Levy et al. |
| 2012/0035659 A1 | 2/2012 | Barrus et al. |
| 2012/0065733 A1 | 3/2012 | Wieder |
| 2012/0101485 A1 | 4/2012 | Wittenberger |
| 2012/0109304 A1 | 5/2012 | Balckwell et al. |
| 2012/0197311 A1 | 8/2012 | Kirschman |
| 2012/0221059 A1 | 8/2012 | Mollman et al. |
| 2012/0226316 A1 | 9/2012 | Dant et al. |
| 2012/0288848 A1 | 11/2012 | Latham et al. |
| 2012/0289896 A1 | 11/2012 | Wolfe et al. |
| 2013/0006307 A1 | 1/2013 | Robinson et al. |
| 2013/0039899 A1 | 2/2013 | Preiss-Bloom et al. |
| 2013/0096614 A1 | 4/2013 | Zhang |
| 2013/0165976 A1 | 6/2013 | Gunn |
| 2013/0172934 A1 | 7/2013 | Walker et al. |
| 2013/0261507 A1 | 10/2013 | Diederich et al. |
| 2013/0281995 A1 | 10/2013 | Saunders et al. |
| 2013/0305516 A1 | 11/2013 | Overton et al. |
| 2013/0338712 A1 | 12/2013 | Massenzio et al. |
| 2014/0135928 A1 | 5/2014 | Sweeney et al. |
| 2014/0316468 A1 | 10/2014 | Keiser et al. |
| 2014/0336706 A1 | 11/2014 | Garamszegi |
| 2015/0057707 A1 | 2/2015 | Barrus et al. |
| 2015/0080952 A1 | 3/2015 | Drnek et al. |
| 2015/0080992 A1 | 3/2015 | Drnek et al. |
| 2015/0250513 A1 | 9/2015 | De Lavigne Sainte Suzanne |

OTHER PUBLICATIONS

Invitation to Pay Additional Fees in International Application No. PCT/US2014/37825, dated Sep. 30, 2014 (3 pages).

International Search Report and Written Opinion for PCT/US2014/37825, dated Dec. 11, 2014 (20 pages).

Invitation to Pay Additional Fees in International Application No. PCT/US2014/55872, dated Jan. 7, 2015 (2 pages).

International Search Report and Written Opinion for PCT/US2014/55872, dated Mar. 5, 2015 (16 pages).

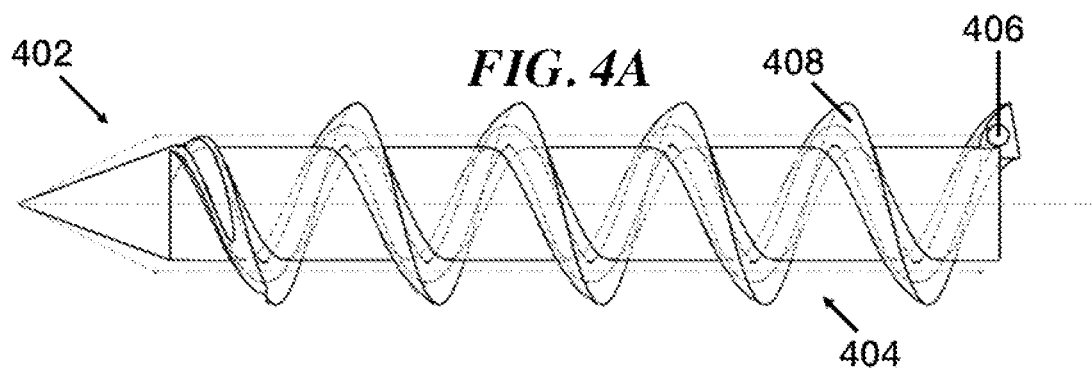
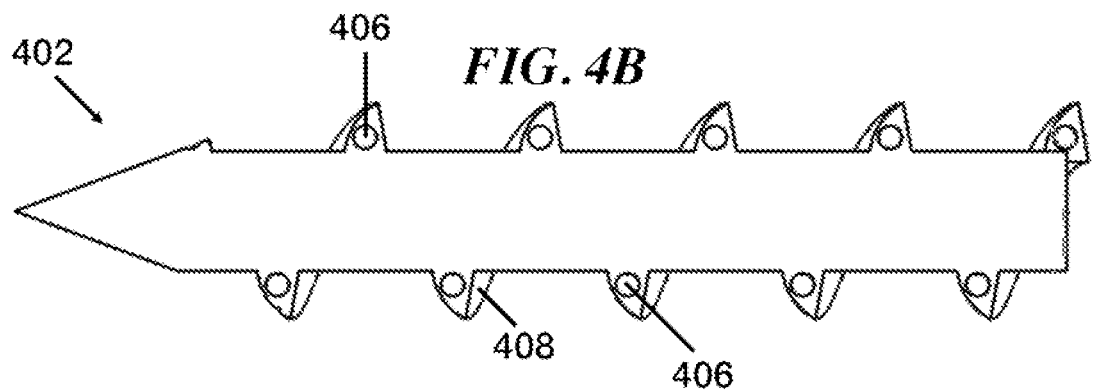
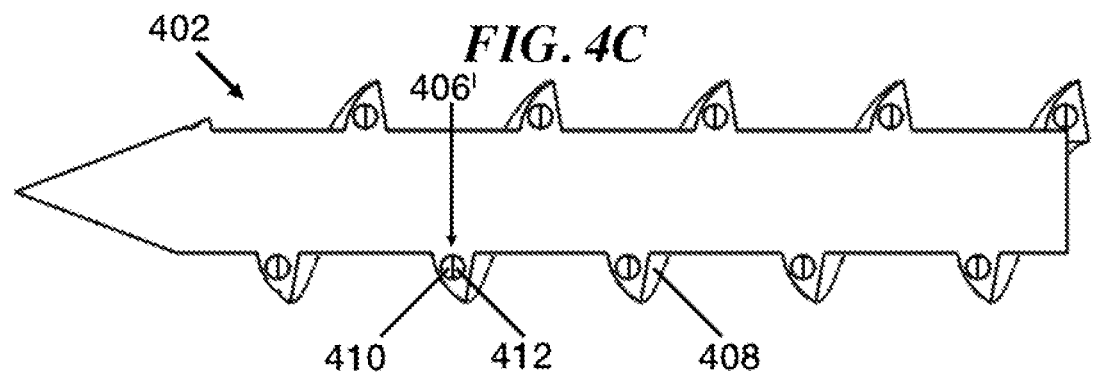
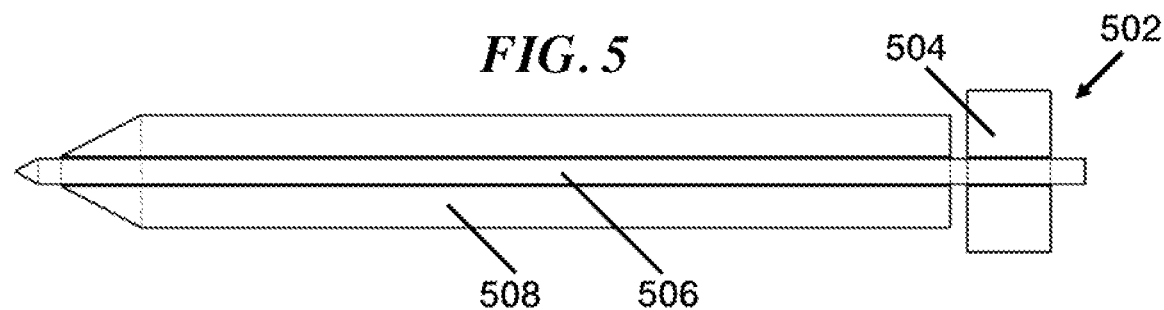

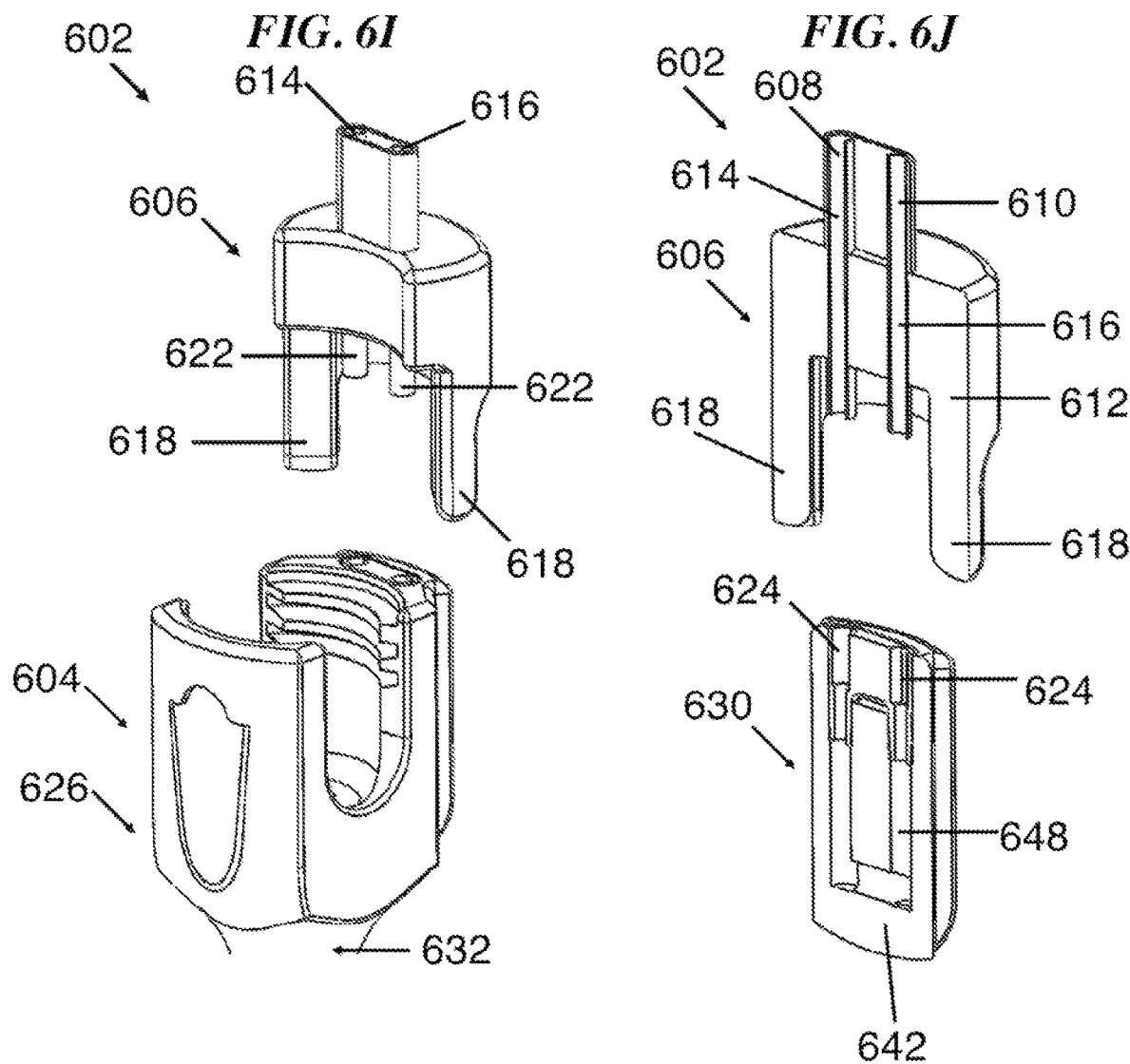

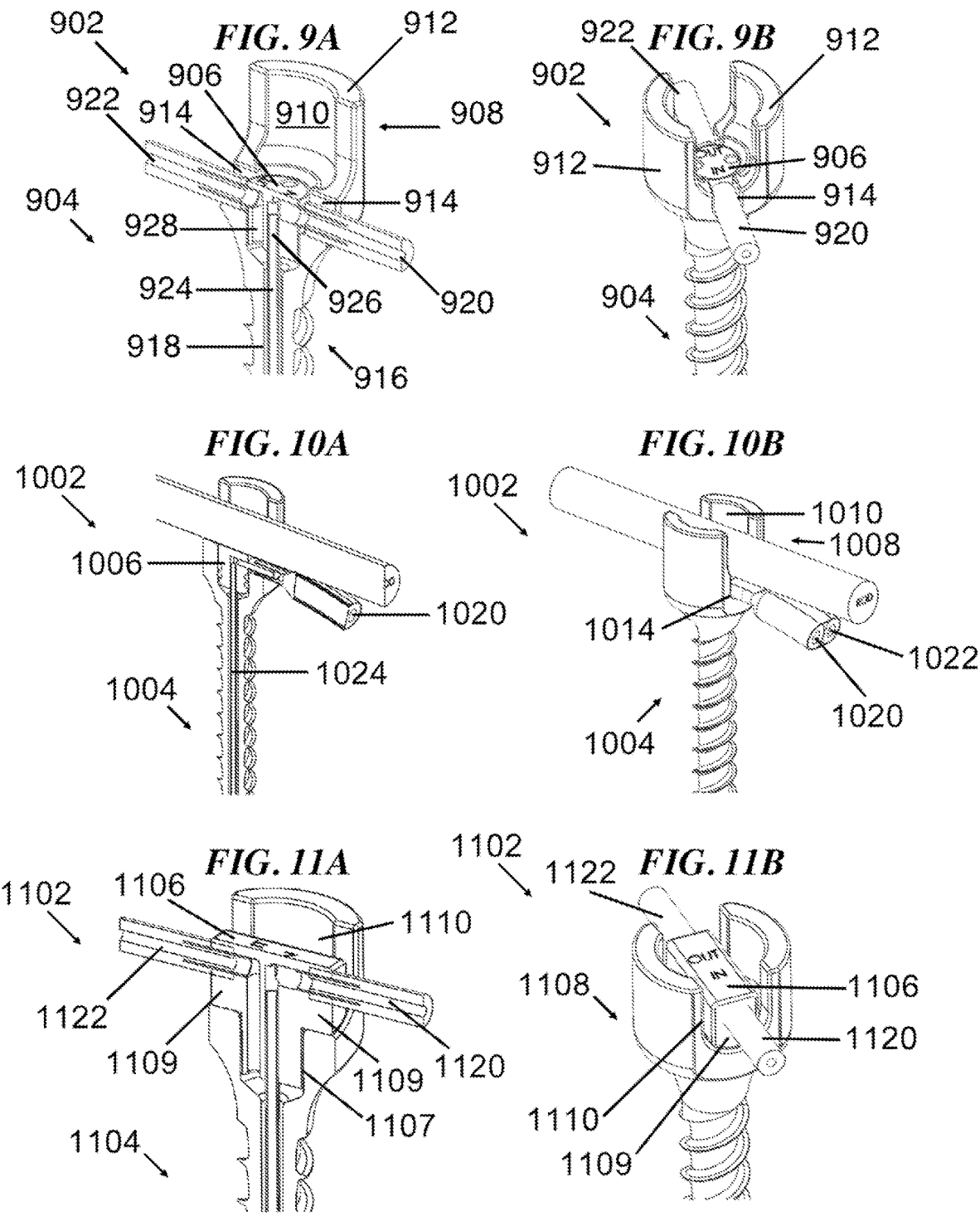

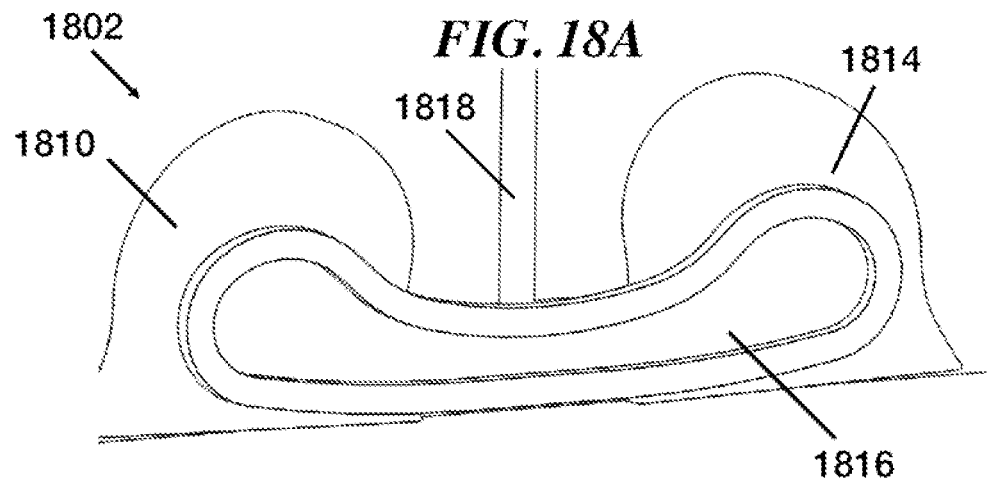
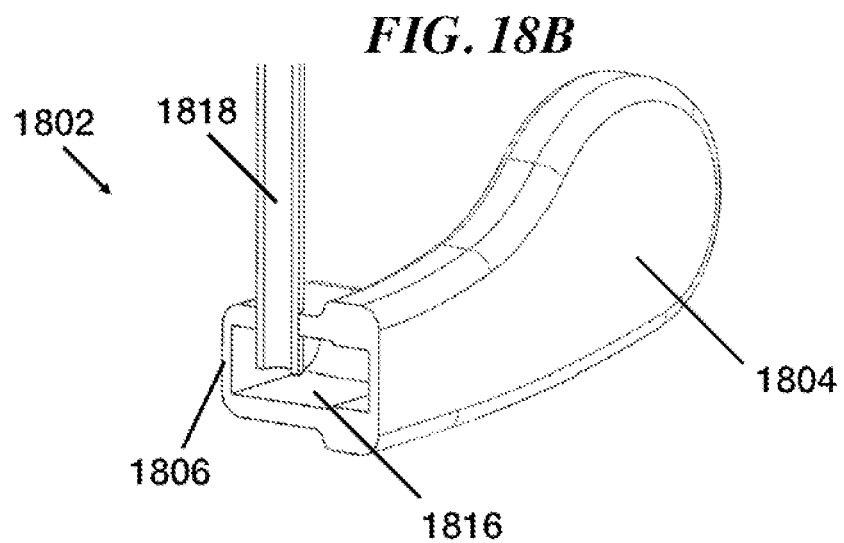
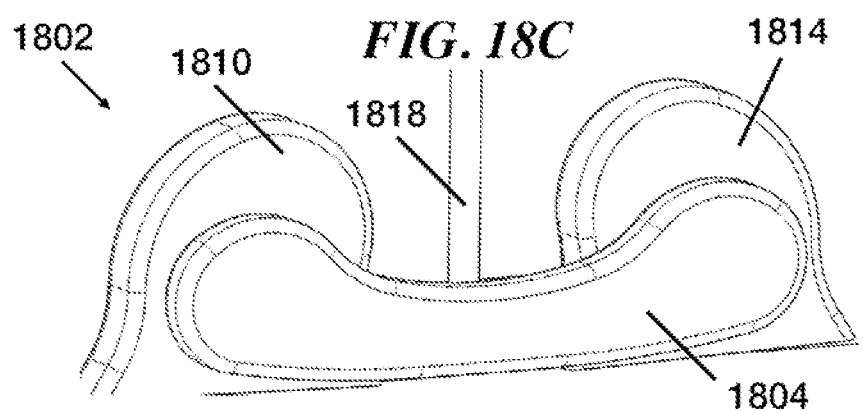

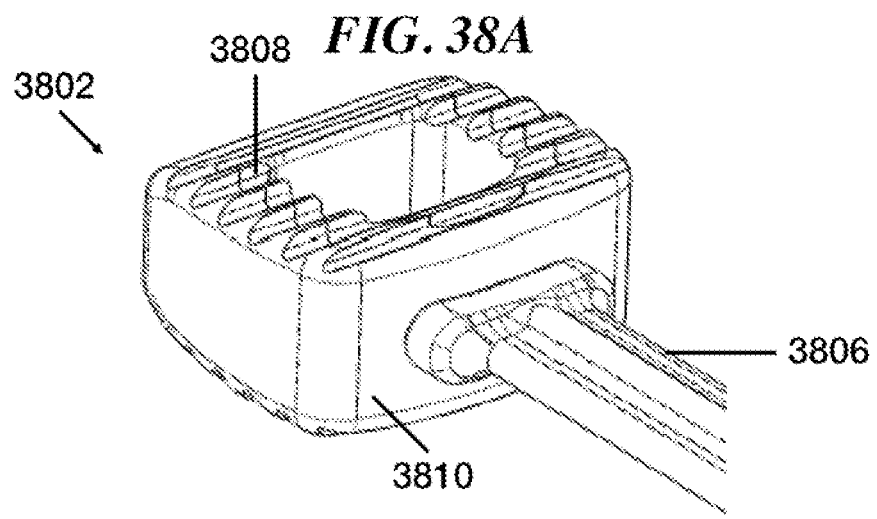
*FIG. 38A*
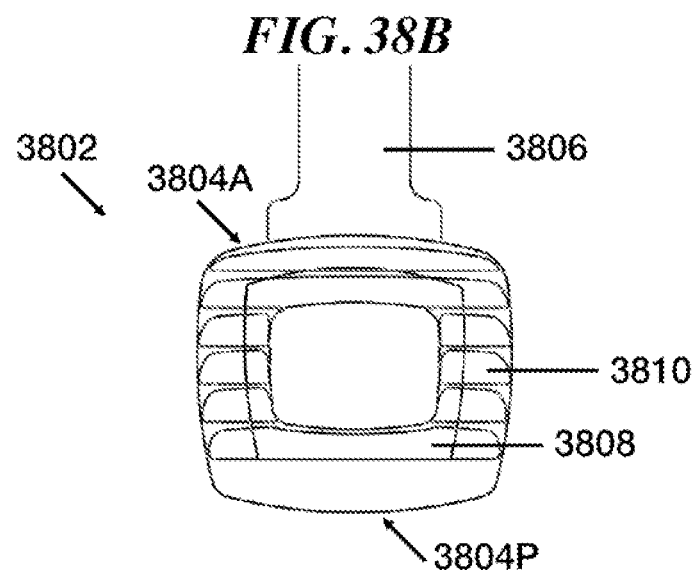
*FIG. 38B*
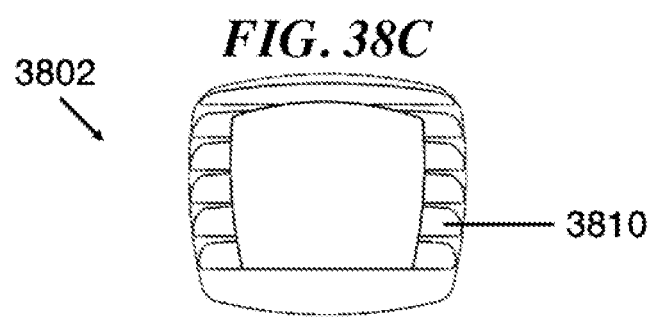
*FIG. 38C*
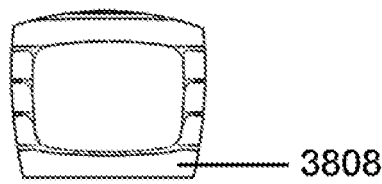

METHODS AND DEVICES FOR APPLYING LOCALIZED THERMAL THERAPY

This application is a continuation of U.S. patent application Ser. No. 15/056,260, filed Feb. 29, 2016, now abandoned, which was a continuation of U.S. patent application Ser. No. 14/487,802, now U.S. Pat. No. 9,308,123, filed Sep. 16, 2014, which claims the benefit of U.S. Provisional Application No. 61/878,166, filed Sep. 16, 2013 and U.S. Provisional Application No. 61/878,168, filed Sep. 16, 2013, each of which is hereby incorporated by reference herein in its entirety.

FIELD

Methods and devices for applying localized thermal therapy are disclosed herein.

BACKGROUND

According to the National Spinal Cord Injury Statistical Center, there are more than 259,000 people living with a spinal cord injury in the United States. Traumatic spinal cord injury afflicts around 15,000 people in the United States each year. Approximately 12,000 survive the cord injury with a neurological deficit, which is commonly a severe, disabling physical impairment and mental burden. Long-term care for cord injuries costs an estimated $9.7 billion annually in the United States.

Application of certain degrees of hypothermia to a patient's spine and spinal cord after a spinal cord injury can lead to benefits, such as a reduction of the metabolic demand of spinal cord cells, reduction of edema, added tolerance to hypoxia/ischemia, and ultimately a reduction in spinal cord tissue damage or cell death. Realizing these benefits could mean the difference between quadriplegia and being able to use one's arms. The use of a cooling effect for these purposes can be referred to as therapeutic hypothermia.

Besides traumatic spinal cord injury, the spinal cord can be injured due to surgical procedures such as abdominal aneurysm repair, wherein blood flow to the spinal cord is reduced. This lack of blood flow, also known as ischemia, can cause cellular damage to the spinal cord. Local cooling of the spinal cord can decrease the incidence of spinal cord injury in abdominal aneurysm surgery. Nerve roots or any member of the central nervous system in the spine can also become damaged from trauma and/or surgical insult, and can cause neurologic deficits and/or significant patient pain. It will be appreciated that the spinal cord and nerves can become injured through any number of means.

Existing methods for cooling the spine involve systemic cooling of the entire body. Such treatments carry a number of disadvantages. For one thing, systemic cooling techniques lack the ability to specifically target the injured tissue and, as a result, other unrelated tissue can be damaged or destroyed by the cooling. Systemic cooling can also cause a wide variety of side effects. In addition, the degree to which the body can be cooled systemically is very limited, and it is difficult to precisely control the degree to which the body is cooled in systemic approaches. Body temperature changes using systemic techniques also tend to occur very slowly, which can undesirably delay administration of a cooling effect to the injured tissue.

In some instances it can be desirable to apply localized heating or therapeutic hyperthermia to a patient.

There is a continual need for improved methods and devices for applying thermal therapy.

SUMMARY

Methods and devices are disclosed herein that generally involve applying thermal therapy to tissue (e.g., localized cooling or heating of tissue), and in particular applying thermal therapy to the spinal canal, tissue disposed within the spinal canal, and/or nerve roots extending from the spinal canal. In some embodiments, tissue can be cooled or heated by implanting or positioning a thermal device in proximity to the targeted tissue. A number of exemplary thermal devices are disclosed, including bone anchors, inserts for use with bone anchors, K-wires, bone anchor extensions or towers, cross-connectors, spinous process plates, spinal rods, pedicle markers, bone taps, drill bits, bone plugs, bone plates, clamps, interbody or disc implants, thermal pads, and tubing loops. The thermal device can be left in place following surgery to facilitate application of post-surgical thermal therapy. In some embodiments, the thermal device can be removed post-surgery in a minimally- or non-invasive manner.

In some embodiments, a thermal device includes a connector configured to couple a first spinal fixation rod to a second spinal fixation rod, the connector having a first recess formed therein configured to receive a first spinal fixation rod and a second recess formed therein configured to receive a second spinal fixation rod; a delivery conduit extending from the connector and being configured to supply a thermal medium to a chamber formed in the connector; and an exhaust conduit extending from the connector and being configured to withdraw the thermal medium from the chamber. The chamber can be or can include an inflatable member configured to expand outward from the connector when inflated with the thermal medium. The inflatable member can be configured to protrude through a window formed in a sidewall of the connector when inflated with the thermal medium. At least one of the delivery and exhaust conduits can be attached to the inflatable member such that removing said at least one of the delivery and exhaust conduits from the thermal device is effective to remove the inflatable member from the thermal device. A lower surface of the connector can be concave and configured to receive at least a portion of a patient's dura therein. The delivery and exhaust conduits can be selectively detachable from the connector. The delivery and exhaust conduits can be formed by inner lumens of a multi-lumen conduit.

In some embodiments, a method of applying localized thermal therapy includes coupling a connector to a first spinal fixation rod and to a second spinal fixation rod secured to a spine of a patient such that a cavity formed in the connector is disposed adjacent to a spinal canal of the patient; and delivering a thermal medium to the cavity to apply a thermal effect to the spinal canal of the patient. Delivering the thermal medium can include supplying a heated or cooled fluid to the cavity to expand an inflatable member of the connector into contact with or into close proximity to the spinal canal. The first rod can be disposed on a first side of a midline of the patient's spine and the second rod can be disposed on a second, opposite side of the midline of the patient's spine. The method can include positioning the connector such that at least a portion of the patient's spinal cord is received within a concave recess formed in a lower surface of the connector. Delivering the thermal medium can include supplying a heated or cooled fluid to the cavity through a delivery conduit coupled to the connector and in fluid communication with the cavity. The method can include closing an incision around the delivery conduit such that the delivery conduit extends out of the patient while the connector remains implanted in the patient. The thermal medium can be delivered after closing the incision. The method can include decoupling the delivery conduit from the connector after closing the incision and pulling the delivery conduit through the closed incision to remove the delivery conduit from the patient. Removing the delivery conduit can include removing an inflatable member attached to the delivery conduit.

In some embodiments, a thermal device includes a bone anchor having a proximal head and a distal shank, the proximal head having first and second opposed arms that define a rod-receiving recess therebetween; a fluid inlet pathway that extends through at least one of the first and second arms; a fluid outlet pathway in fluid communication with the fluid inlet pathway and that extends through at least one of the first and second arms; a delivery conduit configured to be selectively coupled to the proximal head and to supply a thermal medium to the fluid inlet pathway; and an exhaust conduit configured to be selectively coupled to the proximal head and to withdraw the thermal medium from the fluid outlet pathway. The fluid inlet pathway can extend through the first arm, through a base of the proximal head, through a plug disposed in a cannulation of bone anchor, and through a tube that extends distally from the plug within the cannulation of the bone anchor. The fluid outlet pathway can extend through a cannulation of the bone anchor, through a plug disposed in the cannulation, through a base of the proximal head, and through the first arm. The fluid inlet pathway and the fluid outlet pathway can extend only through one of the first and second arms. The distal shank can be polyaxially movable with respect to the proximal head. The fluid inlet pathway can extend through the first arm, through a base of the proximal head, through a plug disposed in a cannulation of bone anchor, and through a tube that extends distally from the plug within the cannulation of the bone anchor. The fluid outlet pathway can extend through the cannulation of the bone anchor, through the plug disposed in the cannulation, through the base of the proximal head, and through the second arm. The device can include a connector from which the delivery and exhaust conduits extend, the connector being configured to be selectively coupled to at least one of the first and second arms to place the delivery and exhaust conduits in fluid communication with the fluid inlet and outlet pathways, respectively. The connector can include one or more mating features configured to align the connector with at least one of the first and second arms and to couple the connector to said at least one arm. The connector can be configured to mate with a proximal-facing surface of at least one of the first and second arms. The connector can include an elongate sleeve through which the fluid delivery and exhaust conduits extend. The device can include a plug disposed in the bone anchor through which the fluid inlet and fluid outlet pathways extend, the plug being disposed distal to a driving interface of the bone anchor.

In some embodiments, a thermal device includes a bone anchor having a proximal head and a distal shank, the proximal head having first and second opposed arms that define a rod-receiving recess therebetween; at least one cut-out formed in the proximal head beneath the rod-receiving recess; a plug disposed within the bone anchor beneath the rod-receiving recess; a fluid inlet pathway that extends through the plug; a fluid outlet pathway in fluid communication with the fluid inlet pathway and that extends through the plug; a delivery conduit extending laterally-outward from the plug through the at least one cut-out, the delivery conduit being configured to supply a thermal medium to the fluid inlet pathway; and an exhaust conduit extending laterally-outward from the plug through the at least one cut-out, the exhaust conduit being configured to withdraw the thermal medium from the fluid outlet pathway. The at least one cut-out can include only a single cut-out through which the delivery and exhaust conduits extend. The at least one cut-out can include first and second opposed cut-outs, the delivery conduit extending through the first cut-out and the exhaust conduit extending through the second cut-out.

In some embodiments, a thermal device includes a plug having a distal projection and first and second lateral extensions, the plug being configured to be received within a head portion of a bone anchor such that a fluid-tight seal is formed between the distal projection and a cannulation of the bone anchor and such that the first and second lateral extensions are seated within a rod-receiving recess of the bone anchor; a delivery conduit extending from the plug, the delivery conduit being configured to supply a thermal medium to a fluid inlet pathway formed in the plug; and an exhaust conduit extending from the plug, the exhaust conduit being configured to withdraw the thermal medium from a fluid outlet pathway formed in the plug.

In some embodiments, a method of applying localized thermal therapy includes implanting a bone anchor a bone structure of a patient; attaching a connector having fluid delivery and exhaust conduits coupled thereto to the bone anchor to place the fluid delivery and exhaust conduits in fluid communication with fluid inlet and outlet pathways formed in the bone anchor, respectively; and circulating a cooled or heated fluid through the bone anchor via the delivery and exhaust conduits to applying a thermal effect to the bone anchor, the bone structure of the patient, and tissue adjacent to said bone structure. Attaching the connector can include attaching the connector to a head portion of the bone anchor such that a distal-facing surface of the connector abuts a proximal facing surface of the head portion of the bone anchor. The method can include seating a spinal fixation element in a rod-receiving recess defined in a head portion of the bone anchor prior to attaching the connector. The circulating can include circulating the fluid only through a proximal head portion of the bone anchor. Attaching the connector can include seating the connector in a recess formed in the bone anchor such that the delivery and exhaust conduits extend through at least one cut-out formed in the bone anchor beneath a rod-receiving recess defined in the bone anchor. The method can include seating a spinal fixation element in the rod-receiving recess after attaching the connector. Attaching the connector can include seating the connector such that a distal projection of the connector forms a seal with a cannulation of the bone anchor and such that first and second lateral extensions of the connector are seated within a rod-receiving recess of the bone anchor. The method can include closing a skin incision through which the bone anchor is implanted in the patient such that the delivery and exhaust conduits extend through the incision and circulating the fluid after closing the skin incision. The method can include detaching the connector from the bone anchor and removing the connector from the patient after closing the incision without re-opening the incision. The method can include using the connector to manipulate the position of the bone structure prior to, during, or after circulating the fluid. The method can include delivering an implant through the connector prior to, during, or after circulating the fluid. The implant can be or can include a fixation rod and the method can further include coupling the fixation rod to the bone anchor to which the connector is attached.

In some embodiments, a thermal device includes a cylindrical insert sized and configured for placement into a cannulation of a bone anchor, the insert including first and second concentric tubes, an interior of the first tube defining an inner chamber and a space between the first and second tubes defining an outer chamber, the inner and outer chambers being in fluid communication with one another at a distal end of the first tube; a delivery conduit coupled to the insert and in fluid communication with the inner chamber, the delivery conduit being configured to supply a thermal medium to the inner chamber; and an exhaust conduit coupled to the insert and in fluid communication with the outer chamber, the exhaust conduit being configured to withdraw the thermal medium from the outer chamber.

In some embodiments, a thermal device includes a bone anchor having a cannulation formed therein; a cylindrical insert sized and configured for placement into the cannulation of the bone screw, the insert including a first tube having an open distal end, an interior of the first tube defining an inner chamber and a space between the first tube and the cannulation of the bone anchor defining an outer chamber, the inner and outer chambers being in fluid communication with one another at a distal end of the first tube; a delivery conduit coupled to the insert and in fluid communication with the inner chamber, the delivery conduit being configured to supply a thermal medium to the inner chamber; and an exhaust conduit coupled to the insert and in fluid communication with the cannulation of the bone anchor, the exhaust conduit being configured to withdraw the thermal medium from the outer chamber. The device can include a cap disposed in the cannulation of the bone anchor to seal a distal end of the cannulation. The cannulation can extend only partially through the bone anchor such that a distal end of the bone anchor is closed.

In some embodiments, a thermal device includes a bone anchor having a proximal head, a distal shank, and a thread formed on at least a portion of the distal shank; a fluid chamber defined within the thread; a delivery conduit coupled to the device and in fluid communication with the chamber, the delivery conduit being configured to supply a thermal medium to the chamber; and an exhaust conduit coupled to the device and in fluid communication with the chamber, the exhaust conduit being configured to withdraw the thermal medium from the chamber. The chamber can be defined only within the thread and can not extend into the distal shank.

In some embodiments, a method of applying localized thermal therapy includes positioning a distal end of a guide wire in a bone structure of a patient; advancing a cannulated bone anchor over the guide wire such that the guide wire extends through the cannulation of the bone anchor; implanting the bone anchor in the bone structure; and applying a thermal effect to a proximal end of the guide wire to heat or cool the guide wire, the bone anchor, the bone structure of the patient, and tissue adjacent to said bone structure.

In some embodiments, a method of applying localized thermal therapy, includes implanting a bone anchor in a bone structure of a patient; inserting a solid thermally-conductive member into a cannulation of the bone anchor; and applying a thermal effect to a proximal end of the thermally-conductive member to heat or cool the thermally-conductive member, the bone anchor, the bone structure of the patient, and tissue adjacent to said bone structure.

In some embodiments, a thermal device includes a first plate having a superior wing portion and an inferior wing portion, the first plate being configured for placement against lateral sides of superior and inferior spinous processes; a bridge extending laterally from the first plate and defining a chamber therein; a delivery conduit extending from the bridge, the delivery conduit being configured to supply a thermal medium to the chamber; and an exhaust conduit extending from the bridge, the exhaust conduit being configured to withdraw the thermal medium from the chamber. The device can include a second plate from which the bridge extends laterally, the second plate having a superior wing portion and an inferior wing portion, the second plate being configured for placement against lateral sides of superior and inferior spinous processes such that said spinous processes are disposed between the first and second plates and such that the bridge is disposed between said spinous processes. The chamber can extend into at least one of the first and second plates. The chamber can extend into the superior and inferior wing portions of at least one of the first and second plates.

In some embodiments, a device includes a first plate having a superior wing portion and an inferior wing portion, the first plate being configured for placement against lateral sides of superior and inferior spinous processes; a bridge extending laterally from the first plate; and a second plate having a superior wing portion and an inferior wing portion, the second plate being configured for placement against lateral sides of superior and inferior spinous processes such that said spinous processes are disposed between the first and second plates and such that the bridge is disposed between said spinous processes; wherein the bridge is slidably received within an opening formed in the second plate such that a distance between the first and second plates can be adjusted by sliding the second plate along the bridge. The device can include at least one locking screw threadably mounted in the second plate such that the at least one locking screw can be advanced into engagement with the bridge to lock a position of the second plate relative to the bridge. The at least one locking screw can include first and second locking screws and a longitudinal axis of the first locking screw can extend at an oblique angle to a longitudinal axis of the second locking screw. The device can include a temperature sensor embedded in at least one of the first plate, the second plate, and the bridge. The temperature sensor can extend anteriorly from the bridge towards a spinal canal when the first plate is positioned against lateral sides of superior and inferior spinous processes. The temperature sensor can be or can include a flexible contact.

In some embodiments, a method of applying localized thermal therapy includes removing at least a portion of the cortical bone of a spinous process to form a decorticated portion of the spinous process; positioning a plate in contact with the decorticated portion of the spinous process; and applying a thermal effect to the plate to heat or cool the spinous process and a spinal canal adjacent thereto. The method can include measuring a temperature using a temperature sensor embedded in the plate.

In some embodiments, a method of applying localized thermal therapy includes forming an incision in a patient to access a spinous process of the patient; positioning a plate in contact with the decorticated portion of the spinous process, the plate having at least one conduit extending therefrom through which a thermal effect can be applied to the plate; closing the incision around the at least one conduit such that the at least one conduit extends out of the patient; and after closing the incision, applying a thermal effect to the plate to heat or cool the spinous process and a spinal canal adjacent thereto. The method can include decoupling the at least one conduit from the plate after closing the incision and removing the at least one conduit through the closed incision.

In some embodiments, a thermal device includes an elongate shield configured to be positioned over a midline of a patient's spinal canal, the shield including a superior flange having an opening formed therein through which a bone anchor can be received to couple the shield to a superior vertebra and an inferior flange having an opening formed therein through which a bone anchor can be received to couple the shield to an inferior vertebra; a delivery conduit extending from the shield, the delivery conduit being configured to supply a thermal medium to a chamber formed in the shield; and an exhaust conduit extending from the shield, the exhaust conduit being configured to withdraw the thermal medium from the chamber. The shield can have a width of at least about 15 mm.

In some embodiments, a method of protecting a spinal canal and applying localized thermal therapy includes positioning a plate over a spinal canal such that a longitudinal axis of the plate is substantially parallel to a longitudinal axis of the spinal canal; attaching a superior flange of the plate to a superior vertebra using at least one bone anchor; attaching an inferior flange of the plate to an inferior vertebra using at least one bone anchor; and applying a thermal effect to the plate to apply localized thermal therapy to the spinal canal. Positioning the plate can include positioning the plate over a midline of the spinal canal. Positioning the plate can include positioning the plate laterally offset from a midline of the spinal canal on a first side of the spinal canal and positioning a second plate laterally offset from the midline of the spinal canal on a second, opposite side of the spinal canal.

In some embodiments, a method of applying localized thermal therapy includes implanting a first bone anchor in a first vertebra; implanting a second bone anchor in a second vertebra; seating a first spinal rod within rod-receiving recess formed in proximal heads of the first and second bone anchors; seating a second spinal rod within outriggers extending laterally outward from the proximal heads of the first and second bone anchors; and at least one of: delivering a thermal medium through a delivery conduit to a chamber formed in the first spinal rod to apply a thermal effect to the first spinal rod; and delivering a thermal medium through a delivery conduit to a chamber formed in the second spinal rod to apply a thermal effect to the second spinal rod.

In some embodiments, a thermal device includes an elongate shaft having a chamber defined therein and a distal end configured for insertion into bone; a thermal source configured to deliver a thermal medium to the chamber of the elongate shaft to apply a thermal effect to the elongate shaft. The elongate shaft can be or can include at least one of a pedicle marker, a bone tap, and a drill bit. The elongate shaft can be rigid along its entire length. The elongate shaft can have a length sufficient to extend from a bone opening in which the distal end of the elongate shaft is disposed to a location proximal to a skin surface overlying said bone opening.

In some embodiments, a method of applying localized thermal therapy includes advancing an elongate shaft into a bone structure of a patient such that a distal end of the shaft is positioned in a bone opening formed in the bone structure and a proximal end of the shaft is disposed outside of the patient; and applying a thermal effect to the elongate shaft to apply localized thermal therapy to the bone structure and tissue adjacent thereto. Applying the thermal effect can include circulating a heated or cooled fluid through a chamber formed in the elongate shaft.

In some embodiments, a thermal device includes a bone plug having a non-threaded cylindrical distal projection configured to be received in a bone hole and a proximal body portion, the bone plug defining a chamber therein; a delivery conduit extending from the proximal body portion, the delivery conduit being configured to supply a thermal medium to the chamber; and an exhaust conduit extending from the proximal body portion, the exhaust conduit being configured to withdraw the thermal medium from the chamber. The proximal body portion can include a plate configured such that, when the distal projection is seated in a bone hole, the plate lies over a surface of the bone structure in which the bone hole is formed. The chamber can extend into the plate. The plate can include at least one opening through which a bone anchor can be received to anchor the plate to bone disposed adjacent thereto.

In some embodiments, a thermal device includes a bone plate having a chamber defined therein; a delivery conduit extending from the bone plate, the delivery conduit being configured to supply a thermal medium to the chamber; and an exhaust conduit extending from the bone plate, the exhaust conduit being configured to withdraw the thermal medium from the chamber.

In some embodiments, a thermal device includes a bone plate having a bone-contacting surface and at least one opening formed therein configured to receive a bone anchor for anchoring the bone plate to bone; and at least one bone anchor having delivery and exhaust conduits extending therefrom configured to circulate a cooled or heated fluid through the first bone anchor. The plate can include a chamber formed therein and delivery and exhaust conduits extending from the plate configured to circulate a cooled or heated fluid through the chamber. The plate can be rigid.

In some embodiments, a method of applying localized thermal therapy includes forming a bone hole in a bone structure of a patient; seating a non-threaded cylindrical distal projection of a bone plug in the bone hole; and delivering a thermal medium through a delivery conduit to a chamber formed in the bone plug to apply a thermal effect to the bone plug and apply localized thermal therapy to the bone structure and tissue adjacent thereto. The adjacent tissue can be or can include neural tissue. The adjacent tissue can be or can include a spinal canal of the patient. The method can include closing an incision through which the bone plug is inserted around the delivery conduit and applying the thermal effect after closing the incision. The method can include removing the bone plug from the bone hole by pulling the delivery conduit proximally through the closed incision and pulling the delivery conduit and the bone plug out of the patient through the closed incision. The method can include decoupling the delivery conduit from the bone plug by pulling the delivery conduit proximally through the closed incision and pulling the delivery conduit out of the patient through the closed incision.

In some embodiments, a method of applying localized thermal therapy, includes positioning a bone plate adjacent to at least one bone structure of a patient; securing the bone plate to the at least one bone structure using one or more bone anchors; delivering a thermal medium through a delivery conduit to a chamber formed in at least one of the bone plate and the one or more bone anchors, thereby applying a thermal effect to the bone plate and applying localized thermal therapy to the at least one bone structure and tissue adjacent thereto. The method can include closing an incision around the delivery conduit. The method can include selectively decoupling the delivery conduit from the bone plate or the bone anchors and removing the delivery conduit through the closed incision.

In some embodiments, a thermal device includes a first clamping arm having a first cavity, a first delivery conduit configured to supply a thermal medium to the first cavity, and a first exhaust conduit configured to withdraw the thermal medium from the first cavity; a second clamping arm pivotally coupled to the first clamping arm, the second clamping arm having a second cavity, a second delivery conduit configured to supply a thermal medium to the second cavity, and a second exhaust conduit configured to withdraw the thermal medium from the second cavity;

the first and second clamping arms each having an engagement portion configured to grasp an implant or an anatomical structure, the engagement portions forming a substantial negative of the implant or the anatomical structure. The first cavity can be formed entirely in a distal portion of the first clamping arm adjacent the engagement portion of the first clamping arm, the first cavity being in fluid communication with the first delivery conduit and the first exhaust conduit via fluid pathways having a reduced cross-section that extend through the first clamping arm; and the second cavity can be formed entirely in a distal portion of the second clamping arm adjacent the engagement portion of the second clamping arm, the second cavity being in fluid communication with the second delivery conduit and the second exhaust conduit via fluid pathways having a reduced cross-section that extend through the second clamping arm.

In some embodiments, a method of applying localized thermal therapy, includes forming an incision in a patient; inserting at least a portion of a clamp through the incision; grasping an implant implanted in a patient or an anatomical structure of the patient with first and second opposed arms of the clamp; and delivering a thermal medium through a first delivery conduit to a first chamber formed in the first arm of the clamp and delivering a thermal medium through a second delivery conduit to a second chamber formed in the second arm of the clamp to apply a thermal effect to the clamp and thereby apply localized thermal therapy to the implant or anatomical structure. The method can include closing the incision around the first and second delivery conduits such that the delivery conduits extend through the closed incision while the clamp remains implanted in the patient. The method can include decoupling the first and second delivery conduits from the clamp after closing the incision and removing the delivery conduit through the closed incision.

In some embodiments, a thermal therapy system includes a disc implant sized and configured for placement between superior and inferior vertebrae, the implant having a superior bone contacting surface, an inferior bone contacting surface, a first side surface configured to face a spinal canal when the implant is disposed between superior and inferior vertebrae, a second side surface opposite to the first side surface, and third and fourth side surfaces extending between the first and second side surfaces; a thermally-conductive member coupled to the implant and configured to extend across at least one surface of the implant; and a thermal probe having a chamber formed therein to which a thermal medium can be delivered to apply a thermal effect to the thermal probe; wherein the thermal probe can be coupled to or placed in contact with the thermally-conductive member to apply the thermal effect to the thermally-conductive member and tissue proximate thereto. The thermally-conductive member can be or can include a plate coupled to the first side surface of the implant. The thermally-conductive member can be a load bearing component of the implant configured to bear physiological loads. The implant can be sized and configured for delivery to a disc space via a lateral approach. The implant can be sized and configured for delivery to a disc space via an anterior approach. The implant can be sized and configured for delivery to a disc space via a posterior approach. The thermally-conductive member can include a first plate coupled to the first side surface of the implant and a second plate coupled to the second side surface of the implant. The thermally-conductive member can include a first thin layer of thermally-conductive material applied to the first side surface of the implant and a second thin layer of thermally-conductive material applied to the second side surface of the implant. The thermally-conductive member can include a C-shaped plate configured to extend across the first side surface and the third and fourth side surfaces of the implant. First and second terminal ends of the plate can sit flush with the second side surface of the implant. The thermally-conductive member can include an O-shaped plate configured to extend across the first side surface, the second side surface, and the third and fourth side surfaces of the implant.

In some embodiments, a method of applying localized thermal therapy includes forming an incision in a patient; inserting at least a portion of a thermal probe through the incision; at least one of coupling the thermal probe to a disc implant disposed within a disc space of a patient and placing the thermal probe in contact with the disc implant; applying a thermal effect to the thermal probe, thereby applying a thermal effect to the disc implant and applying localized thermal therapy to tissue proximate to the disc implant. Applying a thermal effect to the thermal probe can include delivering a thermal medium to a chamber formed in the thermal probe. The method can include closing the incision around the thermal probe such that the thermal probe extends through the closed incision while remaining in contact with or coupled to the implant. The method can include decoupling the thermal probe from the implant after closing the incision and removing the thermal probe through the closed incision.

In some embodiments, a thermal therapy device includes a pad having an upper surface, a lower surface, and a sidewall extending therebetween, the pad defining a chamber therein; a fluid inlet conduit extending from the pad and in fluid communication with the chamber; a fluid outlet conduit extending from the pad and in fluid communication with the chamber; a thermal source coupled to the fluid inlet conduit and the fluid outlet conduit and configured to circulate heated or chilled fluid through a fluid path defined by the fluid inlet conduit, the chamber, and the fluid outlet conduit to apply thermal therapy to anatomy disposed in proximity to the pad. The upper surface of the pad can include one or more grooves or enclosed loops for retaining sutures. The pad can include at least one opening through which fluid can drip from the chamber into surrounding tissue. The at least one opening can include a plurality of openings formed in a grid pattern in the lower surface of the pad. The at least one opening can be formed in a distal-facing portion of the sidewall of the pad. The pad can include at least one suction port through which fluid can be evacuated from the vicinity of the pad through an aspiration conduit. The at least one suction port can be formed in a proximal end of the pad, adjacent to a location at which the inlet and outlet conduits meet the pad. The at least one suction port can be formed in a distal-facing potion of the sidewall of the pad. The pad can include at least one wing extending outward therefrom configured to increase contact area with anatomy of a patient when the pad is placed in contact with said anatomy for at least one of stabilization and adhesion. The pad can include upper and lower rigid shells that define the chamber therebetween. The lower shell can be formed from a thermally-conductive material and the upper shell can be formed from a thermally-insulative material.

In some embodiments, a surgical method includes forming an incision in a patient; inserting a pad through the incision and positioning the pad at a target site within the patient; closing the incision around an aspiration conduit extending proximally from the pad with the pad at the target site; and after closing the incision, aspirating fluid through the aspiration conduit.

In some embodiments, a method of applying localized thermal therapy includes forming an incision in a patient; inserting a pad through the incision and positioning the pad at a target site within the patient; closing the incision around at least one fluid outlet conduit extending proximally from the pad with the pad at the target site; and after closing the incision, delivering a heated or cooled fluid through the at least one fluid conduit to a chamber formed in the pad and releasing at least a portion of the fluid into the target site through one or more openings formed in the pad. The at least one fluid conduit can include an aspiration conduit and the method can include aspirating fluid from the target site through the aspiration conduit. The method can include aspirating fluid from the target site while simultaneously delivering heated or cooled fluid to the pad. Positioning the pad can include positioning the pad under a lamina of the patient. The method can include at least temporarily adhering at least a portion of the pad to a spinal canal of the patient.

In some embodiments, a thermal therapy device can include a length of flexible tubing having first and second free ends, the length of tubing being bent into a predetermined non-linear shape;

a biodegradable or bioabsorbable substrate coupled to the tubing and configured to maintain the tubing in the non-linear shape until the substrate is at least partially dissolved; a thermal source coupled to at least one of the free ends of the tubing and configured to circulate heated or chilled fluid through a fluid path defined by the tubing to apply thermal therapy to anatomy disposed in proximity to the tubing. The length of tubing can have an outside diameter that is less than about 5 mm. The substrate can be or can include a planar sheet to which the tubing is adhered. The tubing can be encapsulated in the substrate. The first and second free ends can be coupled to the thermal source. The length of tubing can include a first interior lumen and a second interior lumen. The first free end can be coupled to the thermal source and the second free end of the tubing can be closed, a fluid communication path between the first and second lumens being defined adjacent the second free end.

In some embodiments, a method of applying localized thermal therapy includes forming an incision in a patient; inserting a length of flexible tubing through the incision and positioning a bent portion of the tubing at a target site within the patient, the bent portion of the tubing being formed into a predetermined non-linear shape and maintained in said shape by a biodegradable substrate coupled to the tubing; closing the incision around an unbent portion of the tubing that extends proximally from the bent portion with the bent portion being positioned at the target site; and after closing the incision, delivering a heated or cooled fluid through the length of tubing to apply localized thermal therapy to tissue in proximity to the bent portion of the tubing. The method can include pulling the length of tubing out of the patient through the closed incision by transitioning the bent portion of the tubing to an unbent configuration after the substrate dissolves in the patient. The unbent portion can include first and second free ends of the length of tubing. The unbent portion can include a first free end of the tubing and the bent portion of the tubing can include a second free end of the tubing. Delivering the fluid can include delivering the fluid into a first inner lumen of the tubing such that the fluid flows through the first inner lumen and then enters a second inner lumen in fluid communication with the first inner lumen adjacent the second free end of the tubing.

The present invention further provides methods, systems, and devices as claimed.

BRIEF DESCRIPTION OF THE DRAWINGS

The invention will be more fully understood from the following detailed description taken in conjunction with the accompanying drawings, in which:

FIG. 4A is a profile view of a bone anchor thermal device with a thread portion of the device shown in phantom;

FIG. 4B is a sectional profile view of the thermal device of FIG. 4A;

FIG. 4C is a sectional profile view of a bone anchor thermal device;

FIG. 5 is a sectional profile view of a guidewire thermal device inserted in a bone anchor;

FIG. 6I is an exploded perspective view of a bone anchor thermal device having a connector;

FIG. 6J is an exploded sectional perspective view of the thermal device of FIG. 6I;

FIG. 9A is a sectional perspective view of a bone anchor insert thermal device inserted in a bone anchor;

FIG. 9B is a perspective view of the thermal device and bone anchor of FIG. 9A;

FIG. 10A is a sectional perspective view of a bone anchor insert thermal device inserted in a bone anchor with a spinal rod;

FIG. 10B is a perspective view of the thermal device, bone anchor, and spinal rod of FIG. 10A;

FIG. 11A is a sectional perspective view of a bone anchor insert thermal device inserted in a bone anchor;

FIG. 11B is a perspective view of the thermal device and bone anchor of FIG. 11A;

FIG. 18A is a sectional perspective view of a spinous process thermal device and first and second spinous processes;

FIG. 18B is another sectional perspective view of the thermal device of FIG. 18A;

FIG. 18C is a perspective view of the thermal device of FIG. 18A and first and second spinous processes;

FIG. 38A is a perspective view of an interbody thermal device;

FIG. 38B is a plan view of the thermal device of FIG. 38A;

FIG. 38C is an exploded plan view of the thermal device of FIG. 38A;

FIG. 39I is a perspective view of a pad thermal device;

FIG. 39J is a perspective view of a pad thermal device;

FIG. 39K is a sectional perspective view of the thermal device of FIG. 39J;

FIG. 39L is a perspective view of a pad thermal device;

FIG. 39M is a sectional perspective view of the thermal device of FIG. 39L;

FIG. 39N is a perspective view of a pad thermal device;

FIG. 39O is a sectional perspective view of the thermal device of FIG. 39N;

FIG. 40A is a perspective view of a tubing thermal device;

FIG. 40B is a perspective view of the thermal device of FIG. 40A with a substrate removed;

FIG. 40C is a sectional plan view of the thermal device of FIG. 40A;

FIG. 41A is a perspective view of a tubing thermal device;

FIG. 41B is a perspective view of the thermal device of FIG. 41A with a substrate removed;

Figure 40A:
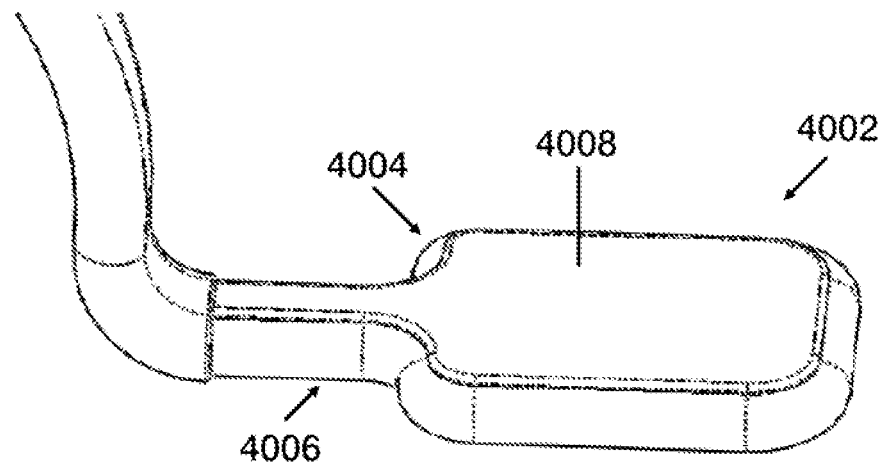
Figure 41A:
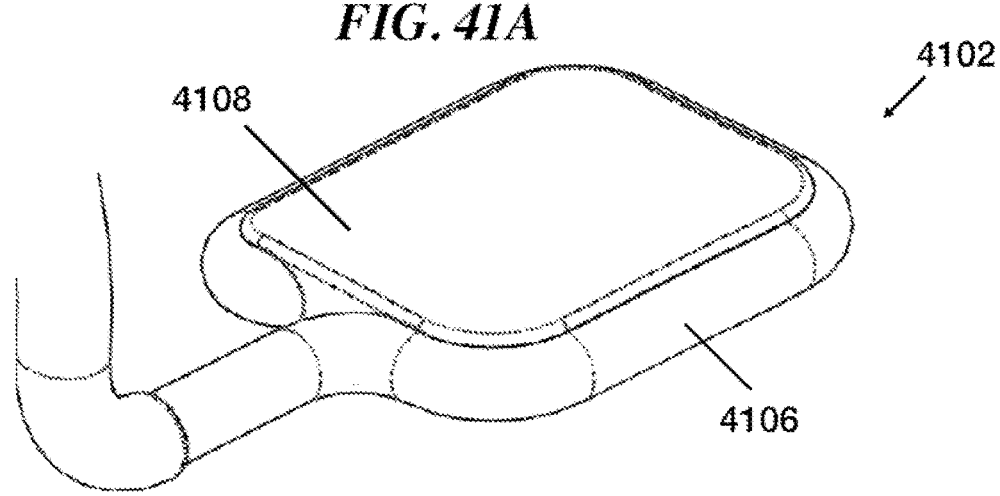
Figure 41B:
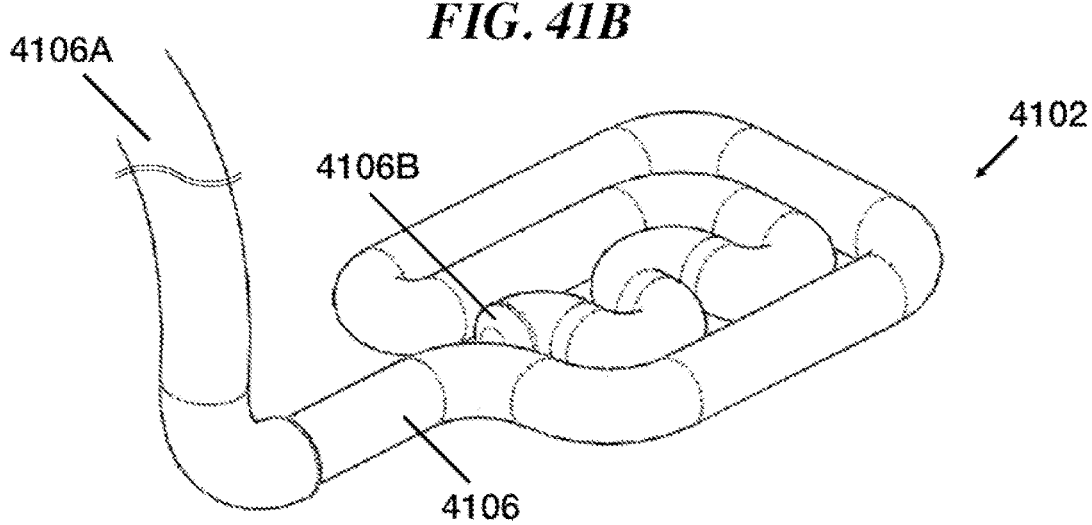
Figure 41C:
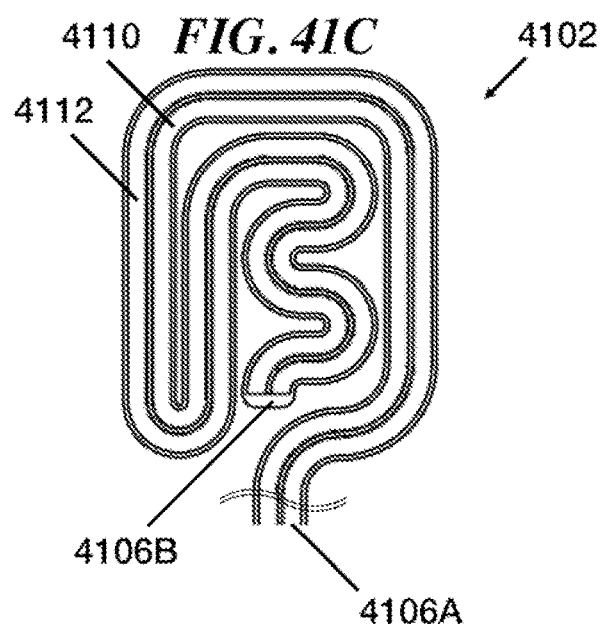
Figure 42:
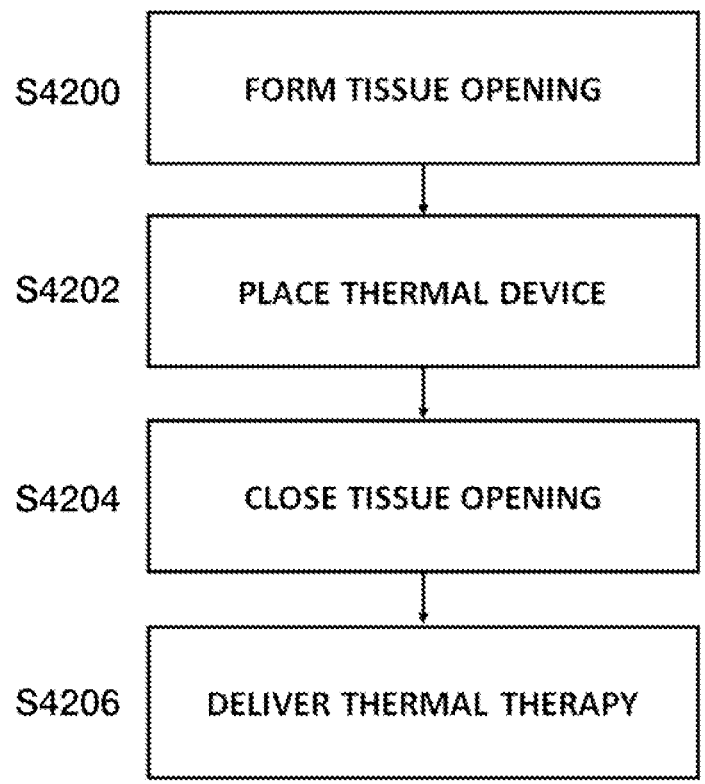

FIG. 41C is a sectional plan view of the thermal device of FIG. 40A;

FIG. 42 is a flowchart of an exemplary method of applying thermal therapy; and

Figure 43:
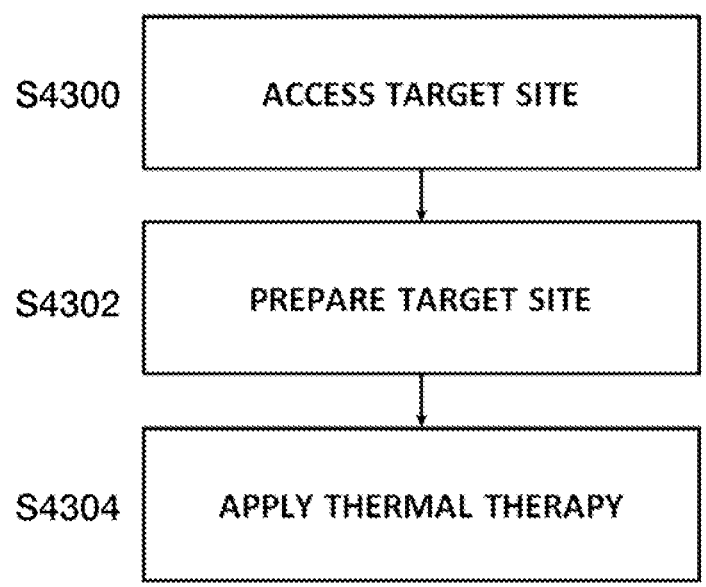

FIG. 43 is a flowchart of an exemplary method of applying thermal therapy.

DETAILED DESCRIPTION

Methods and devices are disclosed herein that generally involve applying thermal therapy to tissue (e.g., localized cooling or heating of tissue), and in particular applying thermal therapy to the spinal canal, tissue disposed within the spinal canal, and/or nerve roots extending from the spinal canal. In some embodiments, tissue can be cooled or heated by implanting or positioning a thermal device in proximity to the targeted tissue. A number of exemplary thermal devices are disclosed, including bone anchors, inserts for use with bone anchors, K-wires, bone anchor extensions or towers, cross-connectors, spinous process plates, spinal rods, pedicle markers, bone taps, drill bits, bone plugs, bone plates, clamps, interbody or disc implants, thermal pads, and tubing loops. The thermal device can be left in place following surgery to facilitate application of post-surgical thermal therapy. In some embodiments, the thermal device can be removed post-surgery in a minimally- or non-invasive manner.

Certain exemplary embodiments will now be described to provide an overall understanding of the principles of the structure, function, manufacture, and use of the methods and devices disclosed herein. One or more examples of these embodiments are illustrated in the accompanying drawings. Those skilled in the art will understand that the methods and devices specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

In the description that follows, reference is made primarily to treating tissue in and around the spinal canal, including the spinal cord, but it will be appreciated that the methods and devices disclosed herein can also be used to treat tissue in virtually any part of a human or animal body, including organs, joints (e.g., hips, knees, elbows, shoulders), the brain, the heart, etc. It will also be appreciated that the term "spinal tissue" as used herein can include the spinal cord itself, as well as nerves and nerve roots extending therefrom through spaces in the spinal column, together the "spinal neuraxis," as well as other portions of the central nervous system.

Furthermore, while methods and devices for cooling tissue are primarily disclosed herein, it will be appreciated that the same or similar methods and devices can be used to heat tissue, e.g., for the purpose of applying localized therapeutic hyperthermia.

In some embodiments, methods of applying thermal therapy involve "implanting" a thermal device in the patient. As used herein, "implanting" the thermal device refers to leaving at least a portion of the thermal device in the patient after the initial surgical phase of treatment is completed (e.g., by closing a tissue opening over the implanted device while tubing or connectors associated therewith extend through the closed incision). Implanting the thermal device facilitates delivery of postoperative thermal therapy, optionally for an extended time period or in multiple sessions over a prolonged period, which can provide unexpected benefits for the patient.

For example, peak edema typically does not subside until about three to five days after a spinal cord injury is sustained. With an implantable system, therapeutic hypothermia can be delivered throughout this period to minimize swelling-related damage to the patient's spinal cord. The ability to implant the thermal device also allows for the patient to be closed immediately following decompression, stabilization, or other surgery that may be performed in connection with implanting the device, yet still preserves the ability to apply thermal therapy for extended time periods. It is desirable to conclude the initial surgical phase of treatment as soon as possible so as to reduce the patient's exposure to possible infection, reduce the amount of time the patient must be under anesthesia, reduce the cost of the surgery by reducing the amount of time required of surgeons, operating staff, operating rooms, and other resources, improve hospital throughput by freeing up resources to treat other patients, and so forth.

The thermal device can be left implanted for any amount of time (e.g., at least about 1 hour, at least about 4 hours, at least about 12 hours, at least about 18 hours, at least about 24 hours, at least about 48 hours, at least about 72 hours, at least about 5 days, at least about 7 days, at least about 2 weeks, at least about 1 month, at least about 3 months, at least about 6 months, at least about 1 year, at least about 5 years, at least about 10 years, and/or permanently or indefinitely).

System

Figure 1:
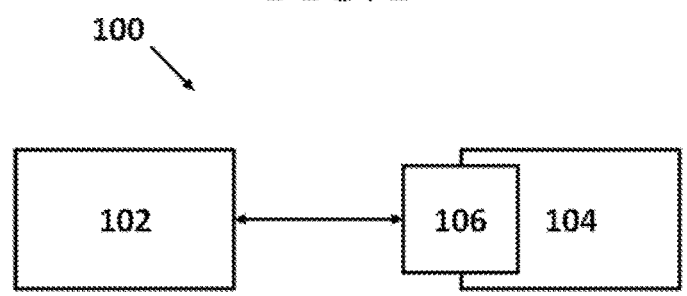
FIG. 1 is a schematic view of a system for applying thermal therapy.

FIG. 1 illustrates an exemplary embodiment of a system 100 for applying thermal therapy. The system 100 generally includes a thermal device 102 and a source 104 configured to provide a cooling or heating means to the device 102. Delivery of the cooling or heating means can be regulated by a controller 106. The thermal device 102 can include one or more bone anchors, inserts for use with bone anchors, K-wires, bone anchor extensions or towers, cross-connectors, spinous process plates, spinal rods, pedicle markers, bone taps, drill bits, bone plugs, bone plates, clamps, interbody or disc implants, thermal pads, tubing loops, containers, pouches, balloons, sacs, etc. that can be positioned in proximity to tissue that is to be cooled or heated. A number of exemplary thermal devices 102 are described in detail below. The thermal device 102 can be placed in direct contact with the tissue to be cooled or heated, or can apply a cooling or heating effect to the tissue in an indirect manner, e.g., through intermediate tissue, implants, or other structures.

Exemplary tissue that can be cooled or heated using the thermal device 102 includes the spinous process, the vertebral body, the pedicles, the laminae, the spinal canal, the spinal canal contents (including the spinal cord), nerves (including those surrounding or extending to/from the spinal cord), vessels, and muscles. The spinal canal contents include, for example, epidural space, dura mater, subdural space, arachnoid space, subarachnoid space, intrathecal space, cerebral spinal fluid, pia mater, spinal arteries and veins, vasocorona, vertebral venous plexus, nerve roots, ligaments, and fatty tissue. It will be appreciated that there is symmetry as well as repetitive elements to a vertebra and referral to an element of the vertebra can be taken to mean any one of symmetric or multiple elements. For example, when referring to a pedicle, it can be intended to mean any one of the two, or both, pedicles of the vertebra.

Cooling/Heating Means and Source

The thermal device 102 can provide a cooling or heating effect using any of a number of different cooling or heating means or combinations thereof. For example, the cooling means can include the expansion of gas within the thermal device 102 or the circulating of a chilled fluid through the thermal device 102. The term "fluid," as used herein, refers to any flowable material or collection of materials, including liquids, gases, and combinations thereof. In some embodiments, the thermal device 102 receives a compressed gas which by expansion acts as a coolant in the thermal device 102. The expansion of the gas causes the gas and the thermal device 102 around it to experience a rapid decrease in temperature. Typical gases for such an application include Nitrous Oxide and Carbon Dioxide, but it will be appreciated that there are a wide variety of gases that can be used, including gases which, in compressed form, will be liquid.

In other embodiments, the thermal device 102 receives a chilled liquid as the cooling means which flows through cavities or channels of the thermal device, thereby decreasing the temperature of the thermal device. Typical chilled liquids include saline solutions, water, liquid nitrogen, and ethyl alcohol. It will be appreciated that any number of fluids can be used as the cooling means, and that there are advantages to using biologically safe fluids. In still other embodiments, the thermal device 102 can include a thermoelectric device, such as a Peltier device, which when a voltage or current is applied, at least a portion of the device experiences a reduction in temperature. The thermal device 102 can also house an endothermic chemical reaction which results in the reduction of temperature of the contents of the thermal device 102 and of the thermal device 102 itself. In other embodiments, the thermal device 102 is pre-chilled prior to a cooling procedure. It will be appreciated by those skilled in the art that there are a variety of means by which the thermal device 102 can be cooled.

In embodiments in which the thermal device 102 is used to apply heat, a heated fluid or gas can be circulated through the device, the device can include an electric heating element (e.g., a resistive heating element), the device can be pre-heated, the device can house an exothermic reaction, etc.

The thermal source 104 can be external (e.g., extracorporeal), can be implanted in the patient, and/or can be formed integrally with the thermal device 102. In implementations in which the cooling means is an expanding gas, the thermal source 104 can be a tank of compressed gas which is released into the thermal device 102 through a cooling delivery conduit. Once the compressed gas is in the thermal device 102, it can be expanded through an expansion nozzle into an expansion chamber in the thermal device 102, causing a rapid decrease in temperature. Alternatively, or in addition, the thermal source 104 can include a compressor that compresses the gas. In some implementations, the delivery of the cooling means from the tank of compressed gas is regulated with the control unit 106 to limit the amount of gas and the pressure at which it enters the thermal device 102 via the cooling delivery conduit. The control unit 106 can be an adjustable valve on the tank, which can be manually controlled, mechanically controlled, or automatically controlled by a computing device. In implementations in which the thermal source 104 includes a compressor, the control unit 106 can control the degree to which the compressor compresses the gas, or the pressure of the gas presented down the conduit. The regulation of the release of the gas can be managed manually or automatically, in either case, based on established protocols, conditions of the patient, and/or detectable physiological characteristics of the patient or characteristics of the thermal device.

An additional conduit can also be provided to exhaust expanded gas from the expansion chamber of the thermal device 102. The exhaust conduit can exhaust the gas into the atmosphere, to a collection tank, or to a compressor which in turn re-compresses the gas for reuse. As discussed further below, the delivery conduit and the exhaust conduit can be generally circular in cross-section, and can be formed from any of a variety of medical-grade tubing materials known in the art. The conduits can be flexible or rigid, or can include rigid portions and flexible portions. Any of the conduits disclosed herein can be a multi-lumen conduit (e.g., one in which a first lumen is used to deliver a thermal medium and a second lumen is used to extract or withdraw the thermal medium). The lumens of a multi-lumen conduit can be coaxial (e.g., a tube within a tube). The lumens of a multi-lumen conduit can also be arranged in other configurations. For example, multiple lumens can be coupled to one another such that they run in a parallel, side-by-side arrangement. By way of further example, a conduit having a circular outside cross-section can include one or more internal dividing walls to define a multiple lumen internal cross-section (e.g., a double-D cross-sectional configuration). Multi-lumen conduits can be formed using any of a variety of techniques, including co-extrusion processes.

In implementations in which the cooling means is a chilled fluid, the thermal source 104 can be or can include a chiller or other apparatus for cooling and pumping fluid, and the cooling delivery conduit can be a tube for delivering the chilled fluid to the thermal device 102. In this case, the exhaust conduit can be used to return or exhaust the chilled fluid from the thermal device 102 back to the thermal source 104, to a collection tank, or to a drain. In such an implementation, the control unit 106 can control the volume rate of chilled fluid flow, the pressure of the chilled fluid delivery lines, and/or the temperature of the chilled fluid. It will be appreciated that components of the fluid delivery and circulation system can be positioned on the exhaust side of the system rather than the source side (e.g., a pumping mechanism that pulls the chilled fluid through the device 102, the delivery conduit, and the exhaust conduit rather than pushing it through).

In implementations in which the cooling means is a Peltier device embedded in the thermal device 102, the thermal source 104 can include a power supply that powers the Peltier device, and the cooling delivery conduit can include electrical lines that supply electrical current from the power supply to the Peltier device. The delivery and exhaust conduits can also be used to remove heat generated by the Peltier device from the thermal device 102.

Delivery of the cooling means can be regulated to achieve a predetermined cooling effect, such as a specific temperature at a specific location. Delivery of the cooling means can also be regulated such that a specific volume of the cooling means is delivered, for example in cases where the cooling means includes a chilled liquid or expandable gas. Delivery of the cooling means can also be regulated based on changes or lack of changes in physiological characteristics. For example, the regulation of the cooling means, and thus the intensity of cooling, can be determined by quantitative and qualitative sensory or motor-evoked potential (SEP, MEP) observations. In this example, the cooling means is provided at a certain level until the patient's SEP/MEP results begin to degrade, improve, or otherwise change, at which point the regulation of the cooling means can begin to reduce or increase the delivery of the cooling means.

It will be appreciated that any number of physiological characteristics can be used to regulate the intensity of the cooling means, including but not limited to: blood pressure, target-tissue temperature, specific tissue temperature (proximate to target tissue), rectal body temperature, venous blood temperature near or exiting target tissue, pulmonary conditions, cardiac conditions, sensory evoked potentials (SEPs, including somatosensory evoked potentials), motor-evoked potentials (MEPs), intrathecal pressure, perfusion pressure, levels of blood oxygen & glucose, ATP concentrations, and effectors of excitotoxicity, vasogenic edema, apoptosis, inflammation, and enzymatic responses. A real-time qualitative or quantitative determination can be made based on any of the listed physiological characteristics as to how the cooling means should be regulated.

One or more sensors can also be included in the thermal device 102 and/or implanted in or around the patient. The sensor can be a temperature sensor embedded in or on the thermal device 102 to sense the temperature the device exhibits, where this sensed temperature can then be used to control the delivery of the cooling means to the thermal device 102. The sensor can be connected to the control unit 106 via one or more sensor wires to provide a feedback loop of information to help determine how much cooling means and/or what temperature cooling means to deliver to the thermal device 102. Alternatively, or in addition, the sensor can be connected via sensor wires to a display, meter, dial, or other indicator providing some form of output data from the sensor that can allow one to manually regulate the delivery of the cooling means. The sensor can also be connectable wirelessly and a wireless link can be used instead of the sensor wires.

In one implementation, a first sensor is embedded into the thermal device 102 and provides temperature data of the thermal device 102 and a second sensor is implanted in the intrathecal space of the spinal canal to measure temperature of cerebral spinal fluid. This temperature data can be used to either manually or automatically regulate the delivery of the cooling means.

It will be appreciated that more than one sensor, more than one sensor type, and more than one sensor placement location can be used simultaneously and that the data gathered from the multiple sensors can be used independently or in combination to determine how the delivery of the cooling means is regulated. Exemplary sensors that can be used include temperature sensors (e.g., thermistors or thermocouples), pressure sensors, chemical sensors, electrical sensors, magnetic sensors, and optical sensors. Other types of sensing, such as remote sensing, can be used that do not require the sensor itself to be placed within the patient—ultrasound, including Doppler measurements, and functional MRI, all can be used to sense physiological characteristics that can be used to control or regulate the delivery of the cooling means. The information measured by a sensor or sensors can be used to continually adjust the regulation of the delivery of the cooling means in real time or almost real time. Alternatively, or in addition, the sensed information can be used for safety monitoring. The advantages of using a sensor or sensors, along with sensor wires or other communication means, will be appreciated though their use may not be necessary.

Thermal Devices

A number of exemplary thermal devices are described below. Any of these thermal devices can be used with the system described above and can include any of the features described above. In addition, the various features of the thermal device described below can be readily interchanged or combined with one another, and the specific arrangements shown and described are merely exemplary.

Bone Anchor Thermal Devices

Figure 2A:
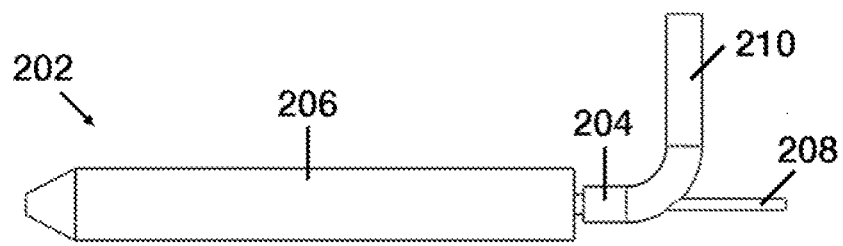
FIG. 2A is a profile view of a bone anchor insert thermal device inserted in a bone anchor.
Figure 2B:
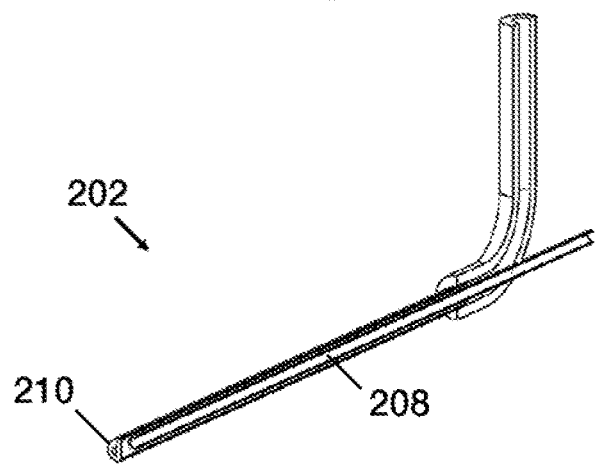
FIG. 2B is a sectional perspective view of the thermal device of FIG. 2A.
Figure 2C:
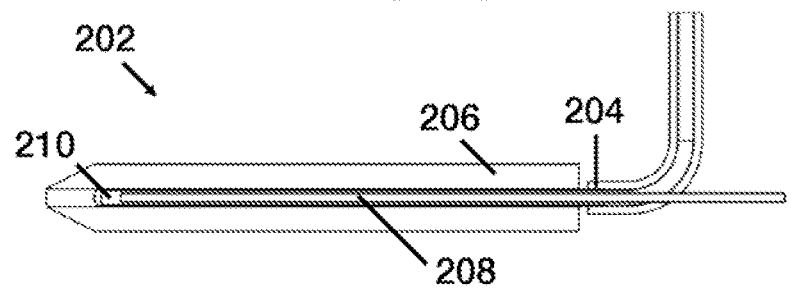
FIG. 2C is a sectional profile view of the thermal device and bone screw of FIG. 2A.

FIGS. 2A-2C illustrate an exemplary thermal device 202. The device 202 includes a plug or insert 204 that can be inserted into a standard cannulated bone anchor (e.g., a bone screw 206). The plug 204 can include first and second concentric tubes 208, 210 configured to be positioned in the cannulation of the bone screw to define inner and outer chambers. The distal end of the inner tube 208 can be open such that fluid can exit the distal end of the inner tube and flow into the outer tube 210 adjacent a distal end thereof. The distal end of the outer tube 210 can be closed such that fluid entering the outer tube adjacent a distal end thereof must flow back along the length of the outer tube towards a proximal end of the outer tube. Cooled or heated fluid can be directed through an inlet conduit and through the inner chamber defined by the inner tube 208. The fluid can exit the distal end of the inner tube 208 and flow back along the outer chamber defined by the outer tube 210 and into an outlet conduit. The inlet conduit can be concentric with the outlet conduit over a portion of its length, and can then exit a sidewall of the outlet conduit at a location proximal to the bone screw 206. In some embodiments, fluid can flow in the opposite direction through the device 202. In use, the thermal device 202 can be inserted into the cannulation of a bone anchor placed using standard techniques, and a cooled or heated medium can be directed through the device to heat or cool the bone anchor and apply localized thermal therapy to target anatomy in proximity thereto.

Figure 3A:
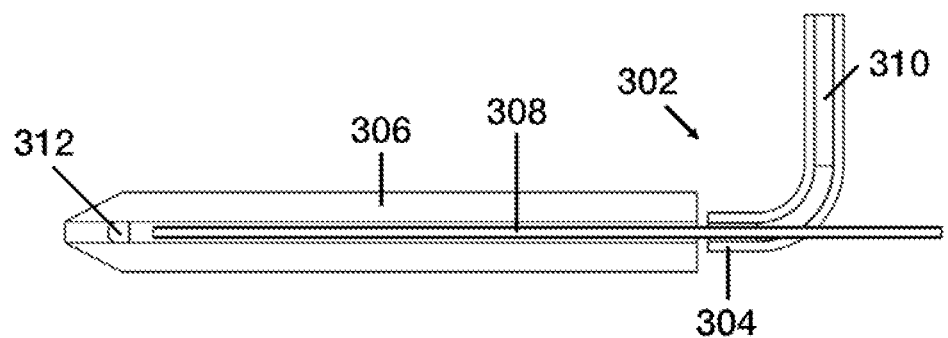
FIG. 3A is a sectional profile view of a bone anchor insert thermal device inserted in a bone anchor with a capped cannulation.

FIG. 3A illustrates an exemplary thermal device 302. The thermal device 302 is similar to the thermal device 202, except that the outer tube is omitted and the outer chamber is instead defined by the screw cannulation. A cap 312 can be positioned within a distal end of the cannulation of the screw 306 to seal the distal end. A plug or insert 304 can be inserted into the proximal end of the screw. While not shown, it will be appreciated that the plug 304 can be inserted into the cannulation of the bone anchor or a recess formed proximal to the cannulation to form a fluid tight seal with the bone anchor. Cooled or heated fluid can be directed through a delivery conduit, through the plug 304, and through a tube 308 extending from the plug through the cannulation. The fluid can exit an open distal end of the tube 308 and flow back along the cannulation of the screw 306 to the plug 304 and into an exhaust conduit 310. The delivery conduit can be concentric with the exhaust conduit over a portion of its length, and can then exit a sidewall of the exhaust conduit at a location proximal to the plug 304. In some embodiments, fluid can flow in the opposite direction through the device 302. In use, the thermal device 302 can be inserted into the cannulation of a bone anchor placed using standard techniques, and a cooled or heated medium can be directed through the device and the bone anchor to cool or heat the bone anchor and apply localized thermal therapy to target anatomy in proximity thereto.

Figure 3B:
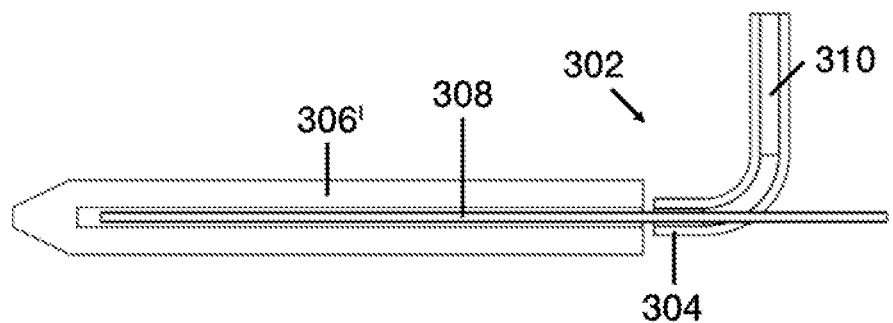
FIG. 3B is a sectional profile view of the thermal device of FIG. 3A inserted in a bone anchor with an incomplete cannulation.
Figure 3C:
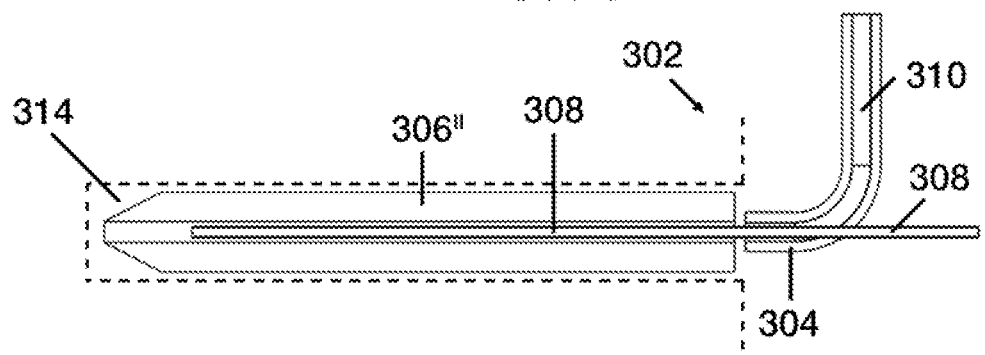
FIG. 3C is a sectional profile view of the thermal device of FIG. 3A inserted in a bone anchor with a complete cannulation.

As shown in FIG. 3B, the thermal device 302 can be used with a partially cannulated bone anchor 306' (e.g., a bone anchor in which the cannulation does not extend through the distal end of the anchor such that the distal end of the anchor is closed). In such instances, the cap 312 can be omitted. As shown in FIG. 3C, the patient's anatomy (e.g., the end of a blind bore 314 formed in a bony structure of a patient's spine) can be used to seal the distal end of a fully-cannulated bone anchor 306" instead of or in addition to the cap 312.

FIGS. 4A-4C illustrate an exemplary thermal device 402. The thermal device 402 can be generally in the form of a bone anchor having a threaded distal portion 404 and an enlarged head portion (not shown). The bone anchor can include any of a variety of known features, including a head portion that defines a recess in which a spinal fixation element such as a spinal rod can be received. A fluid flow conduit 406 can be defined within the threads 408 of the bone anchor (e.g., entirely within the threads of the bone anchor). In use, cooled or heated fluid can be directed through the conduit 406 to apply a thermal effect (e.g., heating or cooling) to the screw and/or to surrounding tissue. In some embodiments, the conduit 406 can be wrapped around the screw shaft independent from the threads 408. The device 402 can include a single-lumen conduit 406 in the thread as shown in FIG. 4B, or can include a multi-lumen conduit 406' having delivery and exhaust lumens 410, 412 as shown in FIG. 4C. In the embodiment of FIG. 4B, fluid delivered through the single-lumen conduit 406 can be returned through an exhaust conduit (not shown) that extends through a central portion of the bone screw. The helical pattern of the thermal conduit can advantageously deliver a more uniform thermal effect across the length and circumference of the bone anchor.

FIG. 5 illustrates an exemplary thermal device 502. The thermal device 502 can include a thermal clamp 504 configured to clamp onto a proximal portion of a standard guidewire, K-wire, or other elongate structure 506 inserted through the cannulation of a standard bone anchor 508. The thermal clamp 504 can include a chamber or conduit formed therein through which a heated or cooled fluid can be circulated to heat or cool the K-wire 506, the bone anchor 508, and/or surrounding tissue. The K-wire 506 can be formed from a thermally conductive material to facilitate transfer of the heating or cooling effect to the bone anchor 508. In some embodiments, a portion of the K-wire 506 intermediate to a distal portion that sits within the cannulation of the bone anchor 508 and a proximal portion that is grasped by the clamp 504 can be coated with a thermally-insulating material to reduce the delivery of the thermal effect to non-targeted tissue.

FIGS. 6A-6H illustrate an exemplary thermal device 602. The thermal device generally includes a bone anchor 604 (e.g., a bone screw) and a conduit connector 606 configured to be selectively coupled and/or decoupled from the bone anchor.

The conduit connector 606 can be configured to couple elongate fluid inlet and outlet conduits 608, 610 to corresponding fluid lumens defined in or extending through the bone anchor 604. In the illustrated embodiment, the connector 606 include a body portion 612 having a proximal end from which the fluid inlet and outlet conduits 608, 610 can extend. The fluid inlet and outlet conduits 608, 610 can be formed integrally with the connector 606, or can be coupled thereto using any of a variety of techniques, including threaded engagement, snap-fit engagement, welding, gluing, etc. The body portion 612 can have fluid lumens 614, 616 defined therein to provide fluid communication between the inlet and outlet conduits 608, 610 and the fluid lumens of the bone anchor 604. The connector 606 can also include one or more mating features for selectively coupling the connector to the bone anchor. For example, the connector 606 can include first and second tabs 618 extending distally from the body portion 612 configured to be received within corresponding first and second slots or channels 620 formed in the bone anchor. The tabs 618 can be sized to form a slight interference fit with the slots 620 in the bone anchor such that the connector is securely coupled to the bone anchor until a sufficient proximally-directed force is applied to decouple the connector from the bone anchor. The connector 606 can also include male projections 622 through which the fluid lumens of the connector extend configured to be received within corresponding female receptacles 624 of the bone anchor 604 to establish a fluid-tight seal and provide fluid communication between the connector and the bone anchor.

The bone anchor 604 can include a proximal tulip portion 626 that defines a U-shaped recess 628 in which a spinal fixation element (e.g., a spinal rod) can be received. The U-shaped recess 628 can be defined by opposed arms 630. Inner and/or outer surfaces of the opposed arms 630 can be threaded to receive a locking element (e.g., a set screw or a locking nut) to secure a spinal fixation element within the U-shaped recess 628. The tulip portion 626 can include fluid inlet and outlet lumens defined therein. For example, one or both of the opposed arms 630 can include fluid inlet and/or outlet lumens.

Figure 6A:
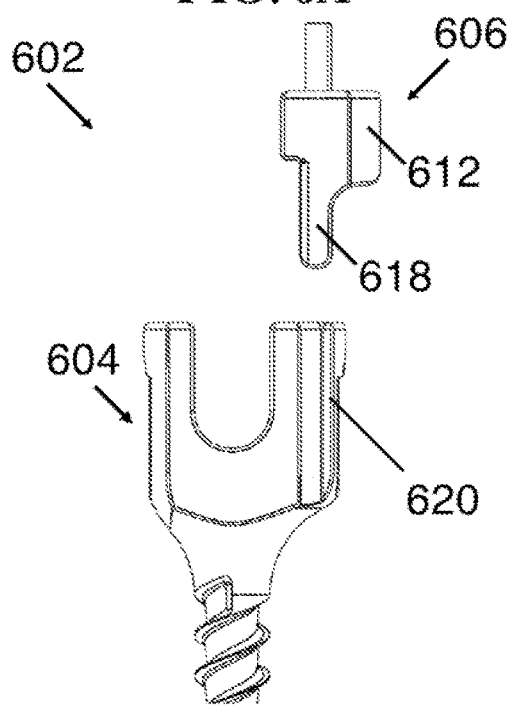
FIG. 6A is an exploded profile view of a bone anchor thermal device having a connector.
Figure 6B:
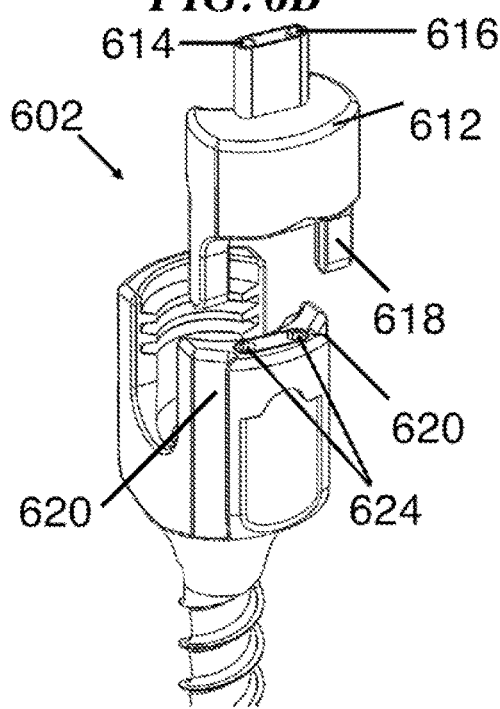
FIG. 6B is an exploded perspective view of the thermal device of FIG. 6A.
Figure 6C:
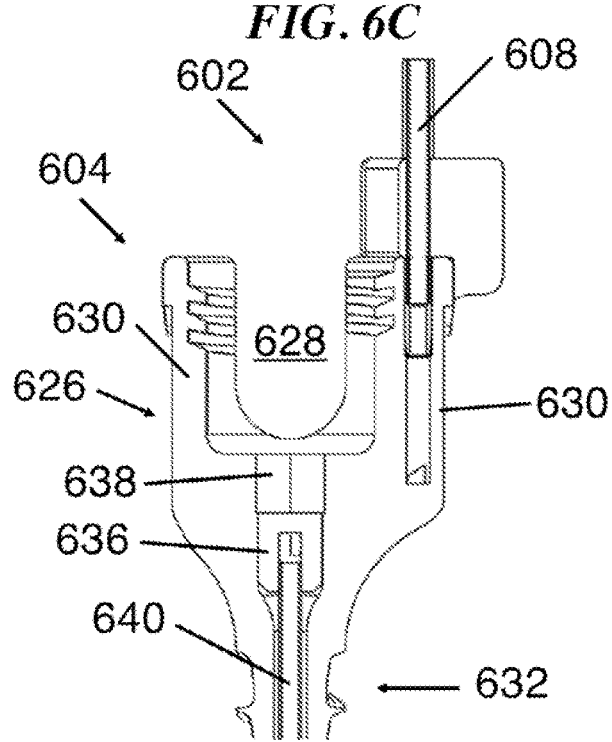
FIG. 6C is a sectional profile view of the thermal device of FIG. 6A.
Figure 6D:
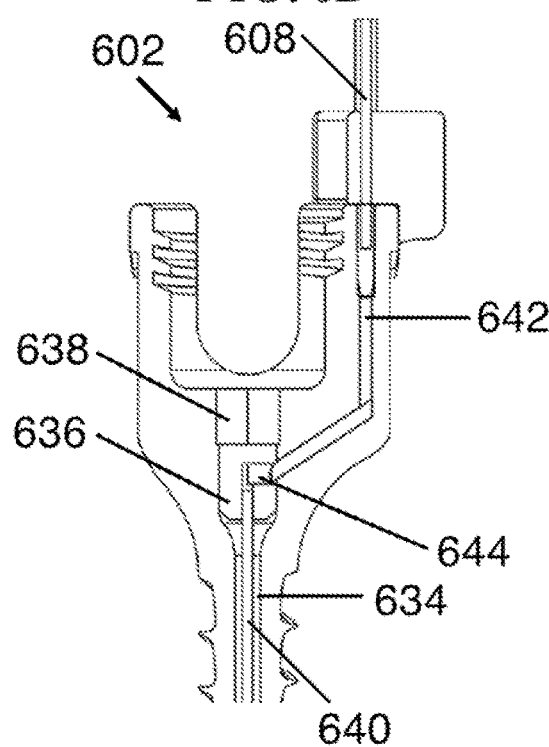
FIG. 6D is another sectional profile view of the thermal device of FIG. 6A.
Figure 6E:
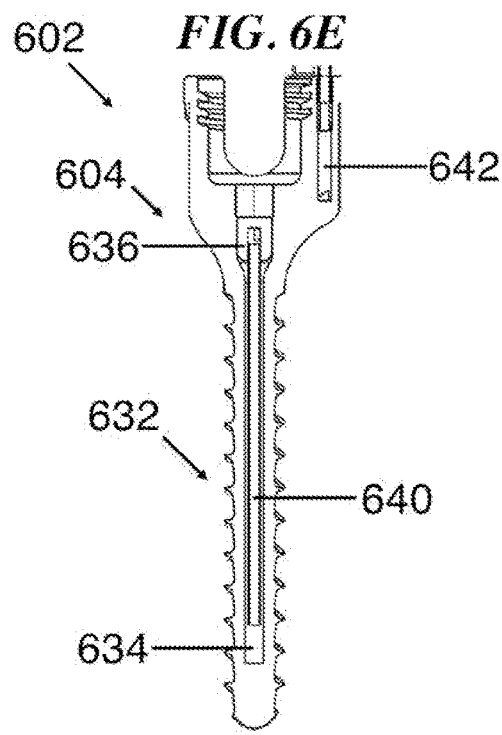
FIG. 6E is another sectional profile view of the thermal device of FIG. 6A.
Figure 6F:
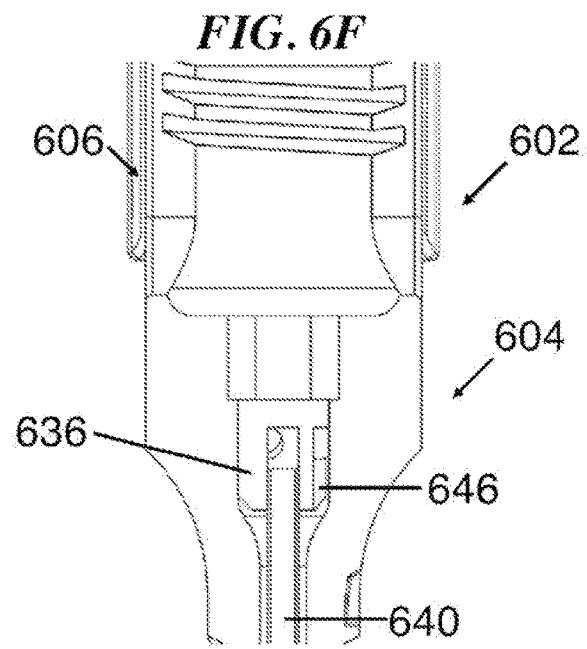
FIG. 6F is another sectional profile view of the thermal device of FIG. 6A.
Figure 6G:
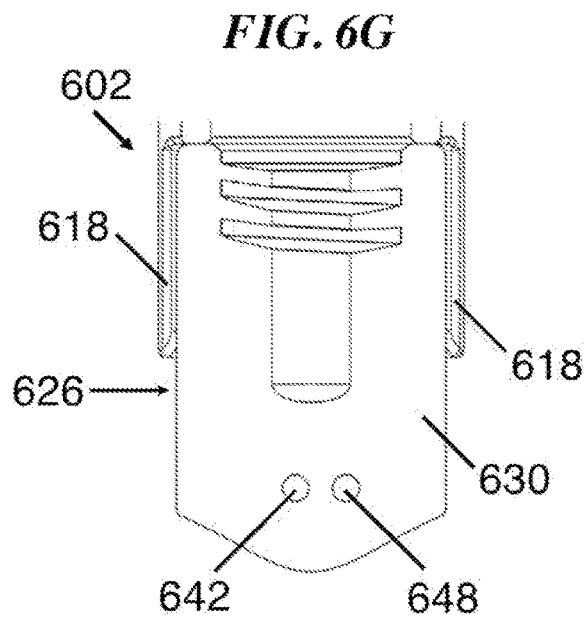
FIG. 6G is another sectional profile view of the thermal device of FIG. 6A.
Figure 6H:
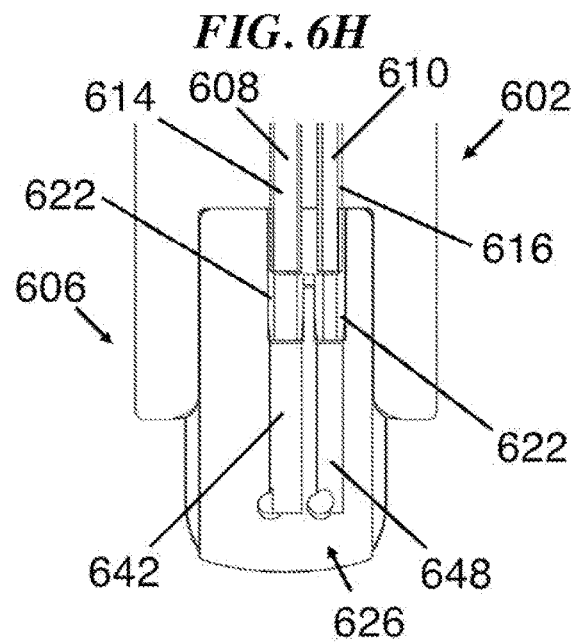
FIG. 6H is another sectional profile view of the thermal device of FIG. 6A.

The bone anchor 604 can also include a distal portion 632 configured to be received within a bone opening. The distal portion 632 can include a threaded exterior surface configured to engage bone. The distal portion 632 can also include a central cannulation 634 extending therethrough. The cannulation 634 can extend entirely through the distal portion of the bone anchor or only along a portion thereof. For example, a distal end of the cannulation 634 can be closed as shown in FIG. 6E.

The thermal device 602 can also include a plug or insert 636 seated in a proximal end of the cannulation 634. The plug 636 can be seated just below a female driving interface 638 of the bone anchor. The plug 636 can include at least one tube 640 that extends distally therefrom into the cannulation 634 of the bone anchor. The plug 636 can be securely mated to the bone anchor, for example using a threaded or snap fit interface or by welding, gluing, etc. The plug 636 can include sealing features to form a fluid-tight seal with the bone anchor when the plug is seated therein. For example, the plug can include one or more O-rings or gaskets disposed about a circumference thereof configured to form a seal with an internal sidewall of the bone anchor.

When the thermal device 602 is assembled, as shown in FIGS. 6C-6H which show sectional views of the thermal device 602 in various planes, a fluid loop can be defined through the thermal device. In particular, fluid can flow through an inlet conduit 608, through an inlet passage 614 of the connector 606, through an inlet passage 642 of the tulip 626, through an inlet passage 644 of the plug 636, and through an inlet tube 640 extending distally from the plug. The fluid can then enter the cannulation 634 of the bone anchor where it can encounter a cap disposed in the cannulation or a closed distal end of the cannulation, causing the fluid to return proximally through the cannulation. The fluid can then enter an outlet passage 646 of the plug and flow through an outlet passage 648 of the tulip 626, an outlet passage 616 of the connector 606, and into an outlet conduit 610. In some embodiments, fluid can flow in the opposite direction through the device 602.

In use, heated or cooled fluid can be supplied through the inlet conduit 608 and can flow through the thermal device 602 and back out through the outlet conduit 610 to heat or cool the thermal device and surrounding tissue. When the thermal therapy is completed, or at any other desired time, the connector 606 can be de-coupled from the bone anchor 604 (e.g., by applying a proximally-directed force of sufficient magnitude) and the connector and associated inlet/outlet conduits can be removed from the patient. The bone anchor 604 can be left in place and used as part of a spinal fixation or stabilization construct. As described in further detail below, the patient can be closed up with just the inlet and outlet conduits 608, 610 extending through the closed incision, such that thermal therapy can be performed after the surgical procedure to implant the thermal device 602. Later, the connector 606 and the fluid inlet and outlet conduits 608, 610 can be decoupled from the bone anchor 604 in a non-surgical or minimally-invasive procedure by simply pulling the conduits and the connector through the closed incision.

In the thermal device 602, the positioning of the fluid passages within the arms 630 of the tulip 626 can advantageously leave the U-shaped opening 628 in the tulip clear to receive a spinal fixation element. Accordingly, localized thermal therapy can be delivered via the thermal device 602 before, during, and/or after a spinal fixation element is secured to the bone anchor 604 without interfering with the installation of the spinal fixation element.

The illustrated device 602 uses a single tube 640 extending distally from the plug 636 and a cannulation 634 of the bone anchor 604 to define a fluid path through the distal portion of the bone anchor. It will be appreciated, however, that other variations are also possible, including any of those described above with respect to FIGS. 2A-3C.

In some embodiments, as shown in FIGS. 6I-6J, the thermal device 602 can be configured such that the fluid path extends only through the tulip portion 626 of the bone anchor 604 and does not extend into the distal portion 632 of the bone anchor. In particular, the fluid path can be defined such that fluid flows through the inlet conduit 608, through an inlet passage 614 in the connector, and through an inlet passage 642 in the tulip (e.g., in one of the opposed arms 630 of the tulip), at which point the fluid is then routed back to an outlet passage 648 in the tulip (e.g., in the same or a different arm 630 of the tulip), through an outlet passage 616 in the connector, and through the outlet conduit 610. Such an arrangement can advantageously provide for a simpler and less expensive thermal device 602 as compared with embodiments in which the fluid path extends through the distal portion of the bone anchor. In addition, the bone anchor can be a multi- or polyaxial bone anchor (e.g., a bone anchor in which the distal portion comprises a threaded shank and a head portion seated in a separate tulip component such that an angle of the threaded shank with respect to the tulip can be adjusted).

FIGS. 7A-7D illustrate an exemplary thermal device 702. Except as indicated below, the structure and operation of the thermal device 702 is substantially identical to the thermal device 602, and therefore a detailed description is omitted here for the sake of brevity. In the thermal device 702, a fluid inlet lumen can be formed in a first arm 730A of the tulip portion 726 of the bone anchor 704 and a fluid outlet lumen can be formed in a second, opposite arm 730B of the tulip portion. Accordingly, cooled or heated fluid can be directed through a fluid path that extends through an inlet passage 742 of a first arm 730A of the tulip, an inlet passage 744 of the plug 736, and an inlet tube 740 extending distally from the plug. The fluid can then enter a cannulation 734 of the bone anchor 704 adjacent a distal end of the bone anchor, return along the cannulation, through an outlet passage 746 of the plug 736, and through an outlet passage 748 of a second, opposite arm 730B of the tulip 726.

The fluid inlet and outlet passages formed in the opposed arms of the tulip can include openings formed in a proximal-facing surface of the tulip. Fluid inlet and outlet conduits can be coupled to said openings (e.g., via first and second connectors of the type described above modified to include only a single fluid passage in each connector).

Figure 7A:
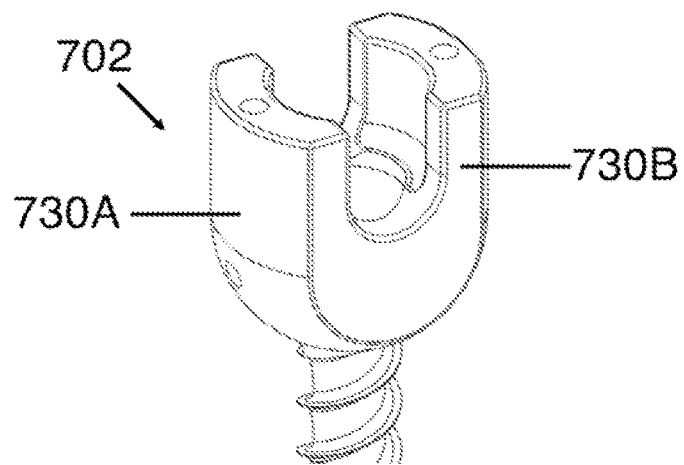
FIG. 7A is a perspective view of a bone anchor thermal device.
Figure 7B:
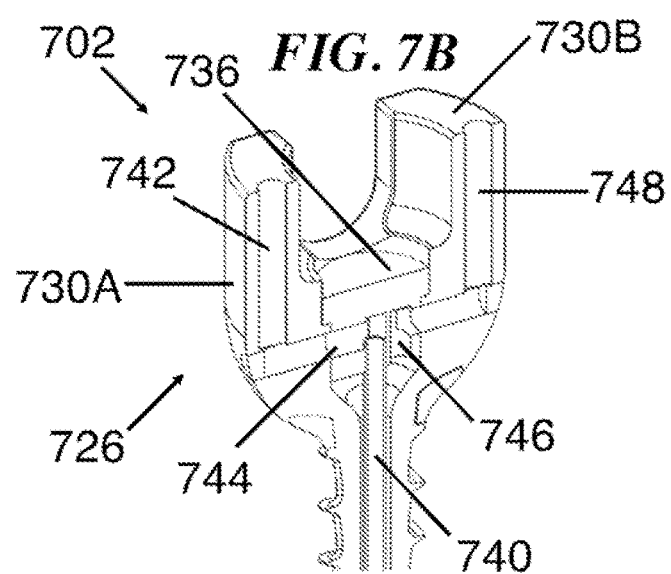
FIG. 7B is a sectional perspective view of the thermal device of FIG. 7A.
Figure 7C:
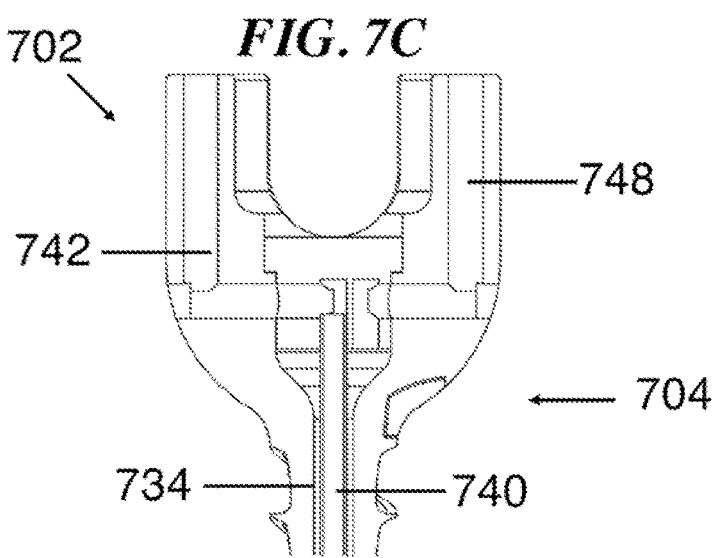
FIG. 7C is a sectional profile view of the thermal device of FIG. 7A.
Figure 7D:
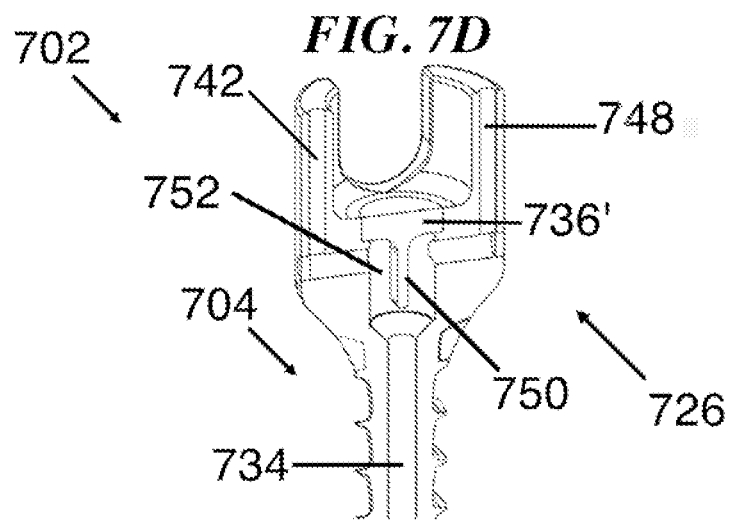
FIG. 7D is a sectional perspective view of the thermal device of FIG. 7A with an alternative plug design.

As shown in FIG. 7D, the plug 736' can optionally include features to facilitate unforced convective flow of heated or cooled fluid through the device. For example, the center plug 736' disposed in the tulip 726 can include a tab or diverter 750 extending distally therefrom into a chamber 752 defined in the base of the tulip. The tab 750 can be formed from one or more pieces, can extend in any of a variety of directions, and can have any of a variety of shapes or patterns. The tab 750 can be formed integrally with or can be attached, bonded, or coupled to the center plug 736' as shown, or to any interior surface of the bone anchor. The tab 750 can extend into the cannulation 734 of the screw shaft. In some embodiments, the tab 750 can extend to the distal end of the cannulation of the screw shaft. In operation, fluid flows around the tab 750, which can direct the fluid flow and can create turbulence.

Figure 8A:
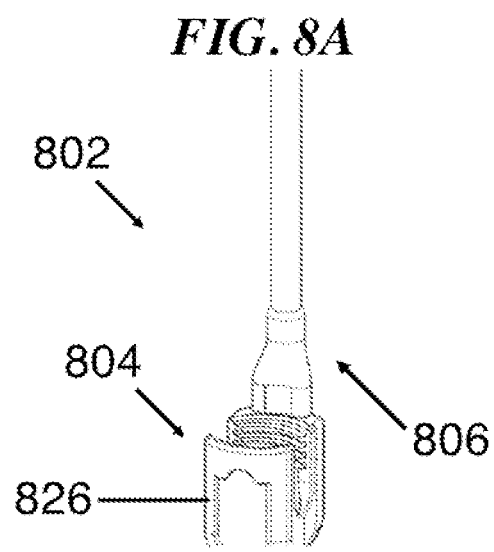
FIG. 8A is a perspective view of a bone anchor thermal device.
Figure 8B:
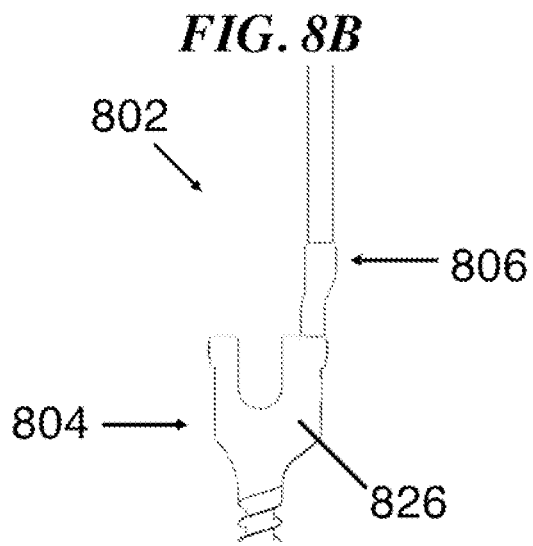
FIG. 8B is a profile view of the thermal device of FIG. 8A.

FIGS. 8A-8B illustrate an exemplary thermal device 802. Except as indicated below, the structure and operation of the thermal device 802 is substantially identical to the thermal device 602, and therefore a detailed description is omitted here for the sake of brevity. In the thermal device 802, the connector 806 has a low-profile design. The connector 806 can include a distal-facing surface with male projections in which fluid passages are defined extending therefrom. The connector 806 can be coupled to the tulip portion 826 of a bone anchor 804 such that the distal-facing surface of the connector abuts a proximal-facing surface of the tulip portion and such that the male projections in which the fluid passages are defined are received within corresponding female receptacles formed in the tulip portion. The connector 806 can be press-fit or otherwise coupled to the tulip portion 826 (e.g., at the time of manufacture) and can subsequently be selectively decoupled from the tulip portion (e.g., by applying a proximally-directed force of sufficient magnitude to separate the press-fit or other engagement).

FIGS. 9A-9B illustrate an exemplary thermal device 902. The device 902 generally includes a bone anchor 904 (e.g., a bone screw) and a plug or insert 906 configured to be selectively coupled and/or decoupled from the bone anchor.

The bone anchor 904 can include a proximal tulip portion 908 that defines a U-shaped recess 910 in which a spinal fixation element (e.g., a spinal rod) can be received. The U-shaped recess 910 can be defined by opposed arms 912. Inner and/or outer surfaces of the opposed arms 912 can be threaded to receive a locking element (e.g., a set screw or a locking nut) to secure a spinal fixation element within the U-shaped recess 910. The tulip portion 908 can also include opposed cut-outs or reliefs 914 aligned with and formed beneath or distally to the U-shaped recess 910.

The bone anchor 904 can also include a distal portion 916 configured to be received within a bone opening. The distal portion 916 can include a threaded exterior surface configured to engage bone. The distal portion 916 can also include a central cannulation 918 extending therethrough. The cannulation 918 can extend entirely through the distal portion of the bone anchor or only along a portion thereof. For example, a distal end of the cannulation can be closed.

The plug or insert 906 can be seated in a bore defined in a base portion of the tulip 908. The plug 906 can be seated in the bore in a flush or sub-flush manner such that the plug does not protrude proximally into the U-shaped channel 910 defined by the tulip. The plug 906 can include or can be coupled to fluid inlet and outlet conduits 920, 922 which can extend laterally outward from the plug. The inlet and outlet conduits 920, 922 can be seated in the cut-outs or reliefs 914 formed in the tulip 908 when the plug 906 is seated in the bore. Accordingly, the plug 906 and the fluid conduits 920, 922 can be installed in the bone anchor 904 without interfering with placement or securement of a spinal fixation element (e.g., a spinal rod) within the U-shaped recess 910 of the bone anchor. The plug 906 can also include an inlet tube 924 extending distally therefrom into the cannulation 918 of the bone anchor. The plug can be securely mated to the bone anchor, for example using a threaded or snap fit interface or by welding, gluing, etc. The plug can include sealing features to form a fluid-tight seal with the bone anchor when the plug is seated therein. For example, the plug can include one or more O-rings or gaskets disposed about a circumference thereof configured to form a seal with an internal sidewall of the bone anchor.

When the thermal device 902 is assembled, a fluid loop can be defined through the thermal device. In particular, fluid can flow through the inlet conduit 920, through an inlet passage 926 of the plug 906, and through an inlet tube 924 extending distally from the plug. The fluid can then enter the cannulation 918 of the bone anchor 904 where it can encounter a cap disposed in the cannulation or a closed distal end of the cannulation, causing the fluid to return proximally through the cannulation. The fluid can then enter an outlet passage 928 of the plug and flow through the outlet conduit 922. In some embodiments, fluid can flow in the opposite direction through the device 902.

In use, heated or cooled fluid can be supplied through the inlet conduit 920 and can flow through the thermal device 902 and back out through the outlet conduit 922 to heat or cool the thermal device and surrounding tissue. When the thermal therapy is completed, or at any other desired time, the conduits 920, 922 can be de-coupled from the plug 906 (e.g., by applying a proximally-directed force of sufficient magnitude) and removed from the patient. The bone anchor 904 and the plug 906 can be left in place and used as part of a spinal fixation or stabilization construct. In other words, the conduits can be separated from the thermal device 902 even after a spinal rod or other fixation element is secured within the U-shaped recess 910 of the bone anchor 904. As described in further detail below, the patient can be closed up with just the inlet and outlet conduits 920, 922 extending through the closed incision, such that thermal therapy can be performed after the surgical procedure to implant the thermal device. Later, the fluid inlet and outlet conduits 920, 922 can be decoupled from the bone anchor 904 in a non-surgical or minimally-invasive procedure by simply pulling the conduits through the closed incision.

In the thermal device 902, the positioning of the fluid conduits 920, 922 beneath the U-shaped recess 910 can advantageously leave the U-shaped recess clear to receive a spinal fixation element. Accordingly, localized thermal therapy can be delivered via the thermal device 902 before, during, and/or after a spinal fixation element is secured to the bone anchor 904 without interfering with the installation of the spinal fixation element.

The illustrated device 902 uses a single tube 924 extending distally from the plug 906 and a cannulation 918 of the bone anchor 904 to define a fluid path through the distal portion of the bone anchor. It will be appreciated, however, that other variations are also possible, including any of those described above with respect to FIGS. 2A-3C.

FIGS. 10A-10B illustrate an exemplary thermal device 1002. Except as indicated below, the structure and operation of the thermal device 1002 is substantially identical to the thermal device 902, and therefore a detailed description is omitted here for the sake of brevity. In the thermal device 1002, the inlet and outlet conduits 1020, 1022 can exit the bone anchor 1004 on the same side of the bone anchor. Accordingly, the bone anchor 1004 can include only a single cut-out or relief 1014 formed beneath or distal to the U-shaped recess 1010 on only a single side of the tulip 1008.

FIGS. 11A-11B illustrate an exemplary thermal device 1102. Except as indicated below, the structure and operation of the thermal device 1102 is substantially identical to the thermal device 902, and therefore a detailed description is omitted here for the sake of brevity. In the thermal device 1102, the plug 1106 sits proud of the bore 1107 formed in the bone anchor 1104 and the plug can include first and second lateral extensions 1109 that are received in the U-shaped recess 1110 defined between the opposed arms of the tulip. Accordingly, it is not necessary that the tulip 1108 include cut-outs or reliefs formed beneath or distal to the U-shaped recess 1110, and therefore the plug 1106 can be used with any of a variety of standard, off-the-shelf bone anchors. The fluid inlet and outlet conduits 1120, 1122 can be oriented to extend laterally outward, substantially perpendicular to a longitudinal axis of the tulip 1108.

Figure 12A:
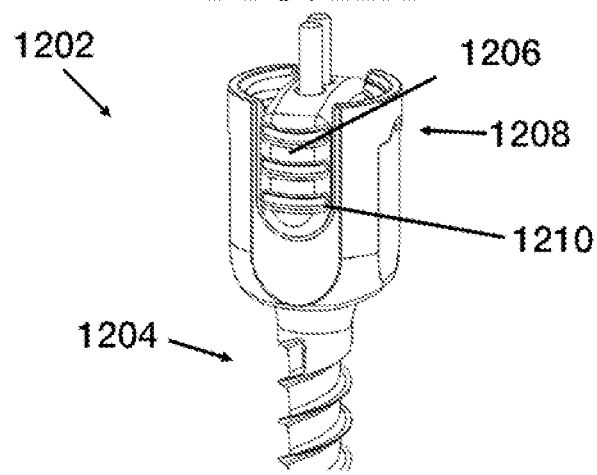
FIG. 12A is a perspective view of a bone anchor insert thermal device inserted in a bone anchor.
Figure 12B:
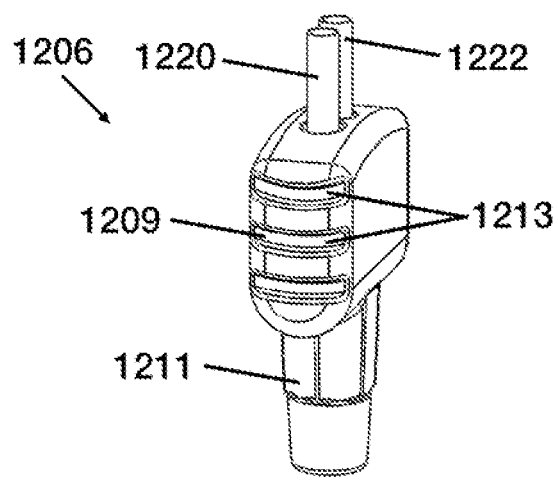
FIG. 12B is a perspective view of the thermal device of FIG. 12A.
Figure 12C:
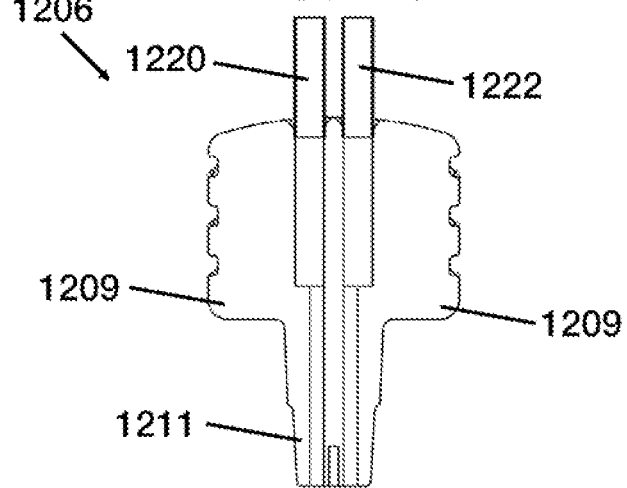
FIG. 12C is a sectional profile view of the thermal device of FIG. 12A.

FIGS. 12A-12C illustrate an exemplary thermal device 1202. Except as indicated below, the structure and operation of the thermal device 1202 is substantially identical to the thermal device 902, and therefore a detailed description is omitted here for the sake of brevity. In the thermal device 1202, the plug 1206 sits proud of the bore formed in the bone anchor 1204 and the plug can include first and second lateral extensions 1209 that are received in the U-shaped recess 1210 defined between the opposed arms of the tulip 1208. Accordingly, it is not necessary that the tulip 1208 include cut-outs or reliefs formed beneath or distal to the U-shaped recess 1210, and therefore the plug 1206 can be used with any of a variety of standard, off-the-shelf bone anchors. The fluid inlet and outlet conduits 1220, 1222 can be oriented to extend substantially parallel to a longitudinal axis of the tulip 1208. The plug 1206 can include a distal extension 1211 sized and shaped to fit within or form a substantial negative of a driving interface of the bone anchor 1204, such that the distal extension can be received within the driving interface to couple the plug to the bone anchor. The plug 1206 can also include gripping features 1213 (e.g., a plurality of parallel ribs or protrusions) formed on the lateral extensions 1209 of the plug to facilitate coupling or decoupling of the plug to the bone anchor.

Figure 12D:
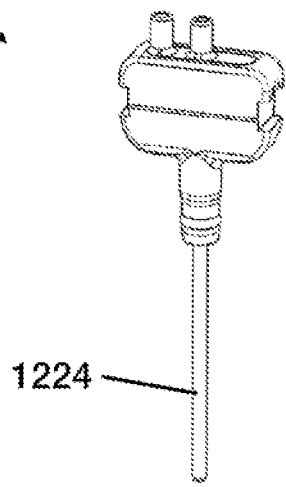
FIG. 12D is a perspective view of a bone anchor insert thermal device.
Figure 12E:
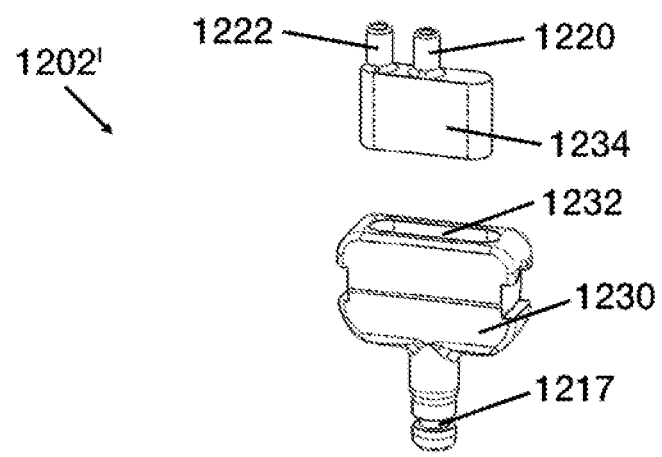
FIG. 12E is an exploded perspective view of the thermal device of FIG. 12D.
Figure 12F:
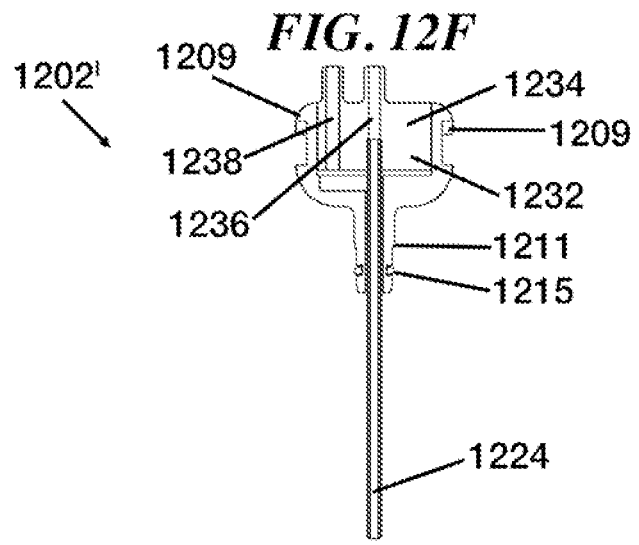
FIG. 12F is a sectional profile view of the thermal device of FIG. 12D.

FIGS. 12D-12F illustrate an exemplary thermal device 1202'. Except as indicated below, the structure and operation of the thermal device 1202' is substantially identical to the thermal device 902, and therefore a detailed description is omitted here for the sake of brevity. In the thermal device 1202', the plug 1206 sits proud of the bore formed in the bone anchor (not shown) and the plug can include first and second lateral extensions 1209 that are received in the U-shaped recess defined between the opposed arms of the tulip. Accordingly, it is not necessary that the tulip include cut-outs or reliefs formed distal to the U-shaped recess, and therefore the plug 1206 can be used with any of a variety of standard, off-the-shelf bone anchors. The fluid inlet and outlet conduits 1220, 1222 can be oriented to extend substantially parallel to a longitudinal axis of the tulip. The plug 1206 can include a distal extension 1211 sized and shaped to fit within or form a substantial negative of a driving interface of the bone anchor, such that the distal extension can be received within the driving interface to couple the plug to the bone anchor. A sealing member such as an O-ring 1215 can be seated within a groove 1217 formed in the distal extension 1211 to form a seal between the plug 1206 and the bone anchor 1204 when the plug is seated therein. The plug 1206 can also include an elongate tube 1224 that extends through the distal extension 1211 and extends distally therefrom, such that the tube is configured to be received within a cannulation of a bone anchor. The cannulation can be closed at the distal end, such that the tube forms a fluid delivery path and the cannulation of the screw forms a fluid return path. As shown in FIG. 12E, the plug 1206 can be formed from multiple components to facilitate manufacturing. In particular, the plug 1206 can include a main housing 1230 in which a recess 1232 is machined and an insert 1234 that defines first and second fluid pathways 1236, 1238 therein. The insert 1234 can be received within the recess of the main housing 1230 to assemble the plug. When assembled, a first fluid pathway 1236 of the insert can be in fluid communication with the tube 1224, and a second fluid pathway 1238 of the insert can be in fluid communication with the recess 1232 formed in the main housing and the cannulation of a bone anchor in which the plug is inserted.

FIGS. 13A-13D illustrate an exemplary thermal device 1302. The device 1302 generally includes an elongate sleeve 1304 (e.g., a screw extension or tower) configured to couple to a bone anchor 1306. In some embodiments, the thermal device 1302 can provide a minimally-invasive pathway between a skin incision at a proximal end of the device and a bone anchor disposed at a distal end of the device through which implants such as spinal fixation elements can be inserted. The sleeve 1304 can include an elongate tubular body with opposed cut-outs formed in a distal end thereof to define first and second opposed distal tabs 1308. The tabs 1308 can include one or more mating features for coupling the thermal device to the bone anchor. For example, the inner surfaces of the tabs can include a recess 1310 configured to receive a protrusion 1312 formed on the tulip portion 1314 of the bone anchor. Alternatively, or in addition, the inner surfaces of the tabs 1308 can include a projection configured to be received within a recess formed in the tulip portion.

Figure 13A:
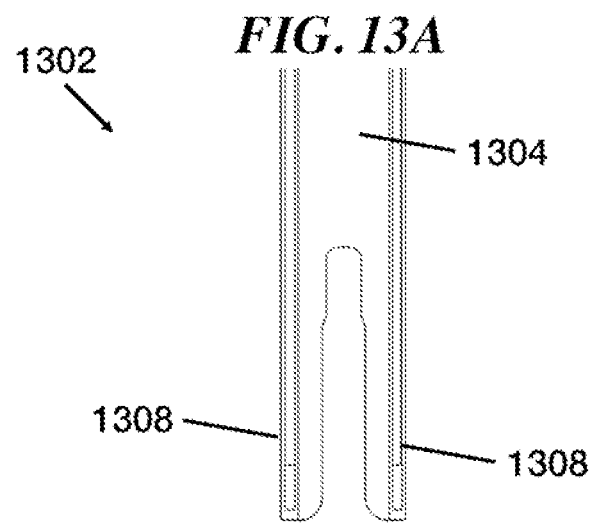
FIG. 13A is a sectional profile view of a bone anchor extension thermal device.
Figure 13B:
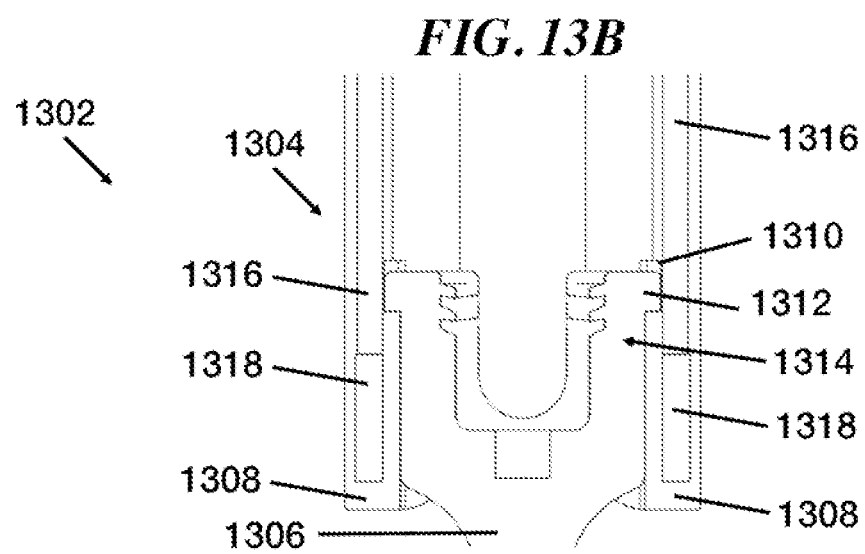
FIG. 13B is a sectional profile view of the thermal device of FIG. 13A coupled to a bone anchor.
Figure 13C:
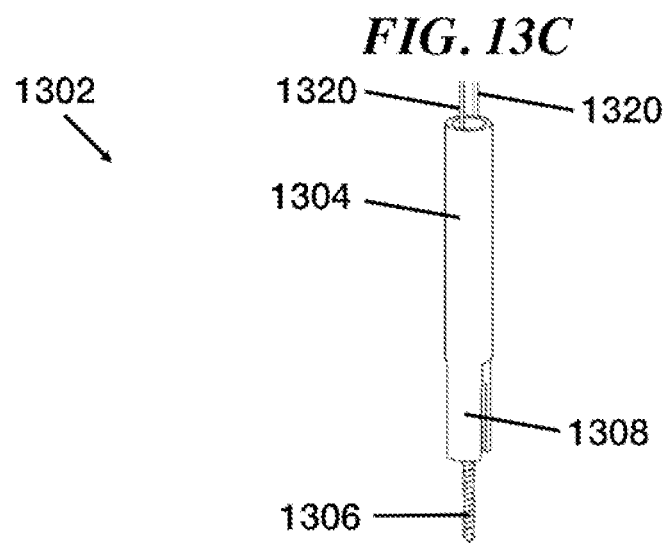
FIG. 13C is a perspective view of the thermal device of FIG. 13A coupled to a bone anchor.
Figure 13D:
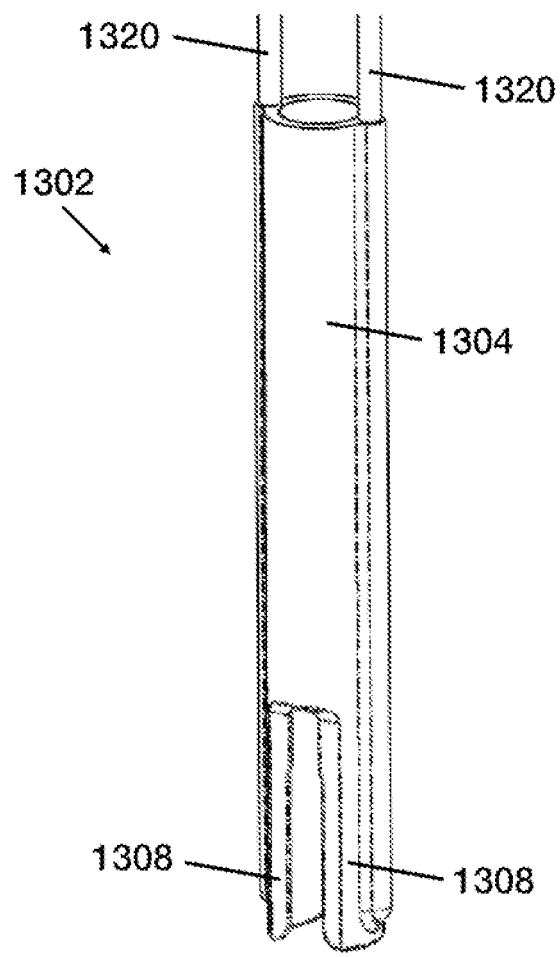
FIG. 13D is a perspective view of a bone anchor extension thermal device.

The sleeve 1304 can include one or more fluid passages defined therein through which heated or cooled fluid can be circulated to apply a thermal effect to a bone anchor to which the device is coupled and tissue proximate thereto. In the illustrated embodiment, the sleeve 1304 includes two dual-lumen fluid loops 1316 formed in diametrically-opposed positions about the circumference of the sleeve. Each loop 1316 can include an inlet portion that extends from a proximal end of the sleeve to a distal fluid chamber 1318 and an outlet portion that extends from the distal fluid chamber to the proximal end of the sleeve. The fluid loops 1316 can be aligned with the tabs 1308 of the sleeve such that the fluid loops extend into a portion of the sleeve configured to be adjacent to the bone anchor 1306 when the bone anchor is coupled to the sleeve. The fluid loops 1316 can be embedded within the sleeve such that the sleeve has a constant, cylindrical outside diameter, as shown in FIG. 13C. The fluid loops 1316 can also be coupled to the exterior sidewall of the sleeve, or embedded in protrusions formed in the exterior sidewall of the device, as shown in FIG. 13D. Fluid conduits 1320 can be coupled to the proximal end of the sleeve 1304 to deliver and extract fluid from the device. In the illustrated embodiment, each conduit includes multiple internal lumens (e.g., an inlet lumen and an outlet lumen).

Cross-Connector Thermal Devices

Figure 14A:
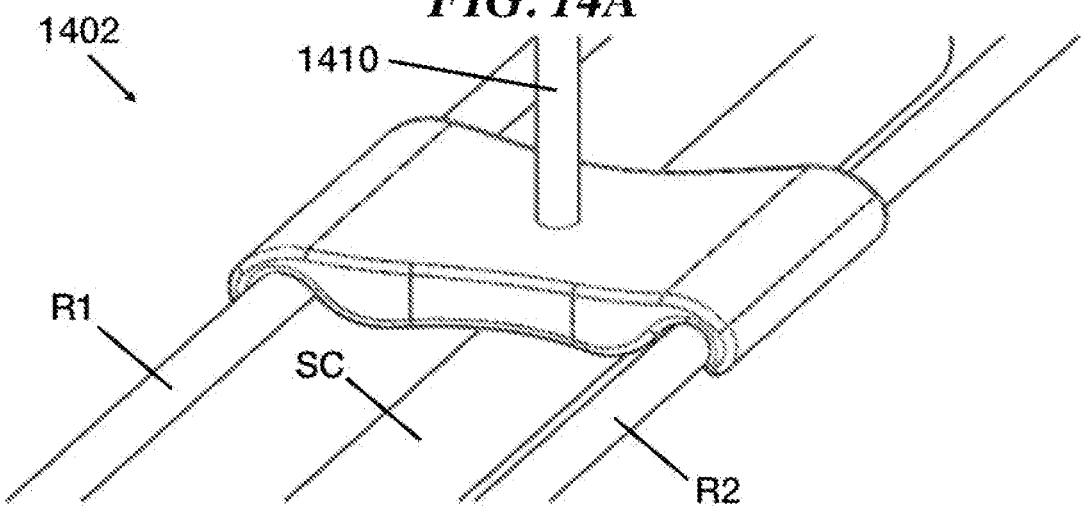
FIG. 14A is a perspective view of a cross-connector thermal device coupled to first and second spinal rods.
Figure 14B:
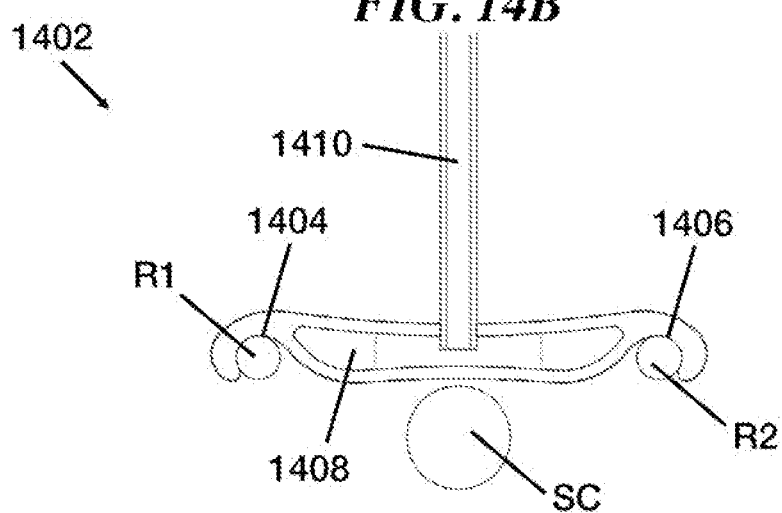
FIG. 14B is a sectional profile view of the thermal device of FIG. 14A shown adjacent to a spinal canal.

FIG. 14A-14B illustrate an exemplary thermal device 1402. The device 1402 generally includes a connector configured to couple a first spinal fixation element (e.g., a first spinal rod) to a second spinal fixation element (e.g., a second spinal rod). For example, the connector can be used as a cross-connector to couple first and second spinal rods R1, R2 disposed on contralateral sides of a patient's spinal column SC to one another. The connector can include first and second recesses 1404, 1406 configured to receive corresponding first and second spinal fixation elements therein. The connector can also include one or more locking elements (e.g., cams, set screws, bolts, etc.) configured to secure and/or lock the connector to the spinal fixation elements. The connector can have multiple points of contact with the first and second spinal rods. While a unitary connector is shown, it will be appreciated that the connector can include multiple components coupled to one another in a movable relationship and/or such that the position and orientation of the components can be locked relative to one another. For example, the rod receiving recesses can 1404, 1406 can be formed in components which are separate from a main body of the connector. The rod-receiving components can be movable relative to the main body (e.g., rotatable, translatable, etc.).

The connector 1402 can include a cavity 1408 formed therein through which heated or chilled fluid can be circulated to apply a thermal effect to the connector and to tissue proximate thereto. For example, as shown in FIG. 14B, the cavity 1408 can be disposed adjacent a patient's spinal canal SC when the connector 1402 is coupled to first and second spinal rods R1, R2 disposed on contralateral sides of the patient's spinal column. In embodiments in which the connector includes multiple components, the cavity can be formed in any one or more of the separate components. The device 1402 can include inlet and outlet conduits configured to supply and withdraw fluid, respectively, from the cavity. The conduits can be selectively detachable from the connector 1402 to facilitate post-surgical withdrawal of the conduits. A multi-lumen conduit 1410 that includes an inlet lumen and an outlet lumen can be coupled to the connector 1402 at a substantial midpoint of the connector as shown. Alternatively, or in addition, discrete inlet and outlet conduits can be coupled to the connector 1402 at opposed ends of the chamber 1408 to facilitate directional flow of fluid through the chamber. In some embodiments, the connector 1402 can have a width of at least about 5 mm. In some embodiments, the connector can have a width of at least about 10 mm.

In use, the device 1402 can be coupled to first and second spinal fixation elements R1, R2 to augment a fixation or stabilization construct or to provide physical protection to an exposed spinal canal SC. Cooled or heated fluid can be circulated through the cavity 1408 of the device 1402 to apply localized thermal therapy to a target treatment region disposed beneath or proximate to the cavity (e.g., the dura of a patient's spinal canal). After completion of the thermal therapy, or at any other desired time, the inlet and outlet conduits can be separated from the device (e.g., by pulling the conduits proximally) and the connector 1402 can be left in place indefinitely. As described in further detail below, the patient can be closed up with just the inlet and outlet conduits extending through the closed incision, such that thermal therapy can be performed after the surgical procedure to implant the thermal device 1402. Later, the fluid inlet and outlet conduits can be decoupled from the connector 1402 in a non-surgical or minimally-invasive procedure by simply pulling the conduits through the closed incision.

Figure 15:
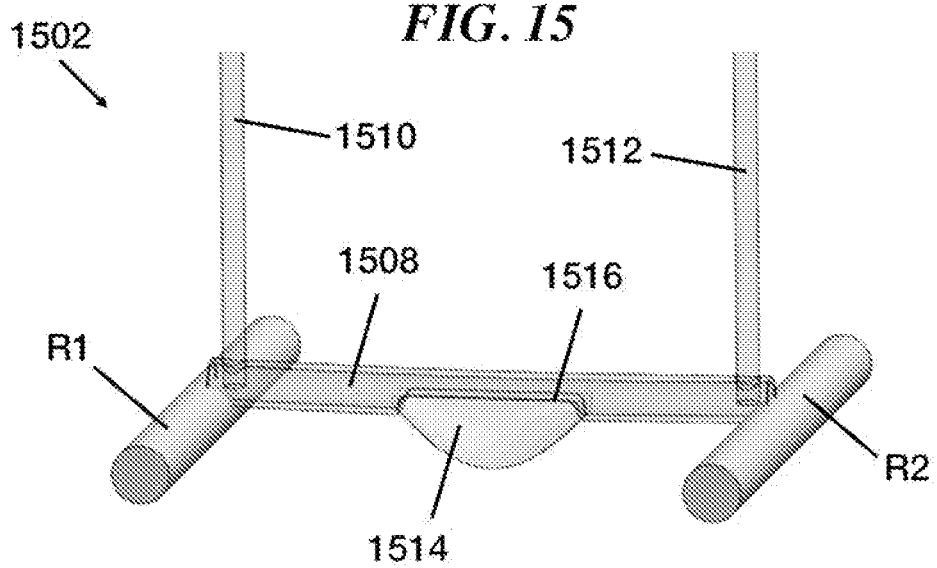
FIG. 15 is a perspective view of a cross-connector thermal device coupled to first and second spinal rods.

FIG. 15 illustrates an exemplary thermal device 1502. Except as indicated below, the structure and operation of the thermal device 1502 is substantially identical to the thermal device 1402, and therefore a detailed description is omitted here for the sake of brevity. The thermal device 1502 includes discrete inlet and outlet conduits 1510, 1512 coupled to the connector 1502 at opposed ends of the chamber 1508 to facilitate directional flow of fluid through the chamber. The thermal device 1502 can also include a balloon or inflatable member 1514 that can be inflated with thermal media circulated through the chamber to bring the inflatable member closer to or into contact with a target treatment site (e.g., the dura of the spinal canal). The connector 1502 can be rigid or semi-rigid and can include a window 1516 through which the inflatable member 1514 can selectively protrude. The inflatable member 1514 can have an inflated configuration in which it protrudes through the window and into close proximity or into contact with the target treatment site. The inflatable member 1514 can also have a deflated configuration in which it does not protrude through the window or protrudes through the window to a lesser degree than when in the inflated configuration. In use, the device 1502 can be coupled to first and second spinal fixation elements R1, R2 to augment a fixation or stabilization construct or to provide physical protection to an exposed spinal canal. Cooled or heated fluid can be circulated through the cavity 1508 of the device to expand the inflatable member 1514 into proximity to or contact with the patient's dura to apply localized thermal therapy thereto. After completion of the thermal therapy, or at any other desired time, the inlet and outlet conduits 1510, 1512 can be separated from the device (e.g., by pulling the conduits proximally) and the connector 1502 can be left in place indefinitely. The inflatable member 1514 can be fixedly attached to at least one of the conduits 1510, 1512 such that pulling out said conduit is effective to also pull the inflatable member out of the device 1502. As described in further detail below, the patient can be closed up with just the inlet and outlet conduits extending through the closed incision, such that thermal therapy can be performed after the surgical procedure to implant the thermal device. Later, the fluid inlet and outlet conduits can be decoupled from the connector in a non-surgical or minimally-invasive procedure by simply pulling the conduits through the closed incision.

Spinous Process Thermal Devices

FIGS. 16A-16D illustrate an exemplary thermal device 1602. The device 1602 can be configured for use as a spinous process spacer or a spinous process fixation device. The device 1602 generally includes first and second opposed plates 1604 separated by a hub or bridge portion 1606 that joins the two plates to form an H-shaped construct. Each plate 1604 can include a superior wing portion 1608 configured for placement against a lateral surface of a spinous process 1610 of a superior vertebra and an inferior wing portion 1612 configured for placement against a lateral surface of a spinous process 1614 of an inferior vertebra. It will be appreciated that the superior and inferior vertebrae need not necessarily be adjacent, and that each plate 1604 can have a length suitable for placing the plate against the spinous processes of non-adjacent vertebrae. The bone-facing surfaces of each plate 1604 can include one or more teeth or other gripping features to engage a spinous process against which the plate is placed. Alternatively, or in addition, the bone-facing surfaces of the plates 1604 can include one or more openings or holes through which screws or other anchors can be inserted to fixedly attach the plate to adjacent bone.

The bridge portion 1606 can include a cavity 1616 formed therein through which heated or chilled fluid can be circulated to apply a thermal effect to the device 1602 and to tissue proximate thereto. For example, as shown in FIG. 16D, the cavity 1616 can be disposed adjacent a patient's spinal canal SC when the device is coupled to superior and inferior spinous processes 1610, 1614. The device 1602 can include inlet and outlet conduits configured to supply and withdraw fluid, respectively, from the cavity 1616. The conduits can be selectively detachable from the device to facilitate post-surgical withdrawal of the conduits. A multi-lumen conduit 1618 that includes an inlet lumen and an outlet lumen can be coupled to the device at a substantial midpoint of the chamber 1616 as shown. Alternatively, or in addition, discrete inlet and outlet conduits can be coupled to the device 1602 at opposed ends of the chamber 1616 to facilitate directional flow of fluid through the chamber.

Figure 16A:
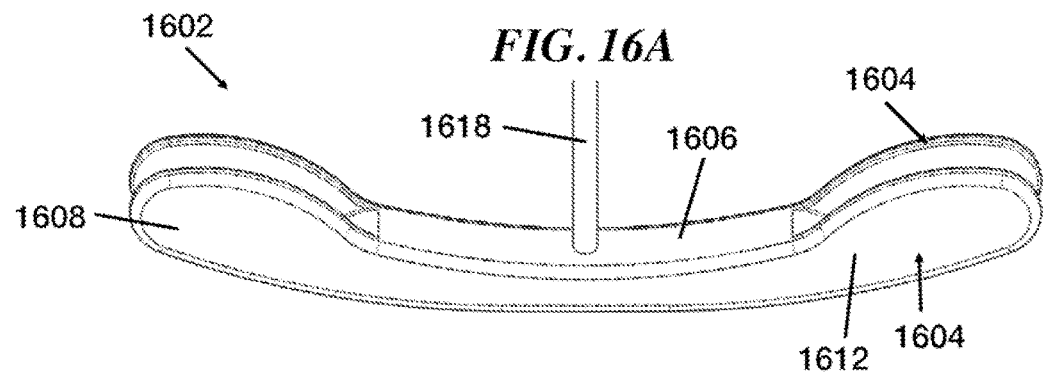
FIG. 16A is a perspective view of a spinous process thermal device.
Figure 16B:
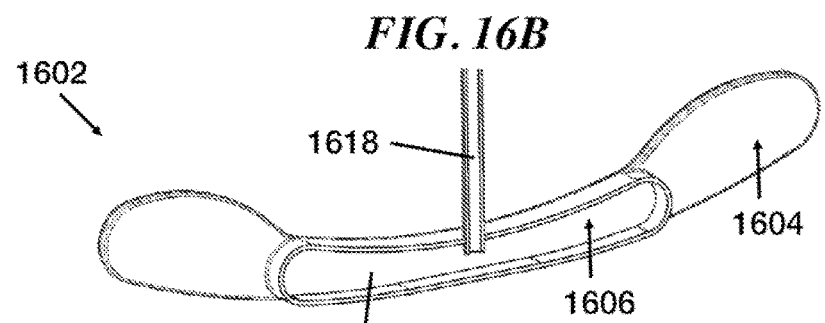
FIG. 16B is a sectional perspective view of the thermal device of FIG. 16A.
Figure 16C:
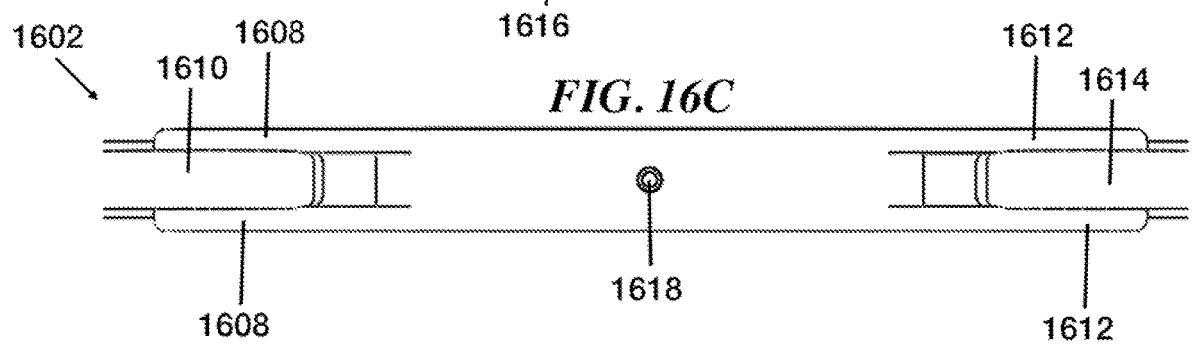
FIG. 16C is a plan view of the thermal device of FIG. 16A and first and second spinous processes.
Figure 16D:
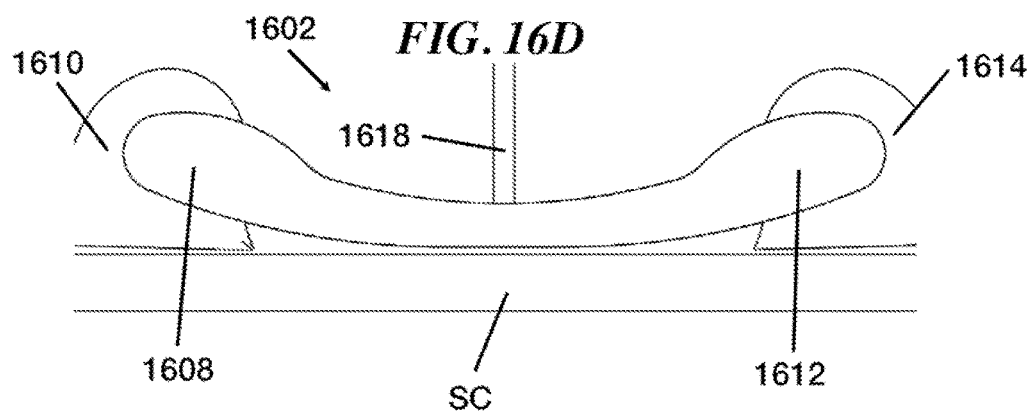
FIG. 16D is a profile view of the thermal device of FIG. 16A, first and second spinous processes, and a spinal canal.

In use, the device 1602 can be coupled to superior and inferior spinous processes 1610, 1614 such that the spinous processes are received between the opposed plates 1604 of the device and the bridge portion 1606 of the device is disposed between the spinous processes, as shown in FIG. 16C. Cooled or heated fluid can be circulated through the cavity 1616 of the device to apply localized thermal therapy to a target treatment region disposed beneath the cavity (e.g., the dura of a patient's spinal canal). After completion of the thermal therapy, or at any other desired time, the inlet and outlet conduits can be separated from the device (e.g., by pulling the conduits proximally) and the device can be left in place indefinitely. As described in further detail below, the patient can be closed up with just the inlet and outlet conduits extending through the closed incision, such that thermal therapy can be performed after the surgical procedure to implant the thermal device. Later, the fluid inlet and outlet conduits can be decoupled from the device in a non-surgical or minimally-invasive procedure by simply pulling the conduits through the closed incision.

Figure 17A:
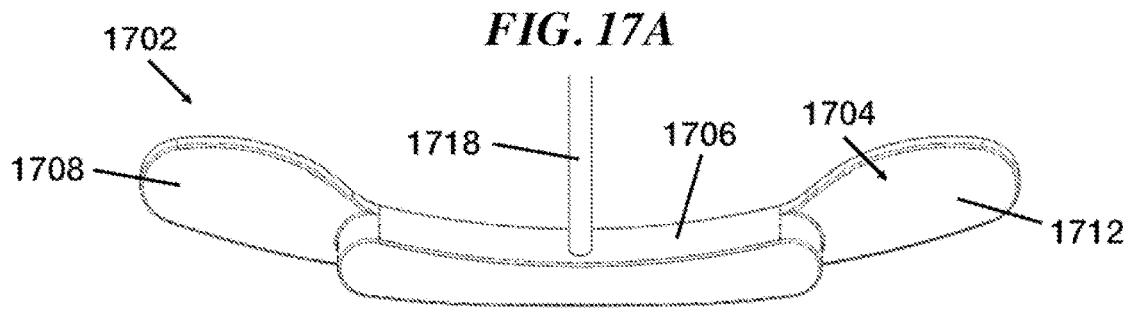
FIG. 17A is a perspective view of a spinous process thermal device.
Figure 17B:
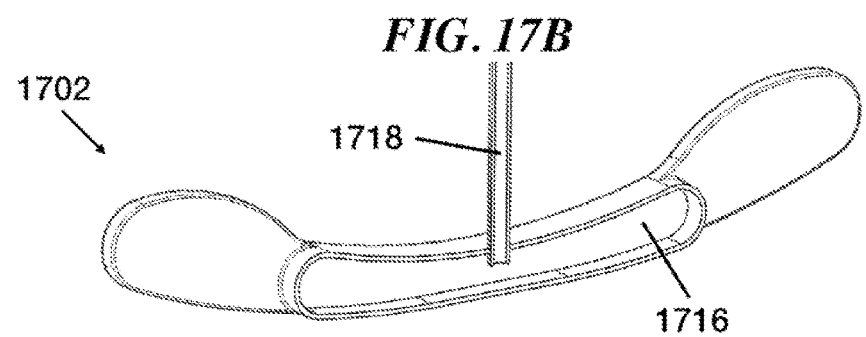
FIG. 17B is a sectional perspective view of the thermal device of FIG. 17A.
Figure 17C:
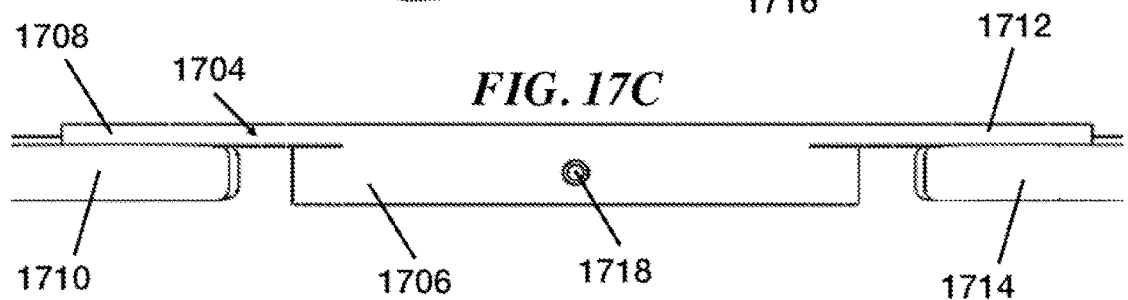
FIG. 17C is a plan view of the thermal device of FIG. 17A, first and second spinous processes, and a spinal canal.
Figure 17D:
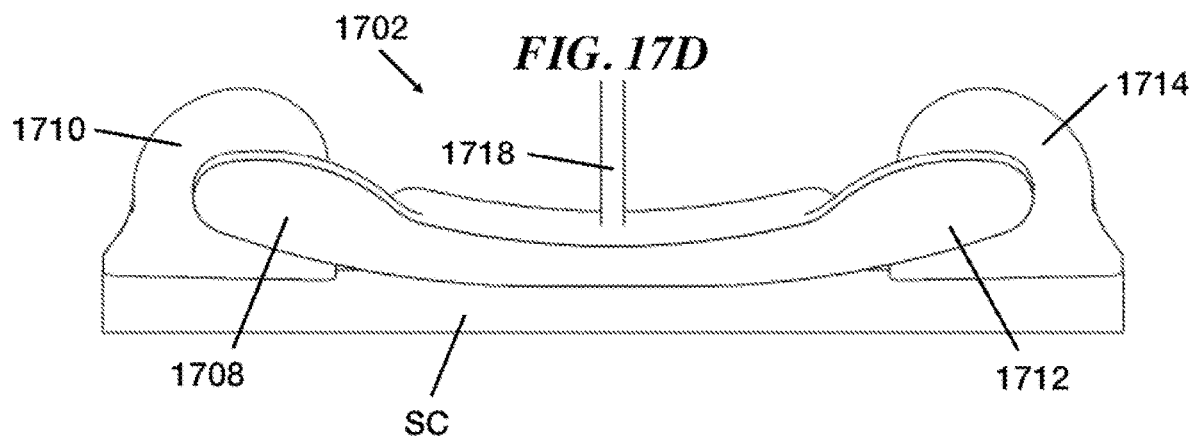
FIG. 17D is a profile view of the thermal device of FIG. 17A and first and second spinous processes.

FIGS. 17A-17D illustrate an exemplary thermal device 1702. Except as indicated below, the structure and operation of the thermal device 1702 is substantially identical to the thermal device 1602, and therefore a detailed description is omitted here for the sake of brevity. In the thermal device 1702, one of the plates can be omitted such that the device includes only a single plate 1704 and the bridge portion 1706. The device 1702 can be coupled to superior and inferior spinous processes 1710, 1714 on only a single side of said spinous processes, as shown in FIG. 17C.

FIGS. 18A-18C illustrate an exemplary thermal device 1802. Except as indicated below, the structure and operation of the thermal device 1802 is substantially identical to the thermal device 1702, and therefore a detailed description is omitted here for the sake of brevity. In the thermal device 1802, the cavity 1816 is not necessarily confined to the bridge portion 1806, but rather can extend into some or all of the plate 1804. While a single plate arrangement is shown, it will be appreciated that the device 1802 can include first and second plates (e.g., as shown and described above with respect to FIGS. 16A-16D) and the cavity 1816 can extend into each of the first and second plates.

Figure 19A:
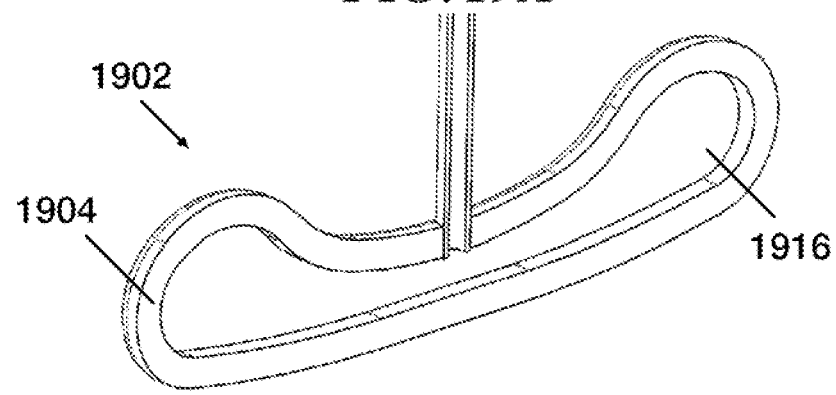
FIG. 19A is a sectional perspective view of a spinous process thermal device.
Figure 19B:
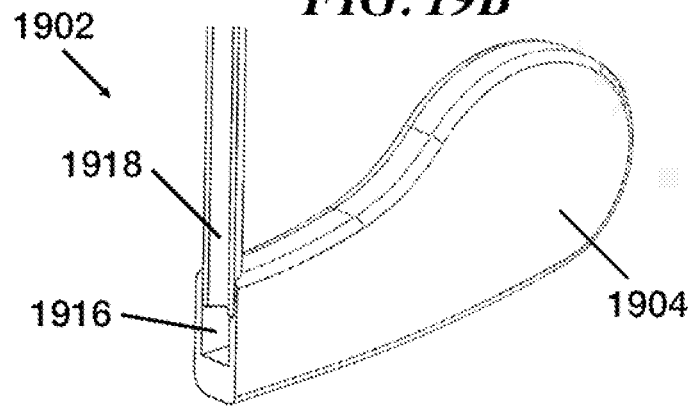
FIG. 19B is another sectional perspective view of the thermal device of FIG. 19A.
Figure 19C:
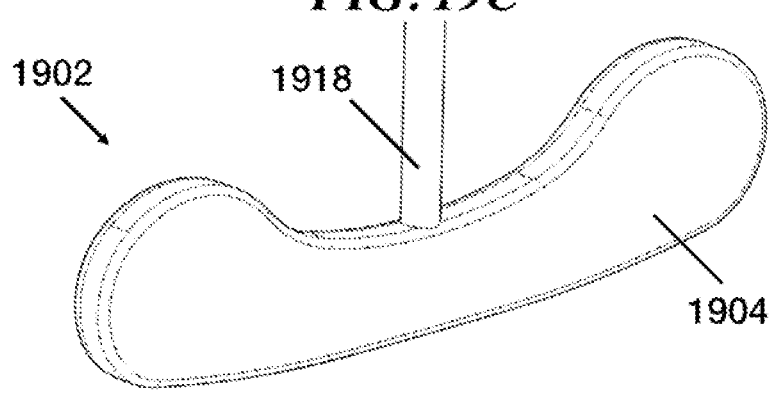
FIG. 19C is a perspective view of the thermal device of FIG. 19A.

FIGS. 19A-19C illustrate an exemplary thermal device 1902. Except as indicated below, the structure and operation of the thermal device 1902 is substantially identical to the thermal device 1802, and therefore a detailed description is omitted here for the sake of brevity. In the thermal device 1902, the bridge portion can be omitted such that the device includes only a single plate portion 1904 in which a cavity 1916 is defined for circulating cooled or heated fluid. The inlet and outlet conduit(s) 1918 can be coupled directly to the plate portion 1904 as shown.

Figure 20A:
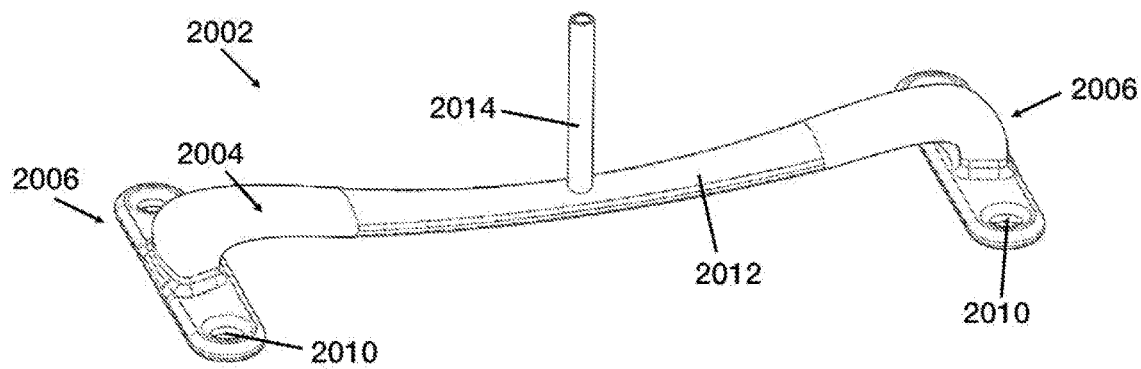
FIG. 20A is a perspective view of a spinal canal shield thermal device.
Figure 20B:
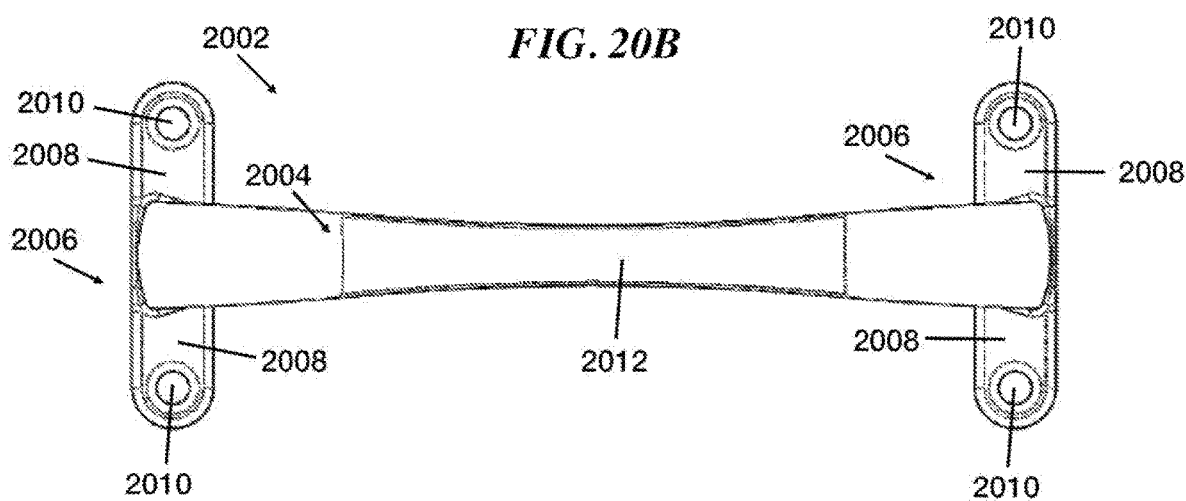
FIG. 20B is a plan view of the thermal device of FIG. 20A.
Figure 20C:
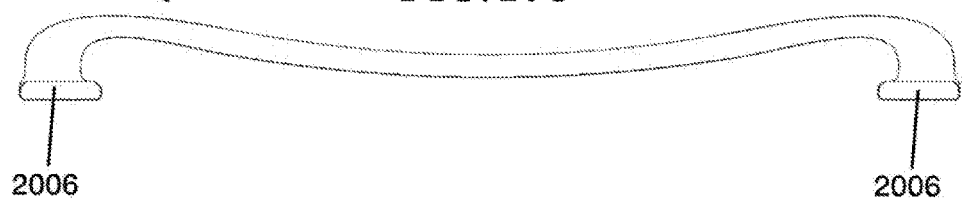
FIG. 20C is a profile view of the thermal device of FIG. 20A.

FIGS. 20A-20C illustrate an exemplary thermal device 2002. The thermal device 2002 generally includes an elongate shield or plate 2004 configured to be positioned over a midline of a patient's spinal canal after one or more spinous processes of the patient's spinal column have been removed. The plate 2004 can be configured to protect the spinal canal contents and to apply localized thermal therapy thereto. The plate 2004 can be positioned such that a central longitudinal axis of the plate is disposed over and substantially in parallel to a midline of a patient's spinal column.

The plate 2004 can include connection features at each end thereof for attaching the plate to the patient's spinal column. In the illustrated embodiment, each end of the plate 2004 includes a flange 2006 that defines first and second lateral wings 2008. An opening 2010 configured to receive a bone screw or other anchoring device can be formed in each of the wings to facilitate attachment of the plate 2004 to bony structures of the spinal column (e.g., pedicles, lateral mass, etc.).

As shown in FIG. 20C, the plate 2004 can curve in one or more planes along a length thereof. For example, as shown, the plate can be bowed such that a central portion of the plate is disposed in close proximity or in contact with the dura of the patient's spinal canal when the plate is attached to the spinal column.

The plate 2004 can include a cavity 2012 formed therein through which heated or chilled fluid can be circulated to apply a thermal effect to the device 2002 and to tissue proximate thereto. For example, the cavity 2012 can be disposed adjacent a patient's spinal canal when the device is coupled to superior and inferior vertebrae of the patient. The device 2002 can include inlet and outlet conduits configured to supply and withdraw fluid, respectively, from the cavity. The conduits can be selectively detachable from the device to facilitate post-surgical withdrawal of the conduits. A multi-lumen conduit 2014 that includes an inlet lumen and an outlet lumen can be coupled to the device at a substantial midpoint of the chamber 2012 as shown. Alternatively, or in addition, discrete inlet and outlet conduits can be coupled to the device at opposed ends of the chamber 2012 to facilitate directional flow of fluid through the chamber.

Figure 20D:
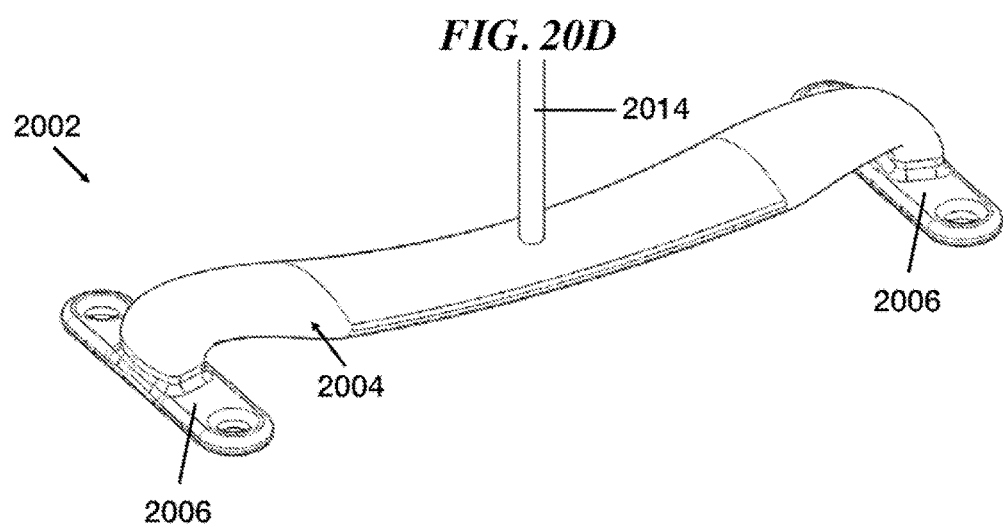
FIG. 20D is a perspective view of a spinal canal shield thermal device.
Figure 20E:
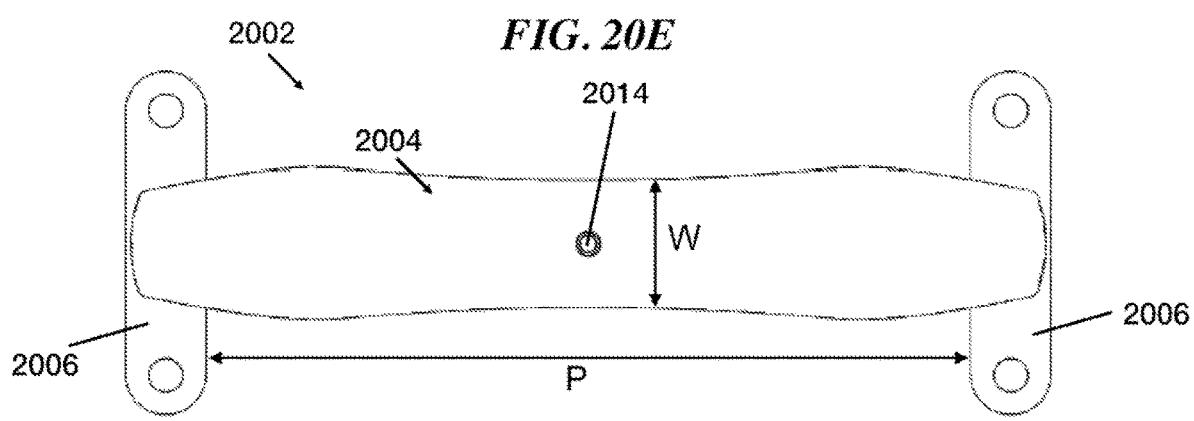
FIG. 20E is a plan view of the thermal device of FIG. 20D.

The plate 2004 can also be made wider to cover a broader area of the patient's spinal canal. A wider version of the plate 2004 is shown in FIGS. 20D-20E. In some embodiments, the portion P of the plate disposed over the spinal canal can have a minimum width W of at least about 15 mm.

In use, the device 2002 can be coupled to superior and inferior vertebrae (e.g., after removal of the spinous processes from the superior and inferior vertebrae and any intervening vertebrae). Cooled or heated fluid can be circulated through the cavity 2012 of the device to apply localized thermal therapy to a target treatment region disposed beneath the cavity (e.g., the dura of a patient's spinal canal). After completion of the thermal therapy, or at any other desired time, the inlet and outlet conduits 2014 can be separated from the device (e.g., by pulling the conduits proximally) and the device 2002 can be left in place indefinitely. As described in further detail below, the patient can be closed up with just the inlet and outlet conduits extending through the closed incision, such that thermal therapy can be performed after the surgical procedure to implant the thermal device. Later, the fluid inlet and outlet conduits can be decoupled from the device in a non-surgical or minimally-invasive procedure by simply pulling the conduits through the closed incision.

Figure 21A:
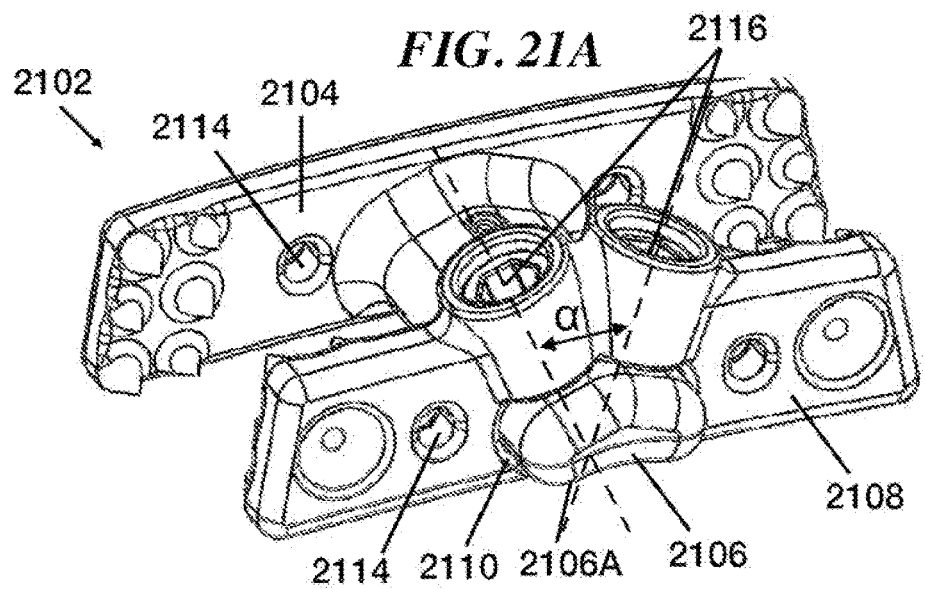
FIG. 21A is a perspective view of a spinous process device.
Figure 21B:
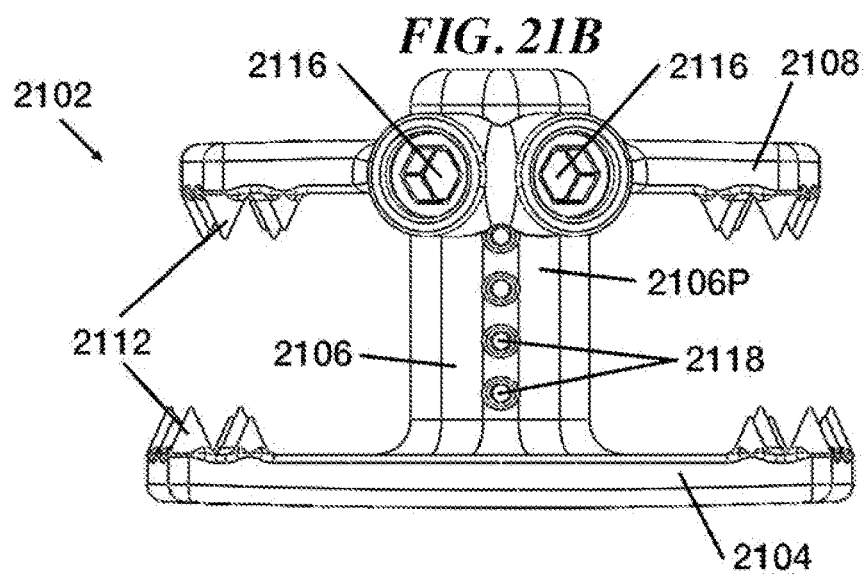
FIG. 21B is a plan view of the device of FIG. 21A.
Figure 21C:
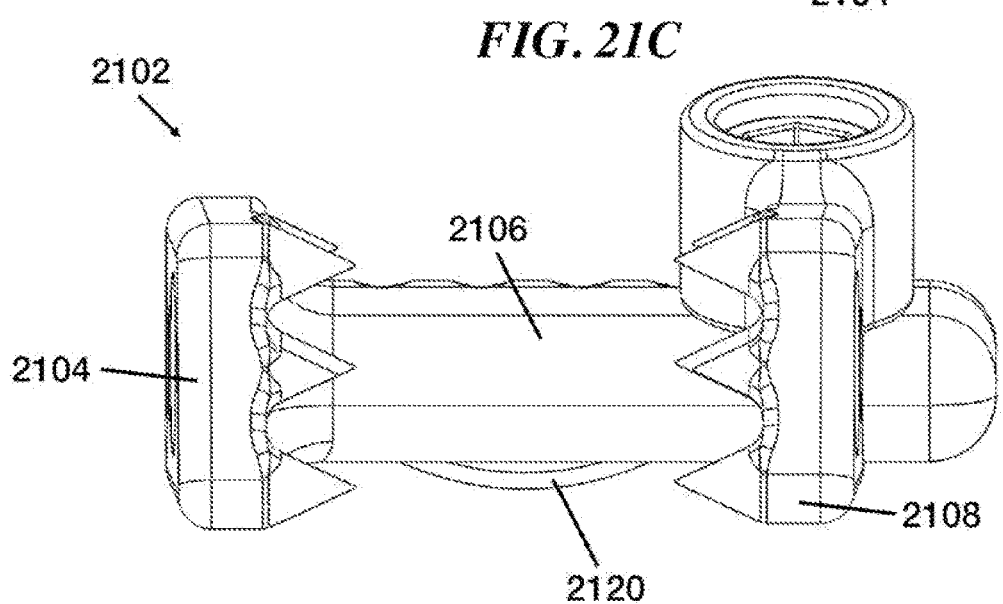
FIG. 21C is a profile view of the device of FIG. 21A.

FIGS. 21A-21C illustrate an exemplary thermal device 2102. The device 2102 can be configured for use as a spinous process spacer or a spinous process fixation device. The device 2102 generally includes a first plate 2104 having a hub or bridge portion 2106 extending therefrom and a second plate 2108 having an opening 2110 in which the bridge portion is slidably received to form an H-shaped construct. The device 2102 can also include one or more locking elements configured to lock a relative position of the second plate 2108 along the bridge portion 2106 or, in other words, to lock a fixed distance between the first and second plates 2104, 2108.

Each plate 2104, 2108 can include a superior wing portion configured for placement against a lateral surface of a spinous process of a superior vertebra and an inferior wing portion configured for placement against a lateral surface of a spinous process of an inferior vertebra. It will be appreciated that the superior and inferior vertebrae need not necessarily be adjacent, and that each plate can have a length suitable for placing the plate against the spinous processes of non-adjacent vertebrae. The bone facing surfaces of each plate can include one or more teeth or other gripping features 2112 to engage a spinous process against which the plate is placed. Alternatively, or in addition, the bone-facing surfaces of the plates can include one or more openings or holes 2114 through which screws or other anchors can be inserted to fixedly attach the plate to adjacent bone.

The bridge portion 2106 can extend perpendicular to the first plate 2104 and can be slidably received within the opening 2110 in the second plate 2108. While the bridge can have any of a variety of cross-sectional shapes, in the illustrated embodiment the bridge includes a concave anterior-facing surface 2106A configured to be disposed over a patient's spinal canal and a convex posterior-facing surface 2106P configured to be engaged by the one or more locking elements.

In the illustrated embodiment, the second plate 2108 includes first and second threaded openings in which first and second set screws 2116 are threadably received. The first and second set screws can be advanced within the openings to engage distal ends of the set screws with the posterior-facing surface 2106P of the bridge 2106, thereby locking a relative position of the second plate 2108 relative to the bridge. The set screws 2116 can be at least partially opposed to one another such that they are advanced towards each other as they are tightened. For example, a longitudinal axis of a first set screw can extend at an oblique angle $\alpha$ with respect to a longitudinal axis of the second set screw. It will be appreciated that, while set screws are shown in the illustrated embodiment, any of a variety of locking elements can be used alternatively or in addition. The use of plural locking elements can advantageously provide redundancy in the event that one of the locking elements becomes loosened or disengaged over time.

Any of the first plate 2104, the second plate 2108, and the bridge portion 2106 can include a cavity formed therein through which heated or chilled fluid can be circulated to apply a thermal effect to the device 2102 and to tissue proximate thereto. For example, the cavity can be formed in the bridge portion 2106 and can be disposed adjacent a patient's spinal canal when the device is coupled to superior and inferior spinous processes. The device 2102 can include inlet and outlet conduits configured to supply and withdraw fluid, respectively, from the cavity. The conduits can be selectively detachable from the device to facilitate post-surgical withdrawal of the conduits. A multi-lumen conduit that includes an inlet lumen and an outlet lumen can be coupled to the device at a substantial midpoint of the chamber. Alternatively, or in addition, discrete inlet and outlet conduits can be coupled to the device at opposed ends of the chamber to facilitate directional flow of fluid through the chamber.

The device 2102 can include one or more sensors 2118 (e.g., temperature probes or sensors) embedded in the plates or the bridge portion, or inserted through said portions. As shown in FIG. 21C, the device 2012 can include a flexible sensor 2120 (e.g., a contact flex thermocouple) configured to flex into contact with or into close proximity to a target area disposed beneath the bridge portion 2106 when the device is implanted in a patient. In some embodiments, sliding the second plate 2108 along the bridge portion 2106 towards the first plate 2104 can be effective to bend the flexible sensor 2120 such that the sensor moves towards a target region disposed beneath the bridge.

In use, the device 2102 can be coupled to superior and inferior spinous processes such that the spinous processes are received between the opposed plates 2104, 2108 of the device and the bridge portion 2106 of the device is disposed between the spinous processes. The plates can be moved towards each other to firmly engage the lateral sides of the spinous processes, and the one or more locking elements 2116 can be actuated to fix the distance between the plates. Once implanted, the device 2102 can be used to monitor one or more physiological parameters (e.g., temperature, pressure, pH, etc.) as localized thermal therapy is performed. Cooled or heated fluid can be circulated through a cavity of the device 2102 to apply localized thermal therapy to a target treatment region disposed beneath the cavity (e.g., the dura of a patient's spinal canal). After completion of the thermal therapy, or at any other desired time, the inlet and outlet conduits can be separated from the device (e.g., by pulling the conduits proximally) and the device can be left in place indefinitely. As described in further detail below, the patient can be closed up with just the inlet and outlet conduits extending through the closed incision, such that thermal therapy can be performed after the surgical procedure to implant the thermal device. Later, the fluid inlet and outlet conduits can be decoupled from the device in a non-surgical or minimally-invasive procedure by simply pulling the conduits through the closed incision.

Rod Thermal Devices

Figure 22A:
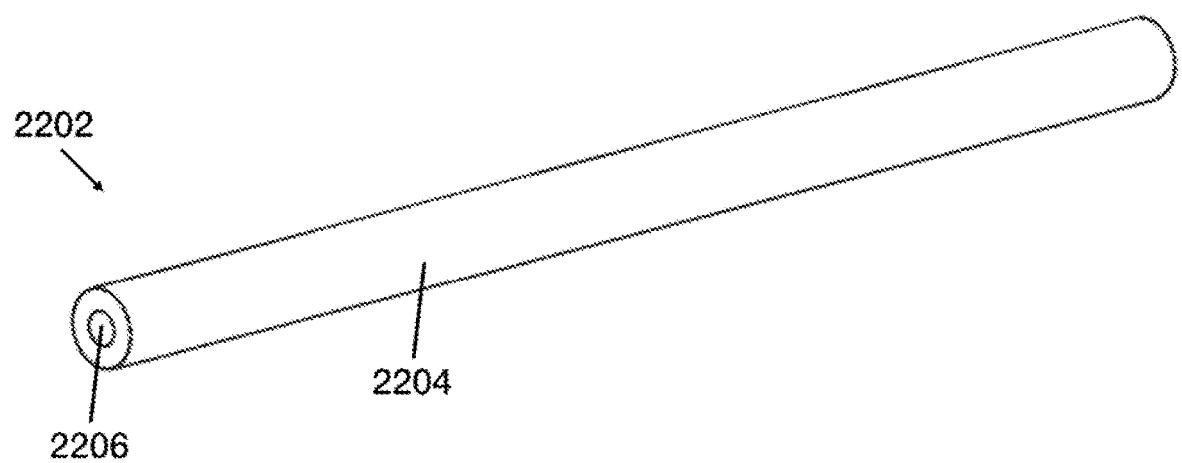
FIG. 22A is a perspective view of a spinal rod thermal device.
Figure 22B:
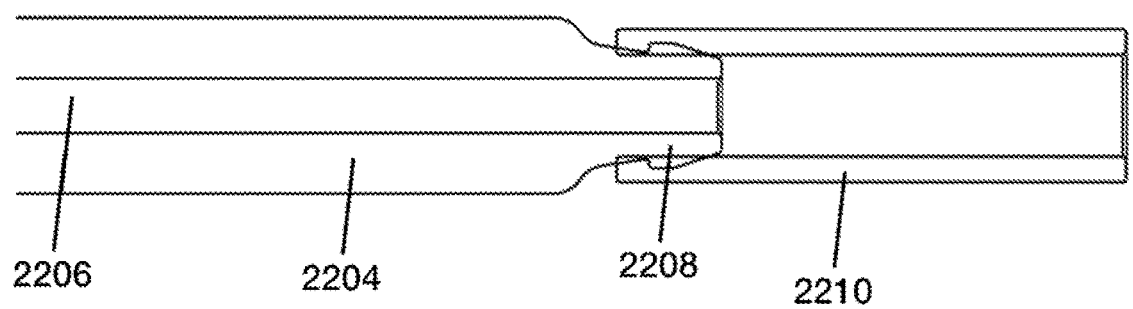
FIG. 22B is a sectional profile view of a barbed coupling and the thermal device of FIG. 22A.
Figure 22C:
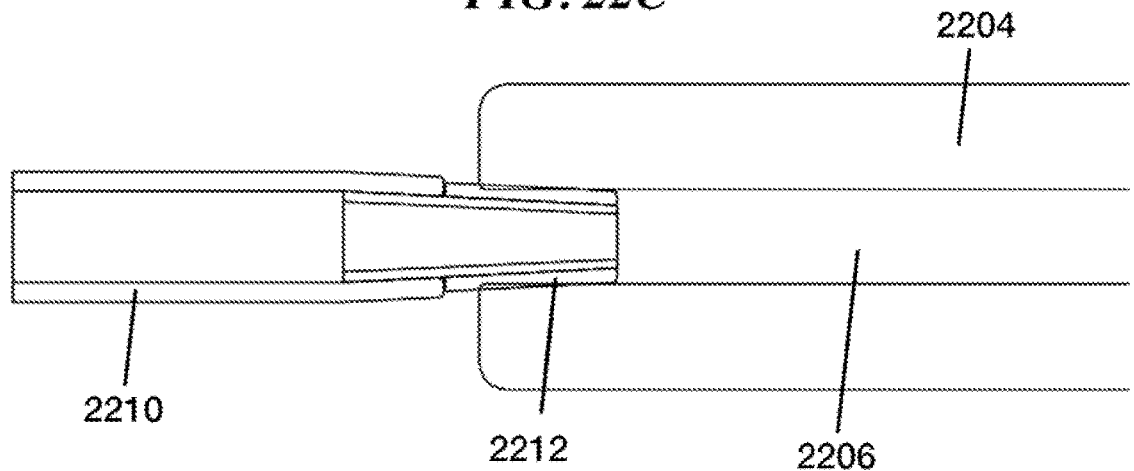
FIG. 22C is a sectional profile view of a tapered fitting and the thermal device of FIG. 22A.

FIGS. 22A-22C illustrate an exemplary thermal device 2202. The device 2202 can be configured for use as a spinal fixation or stabilization rod. The device 2202 generally includes an elongate rod 2204 having a cannulation 2206 formed along at least a portion of the length of the rod. The cannulation can define a cavity through which heated or chilled fluid can be circulated to apply a thermal effect to the device and to tissue proximate thereto. The device 2202 can include inlet and outlet conduits configured to supply and withdraw fluid, respectively, from the cannulation. The conduits can be selectively detachable from the device to facilitate post-surgical withdrawal of the conduits. A multi-lumen conduit that includes an inlet lumen and an outlet lumen can be coupled to the device at one end of the cannulation and the opposite end of the cannulation can be closed. Alternatively, discrete inlet and outlet conduits can be coupled to the device at opposed ends of the cannulation to facilitate directional flow of fluid through the device. As shown in FIG. 22B, the inlet and/or outlet conduits 2210 can be coupled to the rod using a barbed fitting 2208 formed on or coupled to an end of the rod 2204 to form a fluid tight connection and place the cannulation 2206 of the thermal device in fluid communication with the inlet and/or outlet conduit. While the barbed fitting 2208 is shown as part of the rod 2204, it will be appreciated that the fitting can be formed on the conduit 2210 instead and can be received within the cannulation 2206 of the rod. As shown in FIG. 22C, the inlet and/or outlet conduits 2210 can be coupled to the rod 2204 using a tapered fitting 2212 to form a fluid tight connection and place the cannulation 2206 of the thermal device in fluid communication with the inlet and/or outlet conduit. The fitting 2212 can include an inner tapered portion formed from a first material (e.g., steel) and an outer tubular portion formed from a second material that is different from the first material (e.g., plastics, elastomers, etc.). While the tapered fitting is shown as being inserted into the cannulation 2206 of the rod 2204, it will be appreciated that this can be reversed such that the fitting is formed on or coupled to the rod and inserted into the interior of the conduit 2210. A threaded connection can also be used to couple the conduit (s) to the thermal device 2202. The fittings of FIGS. 22B and 22C can also be used to couple with various other devices other than spinal rods.

Figure 23A:
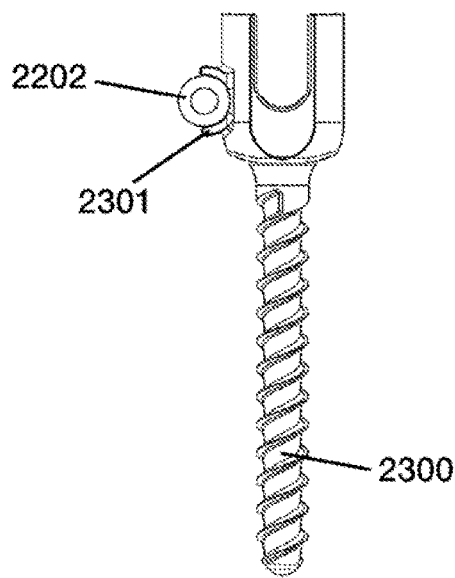
FIG. 23A is a profile view of a spinal rod thermal device coupled to a bone anchor outrigger.
Figure 23B:
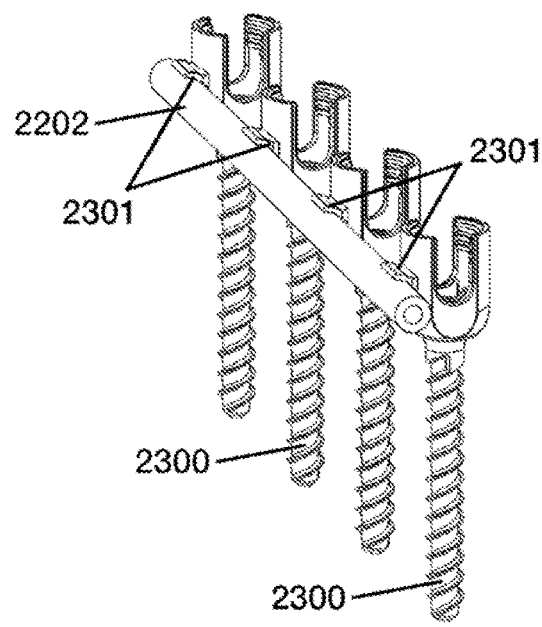
FIG. 23B is a perspective view of the thermal device of FIG. 23A coupled to a plurality of bone anchor outriggers.

In use, the device 2202 can be anchored to the spine using one or more bone anchors (e.g., first and second bone screws). For example, the device 2202 can be seated in the U-shaped recesses of a plurality of bone screws and secured thereto using set screws. By way of further example, the device 2202 can be seated in side-entry outriggers of a plurality of bone anchors 2300, as shown in FIGS. 23A and 23B. The outriggers 2301 can include opposed arms that define a rod-receiving recess, the opposed arms extending substantially perpendicular to the arms that define the primary U-shaped recess in the bone anchor. The outriggers 2301 can be configured to receive the thermal device 2202 in a snap-fit or press-fit engagement. The thermal device 2202 can also be coupled to the outriggers by a locking mechanism such as a set screw or locking nut. In some embodiments, a first thermal device can be seated in the U-shaped recesses of the bone anchors and a second thermal device can be seated in the outriggers. In other embodiments, a traditional spinal rod can be seated in the U-shaped recesses of the bone anchors and the thermal device can be seated in the outriggers. Cooled or heated fluid can be circulated through the cannulation of the device to apply localized thermal therapy to a target treatment region disposed in proximity to the device or to bone anchors to which the device is coupled. After completion of the thermal therapy, or at any other desired time, the inlet and outlet conduits can be separated from the device (e.g., by pulling the conduits proximally) and the device can be left in place indefinitely. As described in further detail below, the patient can be closed up with just the inlet and outlet conduits extending through the closed incision, such that thermal therapy can be performed after the surgical procedure to implant the thermal device. Later, the fluid inlet and outlet conduits can be decoupled from the device in a non-surgical or minimally-invasive procedure by simply pulling the conduits through the closed incision.

Instrument Thermal Devices

Figure 24:
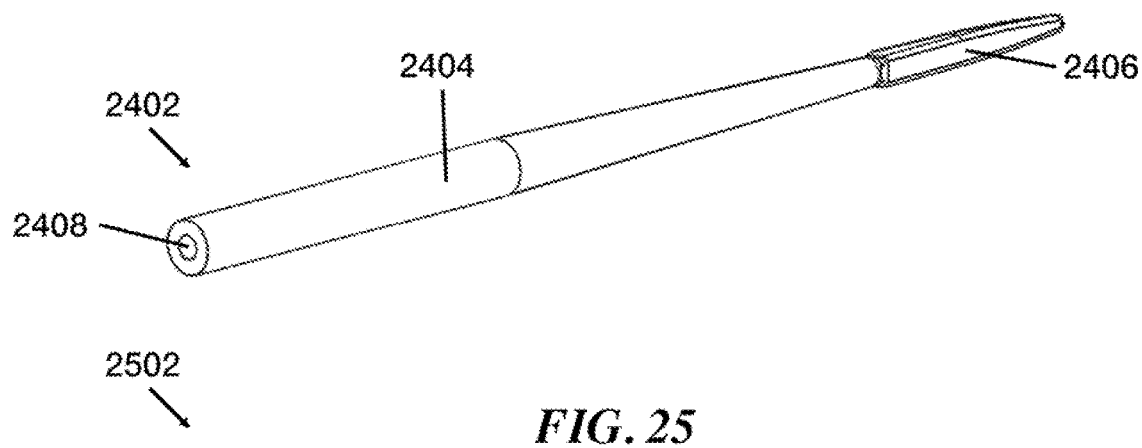
FIG. 24 is a perspective view of a probe thermal device.

FIG. 24 illustrates an exemplary thermal device 2402. The device 2402 can be configured for use as a pedicle marker or probe. The device 2402 generally includes an elongate shaft 2404 having a tapered distal end 2406. The shaft 2404 can include a cannulation 2408 formed along at least a portion of the length of the shaft. The cannulation 2408 can define a cavity through which heated or chilled fluid can be circulated to apply a thermal effect to the device 2402 and to tissue proximate thereto. The device 2402 can include inlet and outlet conduits configured to supply and withdraw fluid, respectively, from the cannulation. The conduits can be selectively detachable from the device to facilitate post-surgical withdrawal of the conduits. A multi-lumen conduit that includes an inlet lumen and an outlet lumen can be coupled to the device at a proximal end of the cannulation and the distal end of the cannulation can be closed.

In use, the device 2402 can be used as a pedicle marker or probe. A hole can be drilled into a bony structure of the patient and the tapered distal tip 2406 of the thermal device 2402 can be inserted into the hole. Cooled or heated fluid can be circulated through the cannulation 2408 of the device to apply localized thermal therapy to the bone in which the hole is formed and tissue proximate thereto. After completion of the thermal therapy, or at any other desired time, the inlet and outlet conduits can be separated from the device (e.g., by pulling the conduits proximally).

Figure 25:
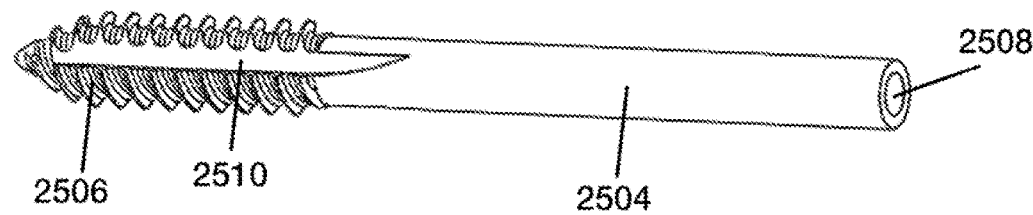
FIG. 25 is a perspective view of a drill or tap thermal device.

FIG. 25 illustrates an exemplary thermal device 2502. The device 2502 can be configured for use as bone tap or drill bit. The device 2502 generally includes an elongate shaft 2504 having a threaded or bladed distal end 2506. The distal end can include one or more flutes 2510 to facilitate self-tapping of a bone hole using the device. The shaft 2504 can include a cannulation 2508 formed along at least a portion of the length of the shaft. The cannulation 2508 can define a cavity through which heated or chilled fluid can be circulated to apply a thermal effect to the device 2502 and to tissue proximate thereto. The device 2502 can include inlet and outlet conduits configured to supply and withdraw fluid, respectively, from the cannulation. The conduits can be selectively detachable from the device to facilitate post-surgical withdrawal of the conduits. A multi-lumen conduit that includes an inlet lumen and an outlet lumen can be coupled to the device at a proximal end of the cannulation and the distal end of the cannulation can be closed.

In use, the device 2502 can be used as a bone tap or drill bit for forming a hole in a bony structure of the patient. Before, during, or after advancing the device 2502 into bone, cooled or heated fluid can be circulated through the cannulation 2508 of the device to apply localized thermal therapy to the bone and tissue proximate thereto. After completion of the thermal therapy, or at any other desired time, the inlet and outlet conduits can be separated from the device 2502 (e.g., by pulling the conduits proximally).

Bone Plug and Bone Plate Thermal Devices

Figure 26A:
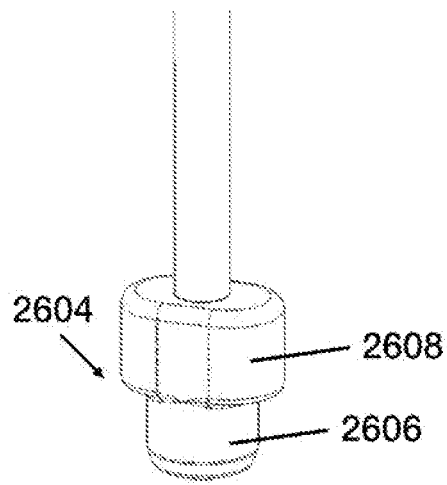
FIG. 26A is a perspective view of a bone plug thermal device.
Figure 26B:
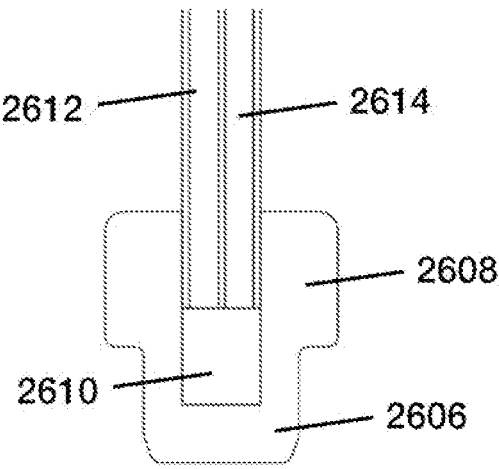
FIG. 26B is a sectional profile view of the thermal device of FIG. 26A.

FIGS. 26A-26B illustrate an exemplary thermal device 2602. The thermal device 2602 generally includes a bone plug 2604 configured to be inserted into a hole formed in a bone structure of a patient to apply localized thermal therapy thereto. The plug 2604 can include a cylindrical distal projection 2606 sized and configured to be received in a bone hole. In some embodiments, the cylindrical distal projection 2606 can be non-threaded. The plug 2604 can also include a proximal body portion 2608 to facilitate grasping and manipulation of the plug.

The plug 2604 can include a cavity 2610 formed therein through which heated or chilled fluid can be circulated to apply a thermal effect to the device 2602 and to tissue proximate thereto. The device 2602 can include inlet and outlet conduits 2612, 2614 configured to supply and withdraw fluid, respectively, from the cavity 2610. The conduits can be selectively detachable from the device to facilitate post-surgical withdrawal of the conduits. A multi-lumen conduit that includes an inlet lumen and an outlet lumen can be coupled to a proximal end of the device as shown. Alternatively, or in addition, discrete inlet and outlet conduits can be coupled to the device.

In use, a bone structure of a patient can be prepared by forming a drill hole (e.g., a blind bore) in the bone. Exemplary bone structures include a vertebra, a vertebral body, a lamina, a spinous process, a lateral mass, a pedicle, and any other bone in a human or animal body. The distal projection 2606 of the device 2602 can then be inserted into the bone hole. The bone hole can be sized such that a slight interference fit is formed between the plug 2604 and bone hole to help maintain the plug in position within the bone hole. Cooled or heated fluid can be circulated through the cavity 2610 of the device 2602 to apply localized thermal therapy to the bone in which the bone hole is formed and to tissue proximate thereto. After completion of the thermal therapy, or at any other desired time, the inlet and outlet conduits can be separated from the device (e.g., by pulling the conduits proximally) and the device can be left in place indefinitely. Alternatively, the device can be removed with the inlet and outlet conduits. As described in further detail below, the patient can be closed up with just the inlet and outlet conduits extending through the closed incision, such that thermal therapy can be performed after the surgical procedure to implant the thermal device. Later, the fluid inlet and outlet conduits can be decoupled from the device in a non-surgical or minimally-invasive procedure by simply pulling the conduits through the closed incision. Alternatively, the fluid inlet and outlet conduits and the bone plug itself can be removed together in a non-surgical or minimally-invasive procedure by simply pulling the conduits and the bone plug through the closed incision.

Figure 27A:
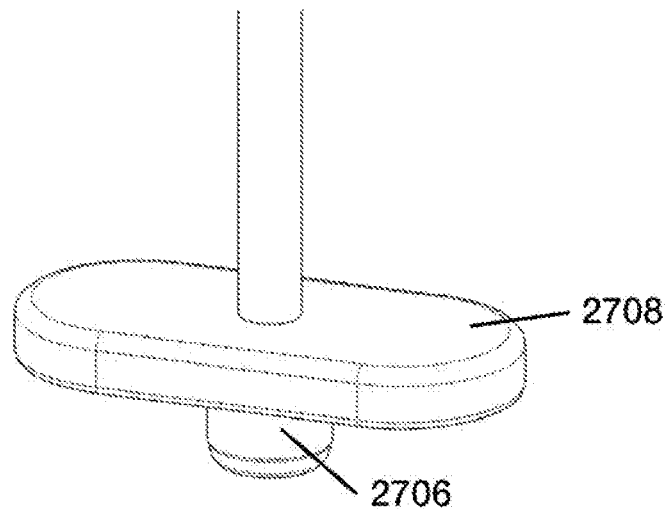
FIG. 27A is a perspective view of a bone plug and plate thermal device.
Figure 27B:
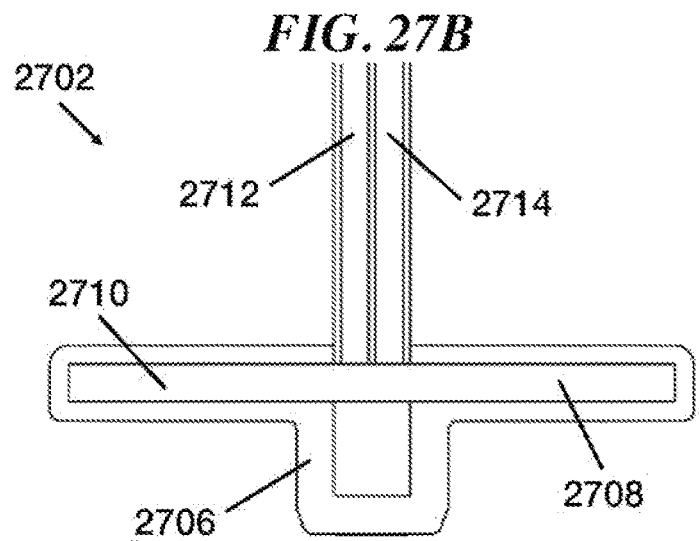
FIG. 27B is a sectional profile view of the thermal device of FIG. 27A.

FIGS. 27A-27B illustrate an exemplary thermal device 2702. Except as indicated below, the structure and operation of the thermal device 2702 is substantially identical to the thermal device 2602, and therefore a detailed description is omitted here for the sake of brevity. In the thermal device 2702, the proximal body portion 2708 can be in the form of an enlarged plate configured to lie against the bone structure in which the bone hole is formed when the distal projection 2706 of the thermal device 2702 is seated in the bone hole. As shown in FIG. 27B, the cavity 2710 can extend into the distal projection of the plug as well as laterally throughout the plate portion 2708 of the plug. The thermal device 2702 can advantageously provide a broader application of localized thermal therapy given the increased contact surface area provided by the plate portion 2708.

Figure 28A:
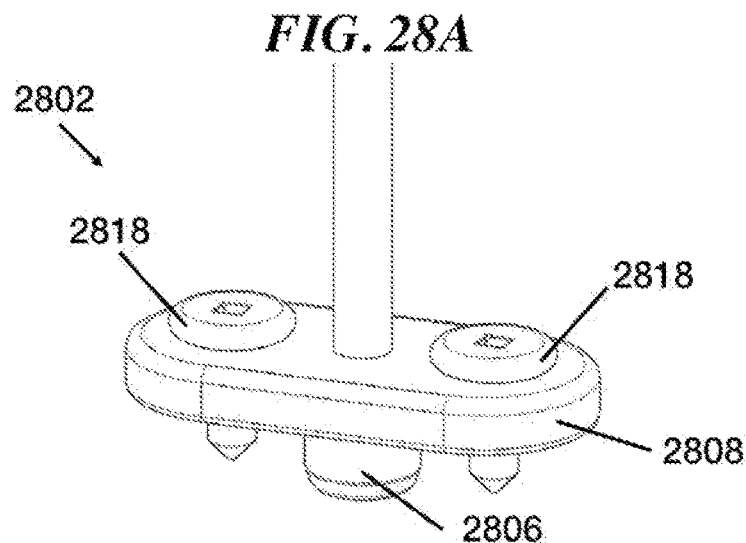
FIG. 28A is a perspective view of a bone plug and plate with bone anchors thermal device.
Figure 28B:
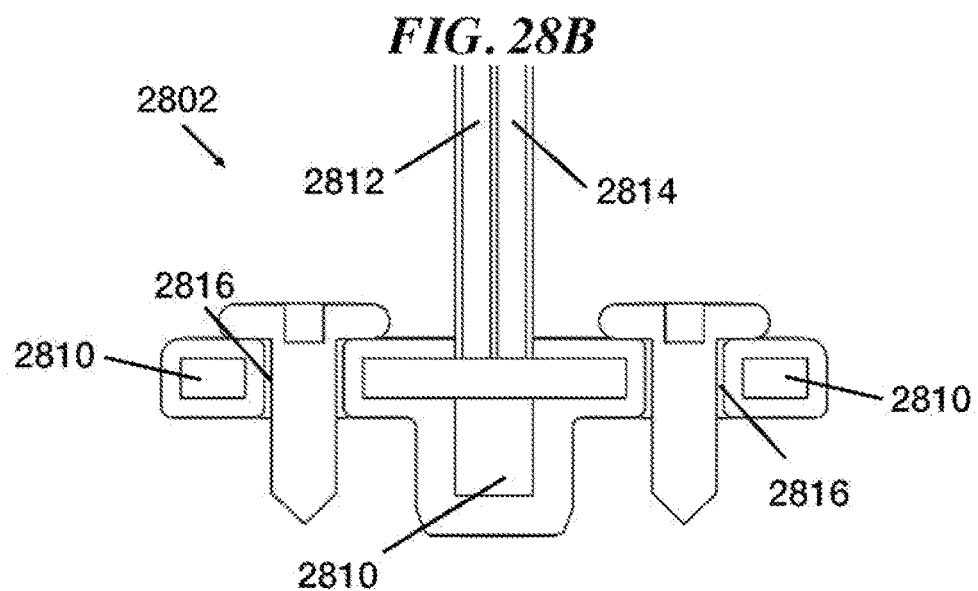
FIG. 28B is a sectional profile view of the thermal device of FIG. 28A.

FIGS. 28A-28B illustrate an exemplary thermal device 2802. Except as indicated below, the structure and operation of the thermal device 2802 is substantially identical to the thermal device 2702, and therefore a detailed description is omitted here for the sake of brevity. In the thermal device 2802, the proximal plate portion 2808 includes one or more openings 2816 formed therein configured to receive a bone anchor 2818 (e.g., a bone screw) to secure the plate to bone. As shown in FIG. 28B, the openings 2816 can define tunnels that extend through the fluid cavity 2810, such that the cavity extends around the openings. The thermal device 2802 can advantageously provide a more secure attachment to bone.

Figure 29A:
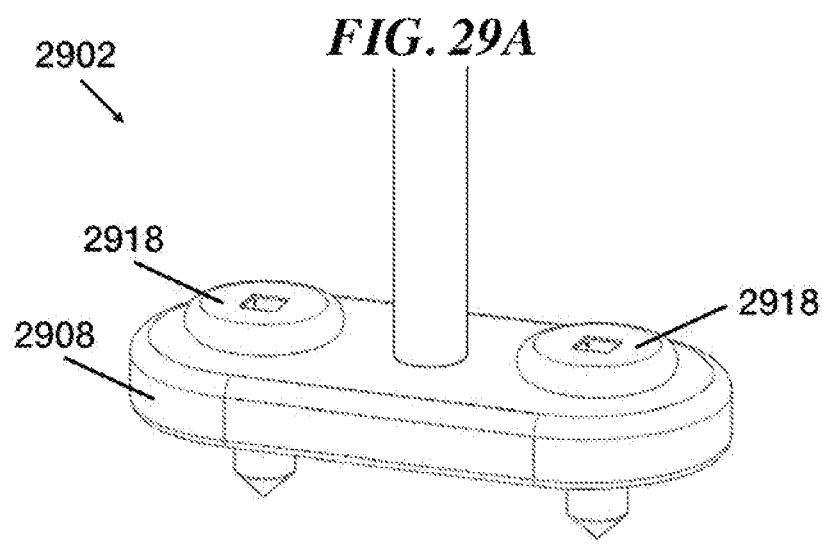
FIG. 29A is a perspective view of a bone plate thermal device.
Figure 29B:
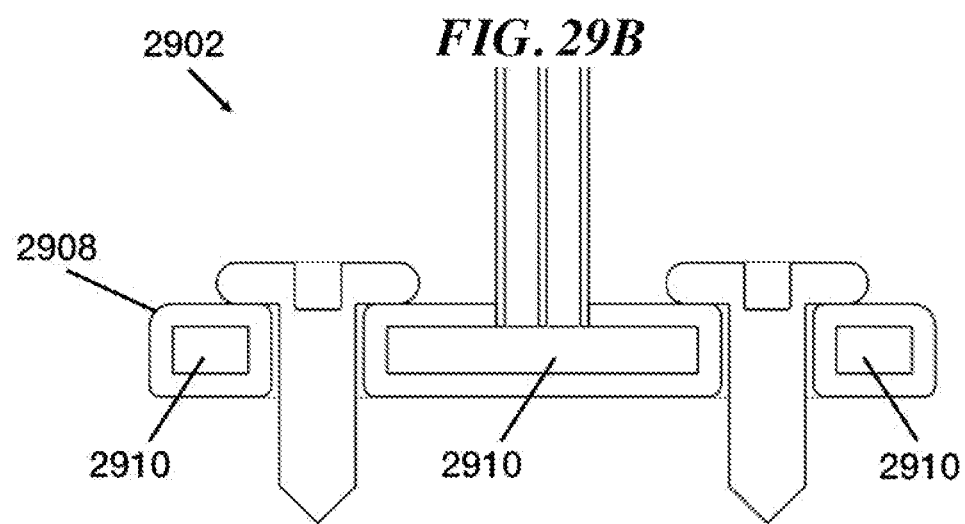
FIG. 29B is a sectional profile view of the thermal device of FIG. 29A.

FIGS. 29A-29B illustrate an exemplary thermal device 2902. Except as indicated below, the structure and operation of the thermal device 2902 is substantially identical to the thermal device 2802, and therefore a detailed description is omitted here for the sake of brevity. In the thermal device 2902, the distal projection of the device is omitted such that the body of the device includes only the proximal plate portion 2908. The thermal device 2902 can advantageously be used without the need to first form a bone hole to receive a plug portion of the device.

Figure 30A:
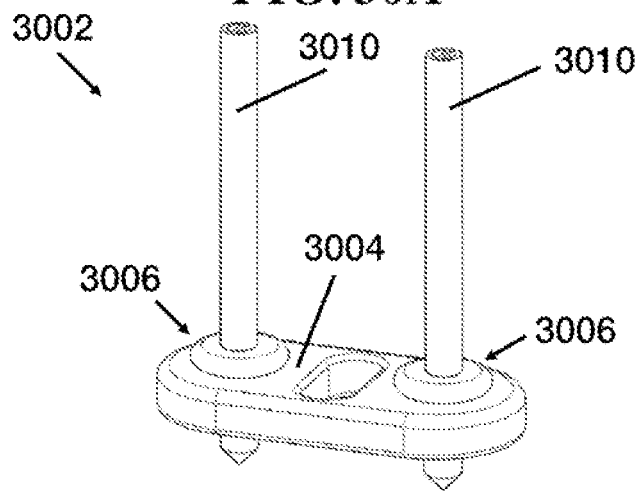
FIG. 30A is a perspective view of a bone plate with bone anchor thermal devices.
Figure 30B:
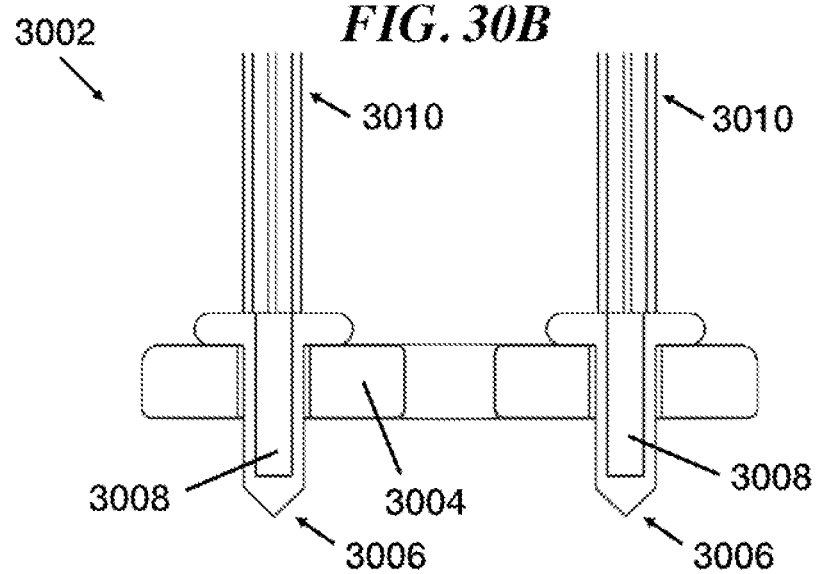
FIG. 30B is a sectional profile view of the thermal device of FIG. 30A.

FIGS. 30A-30B illustrate an exemplary thermal device 3002. The thermal device 3002 generally includes a bone plate 3004 and one or more bone anchor thermal devices 3006 (e.g., of the type described above). The bone plate 3004 can include one or more openings through which the bone anchor thermal devices 3006 can be inserted to couple the bone plate to a bone structure of a patient. Each of the bone anchor thermal devices 3006 can include a cavity 3008 formed therein through which heated or chilled fluid can be circulated to apply a thermal effect to the bone anchor, the plate, and to tissue proximate thereto. The bone anchor thermal devices 3006 can include inlet and outlet conduits configured to supply and withdraw fluid, respectively, from the cavity. The conduits can be selectively detachable from the bone anchors to facilitate post-surgical withdrawal of the conduits. A multi-lumen conduit 3010 that includes an inlet lumen and an outlet lumen can be coupled to a proximal end of the bone anchor 3006 as shown. Alternatively, or in addition, discrete inlet and outlet conduits can be coupled to the bone anchor 3006.

In use, the plate 3004 can be secured to a bone structure of a patient by inserting the bone anchor thermal devices 3006 through the openings in the plate and anchoring the bone anchors in the bone. Exemplary bone structures include a vertebra, a vertebral body, a lamina, a spinous process, a lateral mass, a pedicle, and any other bone in a human or animal body. Cooled or heated fluid can be circulated through the cavities 3008 of the one or more bone anchor thermal devices 3006 to apply localized thermal therapy to the plate 3004 and the bone to which the plate is coupled. After completion of the thermal therapy, or at any other desired time, the inlet and outlet conduits 3010 can be separated from the bone anchors 3006 (e.g., by pulling the conduits proximally) and the bone anchors and the plate 3004 can be left in place indefinitely. As described in further detail below, the patient can be closed up with just the inlet and outlet conduits extending through the closed incision, such that thermal therapy can be performed after the surgical procedure to implant the thermal device. Later, the fluid inlet and outlet conduits can be decoupled from the device in a non-surgical or minimally-invasive procedure by simply pulling the conduits through the closed incision.

Clamp Thermal Devices

Figure 31A:
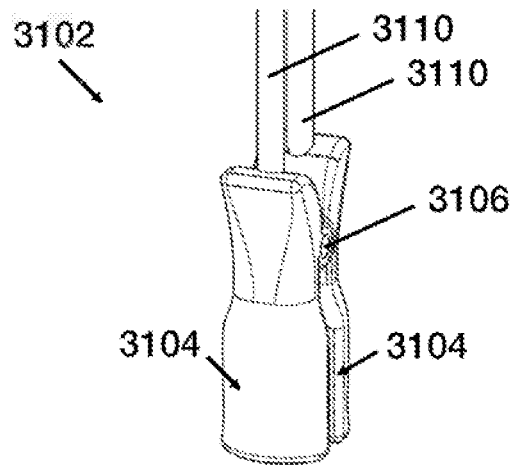
FIG. 31A is a perspective view of a clamp thermal device.
Figure 31B:
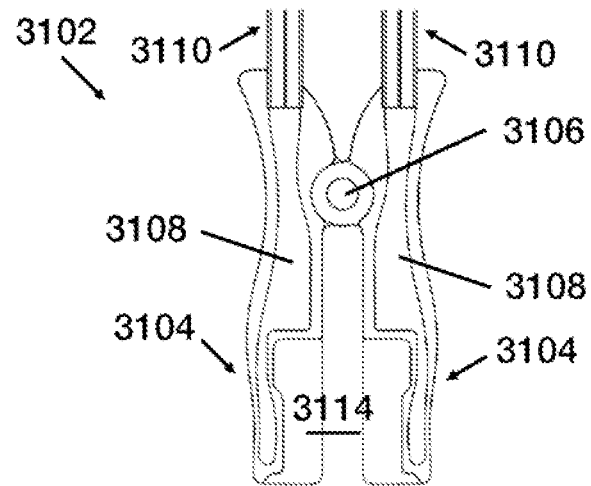
FIG. 31B is a sectional profile view of the thermal device of FIG. 31A.
Figure 31C:
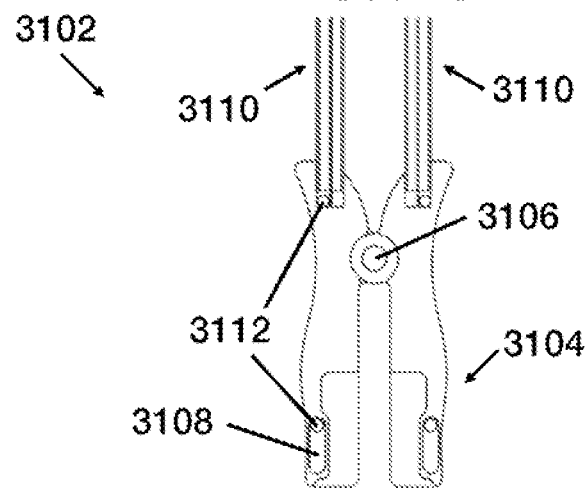
FIG. 31C is a sectional profile view of a clamp thermal device.

FIGS. 31A-31C illustrate an exemplary thermal device 3102. The thermal device 3102 generally includes a clamp configured to grasp an implant or an anatomical structure to apply localized thermal therapy thereto. The device 3102 can include first and second opposed clamping arms 3104 pivotally coupled to one another at a hinge 3106. The hinge 3106 can be or can include a pivot pin, a living hinge, or any of a variety of other mechanisms for pivotally coupling the first and second clamping arms 3104 to one another.

One or both of the first and second clamping arms 3104 can include a cavity 3108 formed therein through which heated or chilled fluid can be circulated to apply a thermal effect to the device 3102 and to an implant or anatomical structure grasped thereby. The device 3102 can include inlet and outlet conduits 3110 configured to supply and withdraw fluid, respectively, from each cavity 3108. The conduits 3110 can be selectively detachable from the device to facilitate post-surgical withdrawal of the conduits. A multi-lumen conduit 3110 that includes an inlet lumen and an outlet lumen can be coupled to a proximal end of each of the opposed arms 3104 as shown. Alternatively, or in addition, discrete inlet and outlet conduits can be coupled to each arm.

The cavity 3108 of each arm 3104 can extend through and fill substantially the entire internal volume of the arm as shown in FIG. 31B. Alternatively, the cavity 3108 can formed entirely in a distal portion of the arm 3104, with only a relatively small fluid passage 3112 extending through the proximal portion of the arm to provide fluid communication between the cavity and the fluid inlet and outlet conduits 3110. This can advantageously focus the thermal effect at the distal end of the device 3102 where the clamped object is disposed.

The opposed arms 3104 can define a clamping recess 3114 that is substantially a negative of a structure to which the device 3102 is to be clamped. For example, the clamping recess 3114 can be substantially a negative of the head of a bone screw, a spinal rod, a spinous process spacer, an interbody spacer, etc. By way of further example, the clamping recess 3114 can be substantially a negative of an anatomical structure such as a spinous process, a facet, a lateral mass, a pedicle, a lamina, etc.

In use, the device 3102 can be clamped onto an implant or an anatomical structure of a patient. When the anatomical structure is a bone, the bone can be prepared for delivery of thermal therapy, for example by removing any soft tissue overlying the bone and/or decorticating the bone. Exemplary bone structures include a vertebra, a vertebral body, a lamina, a spinous process, a lateral mass, a pedicle, and any other bone in a human or animal body. Cooled or heated fluid can be circulated through one or more cavities 3108 of the device 3102 to apply localized thermal therapy to the object which is grasped by the device and to tissue proximate thereto. Delivering a thermal effect through both of the clamping arms can advantageously provide more uniform application of the thermal effect to the object grasped by the device. After completion of the thermal therapy, or at any other desired time, the inlet and outlet conduits 3110 can be separated from the device (e.g., by pulling the conduits proximally) and the device 3102 can be left in place indefinitely. Alternatively, the device can be removed with the inlet and outlet conduits. As described in further detail below, the patient can be closed up with just the inlet and outlet conduits extending through the closed incision, such that thermal therapy can be performed after the surgical procedure to implant the thermal device. Later, the fluid inlet and outlet conduits can be decoupled from the device in a non-surgical or minimally-invasive procedure by simply pulling the conduits through the closed incision.

Interbody Thermal Devices

Figure 32A:
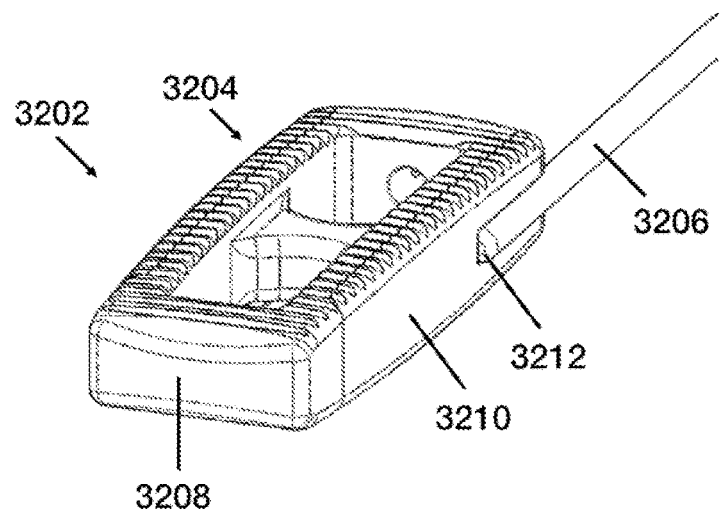
FIG. 32A is a perspective view of an interbody thermal device.
Figure 32B:
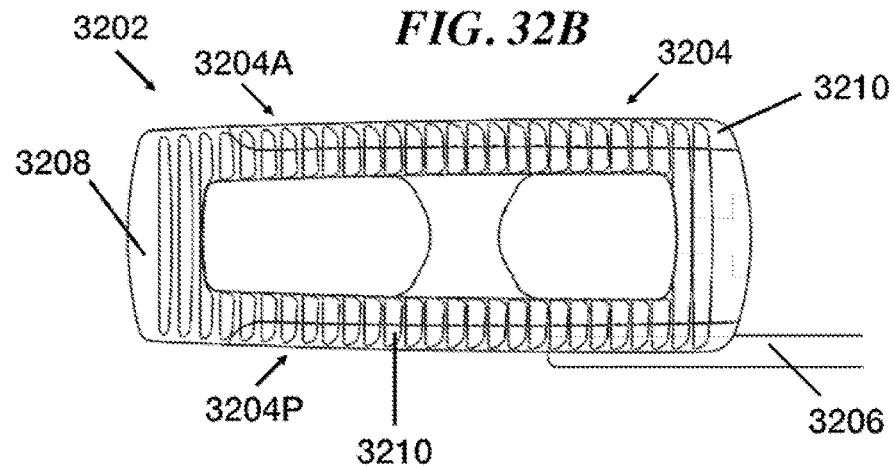
FIG. 32B is a plan view of the thermal device of FIG. 32A.
Figure 32C:
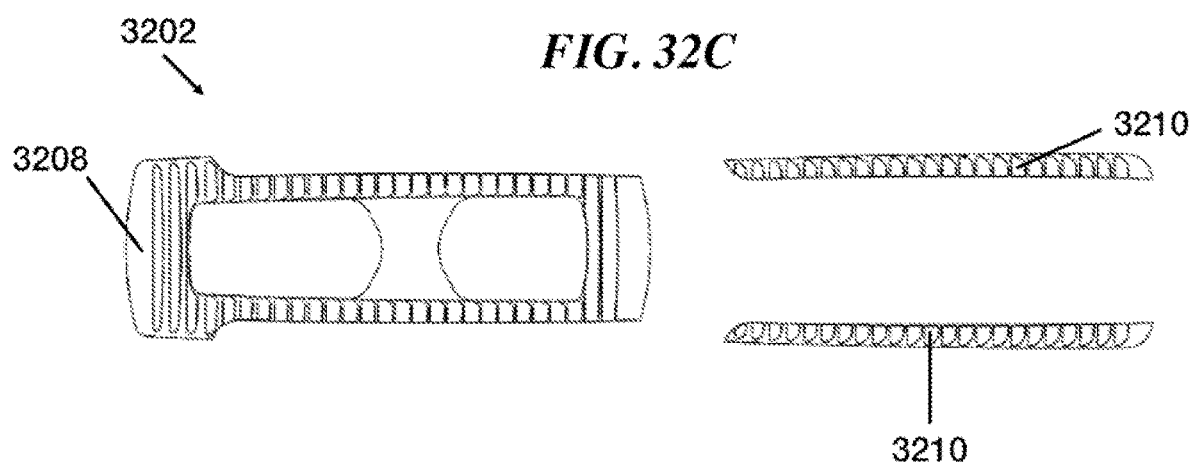
FIG. 32C is an exploded plan view of the thermal device of FIG. 32A.

FIGS. 32A-32C illustrate an exemplary thermal device 3202. The thermal device 3202 generally includes an implant 3204 (e.g., an interbody spacer, a disc replacement member, or an interbody fusion device) and a thermal probe 3206. The implant 3204 can include one or more thermally conductive portions or surface features to facilitate transfer of a heating or cooling effect from the thermal probe 3206 to the implant when the thermal probe is placed in contact with the implant. In the illustrated embodiment, the implant 3204 generally includes an interbody fusion spacer or cage 3208 sized and configured for insertion into a disc space via a lateral approach. The implant 3204 can include a generally rectangular parallelepiped frame. Superior and inferior surfaces of the implant 3204 can include teeth, spikes, or serrations to enhance purchase with the vertebral endplates when the implant is positioned in a disc space. At least one of the side surfaces of the implant 3204 can include a thermally conductive plate or exterior structural member 3210 coupled thereto or embedded therein. For example, the posterior-facing surface 3204P of the implant, which can be in closest proximity to the spinal canal when the implant is disposed in a disc space, can include or be covered with a thermally conductive plate. In the illustrated embodiment, both of the major sides 3204P, 3204A of the implant include a thermally conductive plate 3210 such that, regardless of the orientation in which the implant is inserted into the disc space, the major surface facing the spinal canal will include a thermally-conductive plate. The thermally-conductive plate 3210 can include one or more features for facilitating engagement with the thermal probe 3206. For example, the plate can include a recess 3212 in which at least a portion of the probe 3206 can be seated. The plate 3210 can also include a threaded opening or various other mating features for selectively coupling the plate to the probe 3206.

The frame 3208 of the implant can be formed from any of a variety of known materials suitable for interbody devices, including polymers such as PEEK. The thermally-conductive plate or plates 3210 can be formed from any of a variety of materials with high thermal conductivity, such as titanium. The plates 3210 can be load bearing (e.g., configured to bear physiological loads typically exerted on spinal discs).

The thermal probe 3206 can include a cavity formed therein through which heated or chilled fluid can be circulated to apply a thermal effect to an implant with which the probe is placed in contact. The probe 3206 can include inlet and outlet conduits configured to supply and withdraw fluid, respectively, from the cavity. For example, a multi-lumen conduit that includes an inlet lumen and an outlet lumen can be coupled to a proximal end of the probe and the distal end of the probe can be closed. Alternatively, or in addition, discrete inlet and outlet conduits can be coupled to the device.

In use, the implant 3204 can be inserted into a disc space defined between vertebral bodies of a patient's spine, for example using a lateral approach. The thermal probe 3206 can be placed in contact with or coupled to a thermally-conductive plate 3210 of the implant, either before or after the implant is inserted. Cooled or heated fluid can be circulated through the cavity of the thermal probe to apply a thermal effect to the implant and thereby apply localized thermal therapy to the anatomy proximate thereto (e.g., the spinal canal). After completion of the thermal therapy, or at any other desired time, the probe can be separated or decoupled from the implant and removed, leaving the implant in place indefinitely. Alternatively, the implant can be removed with the probe. As described in further detail below, the patient can be closed up with just the probe or just the inlet and outlet conduits extending through the closed incision, such that thermal therapy can be performed after the surgical procedure to implant the thermal device. Later, the probe can be decoupled from the device in a non-surgical or minimally-invasive procedure by simply pulling the probe through the closed incision.

Figure 33A:
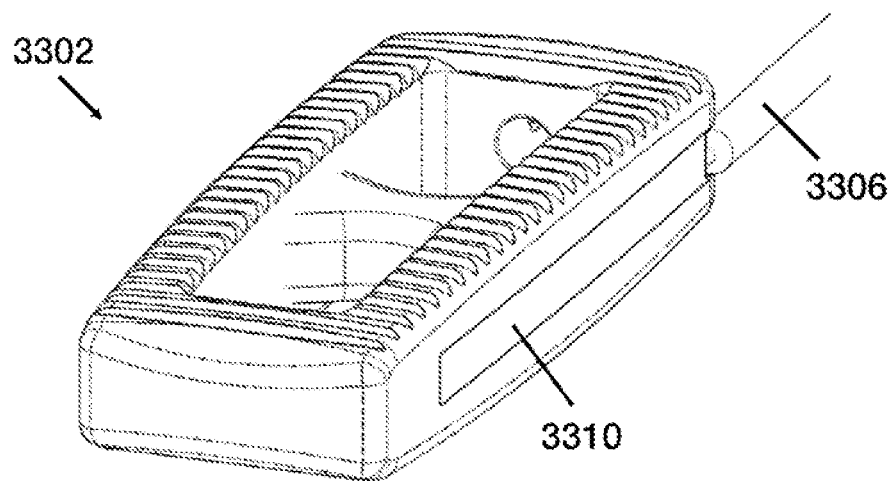
FIG. 33A is a perspective view of an interbody thermal device.
Figure 33B:
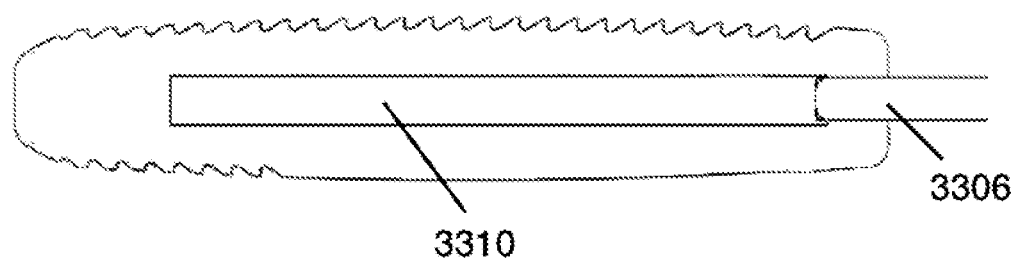
FIG. 33B is a profile view of the thermal device of FIG. 33A.

FIGS. 33A-33B illustrate an exemplary thermal device 3302. Except as indicated below, the structure and operation of the thermal device 3302 is substantially identical to the thermal device 3202, and therefore a detailed description is omitted here for the sake of brevity. In the thermal device 3302, the thermally-conductive member can be formed from an ultra-thermally efficient material such as graphene. For example, one or more side surfaces of the implant 3304 can include a strip 3310 of one-atom-thick graphene affixed thereto or seated therein. In use, the thermal probe 3306 can be placed in contact with the graphene strip 3310 to apply a thermal effect to the implant.

Figure 34A:
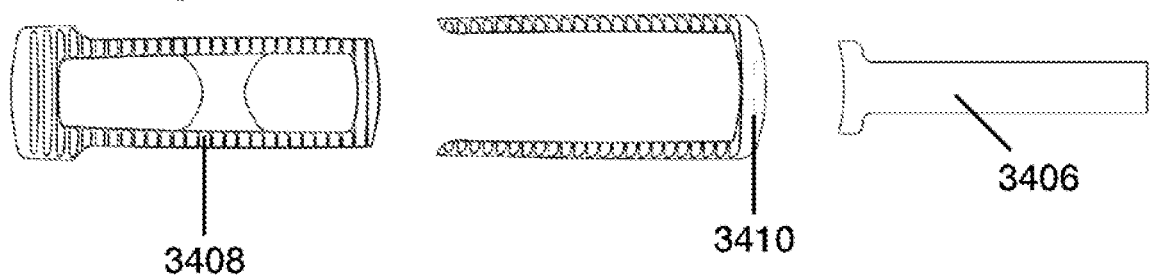
FIG. 34A is an exploded plan view of an interbody thermal device.
Figure 34B:
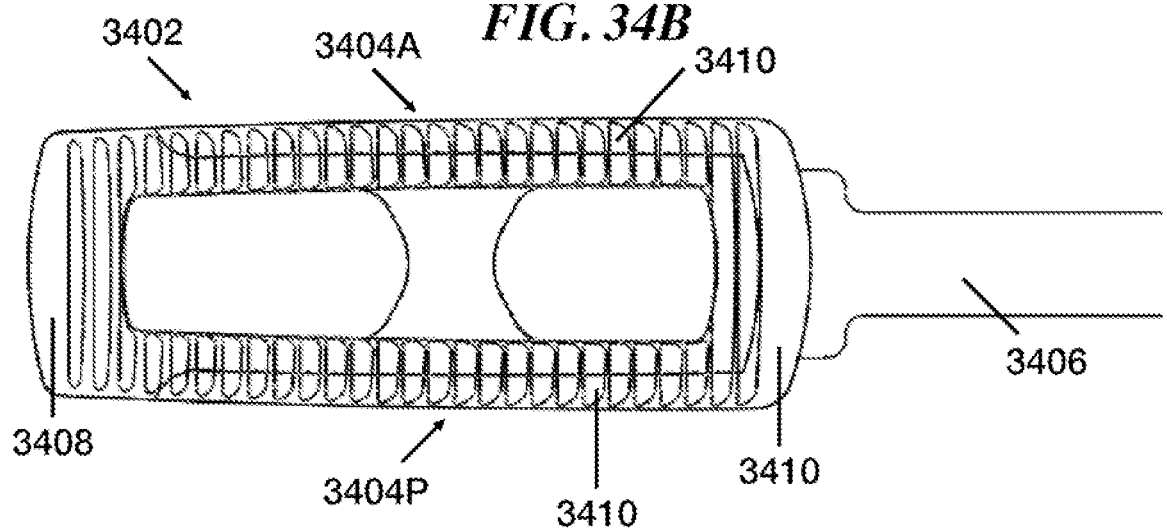
FIG. 34B is a plan view of the thermal device of FIG. 34A.
Figure 34C:
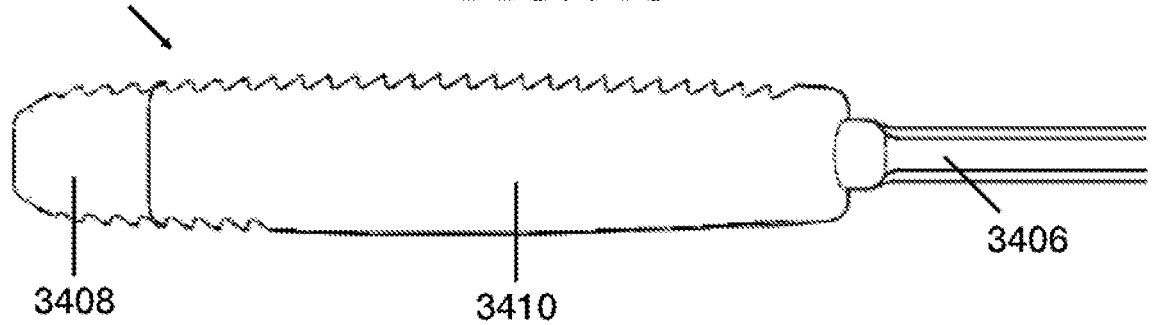
FIG. 34C is a profile view of the thermal device of FIG. 34A.

FIGS. 34A-34C illustrate an exemplary thermal device 3402. Except as indicated below, the structure and operation of the thermal device 3402 is substantially identical to the thermal device 3202, and therefore a detailed description is omitted here for the sake of brevity. In the thermal device 3402, the thermally-conductive plate 3410 can be C-shaped such that the plate extends around a posterior surface 3404P of the implant, an anterior surface 3404A of the implant, and a lateral surface of the implant. The thermal probe 3406 can be configured to contact or couple to the plate 3410 at any of a variety of locations, including on the lateral surface as shown. The thermal probe 3406 can serve as an insertion tool for guiding and urging the implant into the disc space. In use, the implant can be coupled to the thermal probe outside of the disc space and the thermal probe can be used to advance the implant into the disc space. A thermal effect can then be delivered to the implant via the thermal probe to apply localized thermal therapy to tissue in proximity to the implant (e.g., a patient's spinal canal in proximity to a plate portion of the implant).

Figure 35A:
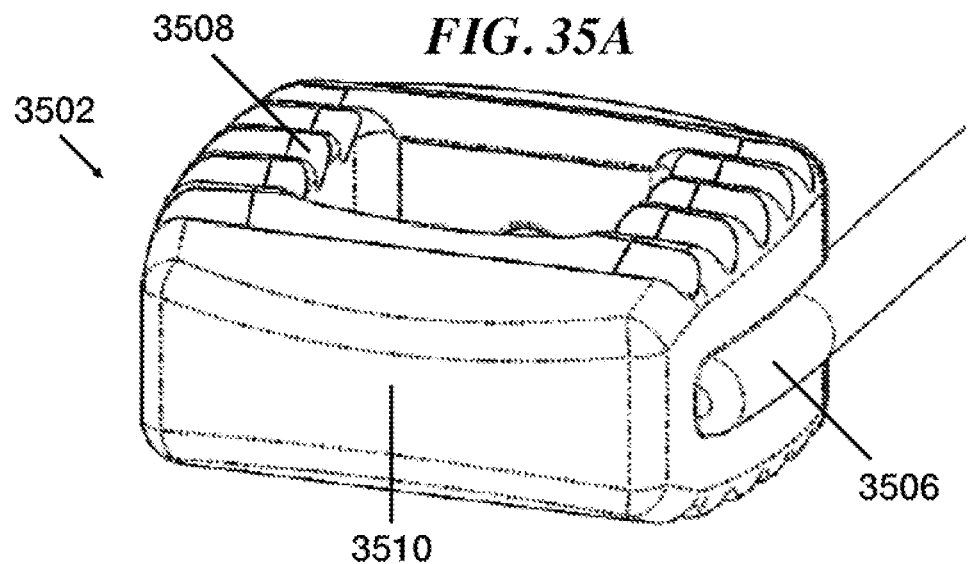
FIG. 35A is a perspective view of an interbody thermal device.
Figure 35B:
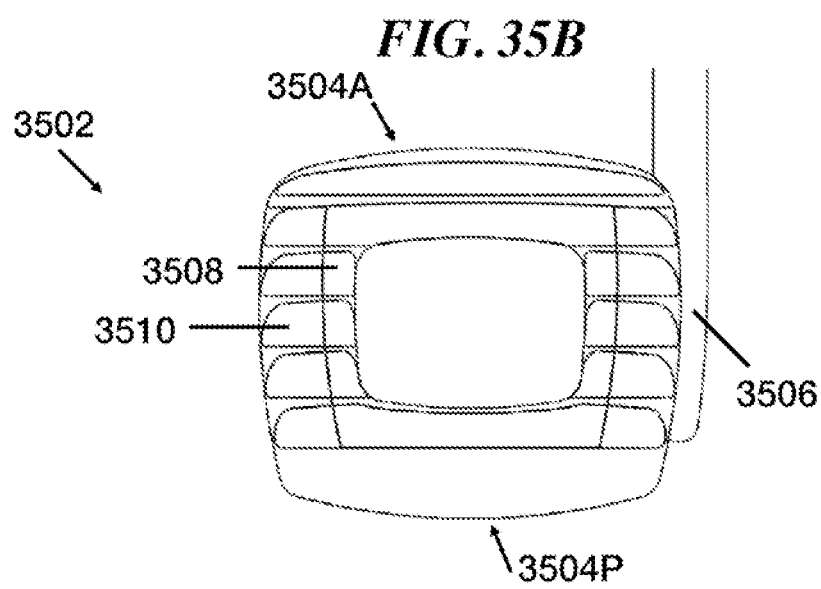
FIG. 35B is a plan view of the thermal device of FIG. 35A.
Figure 35C:
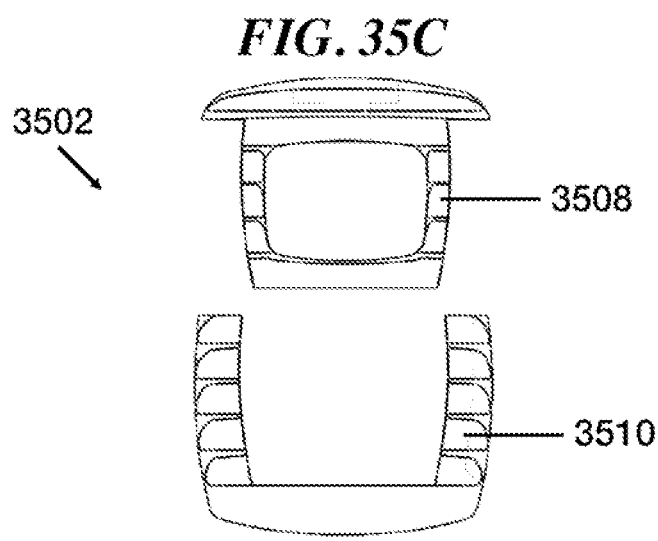
FIG. 35C is an exploded plan view of the thermal device of FIG. 35A.
Figure 36A:
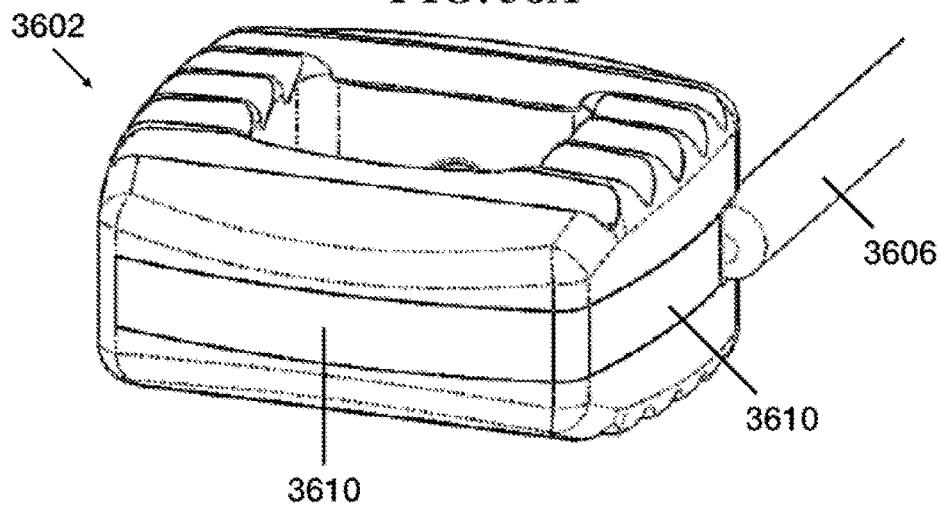
FIG. 36A is a perspective view of an interbody thermal device.
Figure 36B:
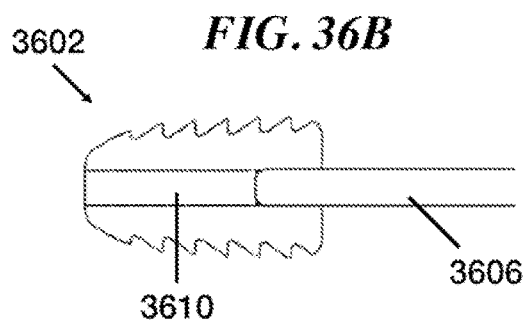
FIG. 36B is a profile view of the thermal device of FIG. 36A.
Figure 36C:
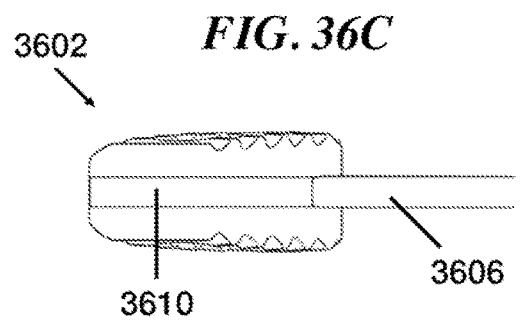
FIG. 36C is a profile view of the thermal device of FIG. 36A.
Figure 36D:
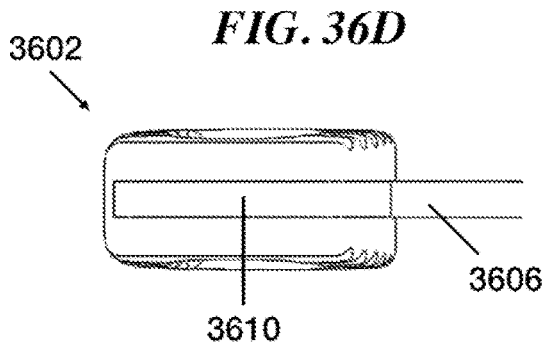
FIG. 36D is a profile view of the thermal device of FIG. 36A.
Figure 36E:
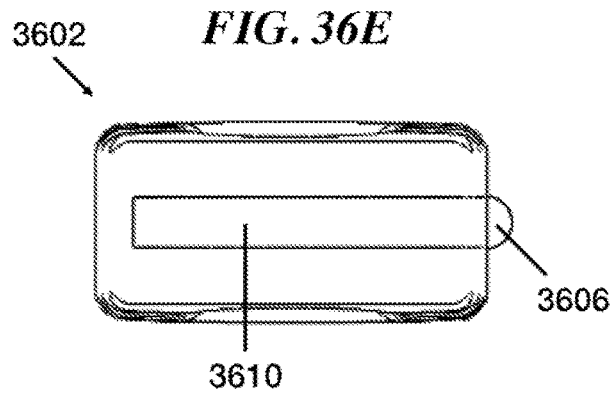
FIG. 36E is a profile view of the thermal device of FIG. 36A.

FIGS. 35A-35C illustrate an exemplary thermal device 3502. Except as indicated below, the structure and operation of the thermal device 3502 is substantially identical to the thermal device 3202, and therefore a detailed description is omitted here for the sake of brevity. In the thermal device 3502, the implant is sized and configured for delivery through an anterior approach, e.g., to perform an anterior cervical interbody fusion procedure. The device 3502 can include a thermally-conductive plate 3510 that extends around three sides of the implant (e.g., a posterior- or spinal-canal-facing side 3504P and first and second lateral sides). Accordingly, the thermal probe can be placed in contact with or coupled to either of the lateral sides of the thermally-conductive plate 3510 while the third side of the plate is disposed in contact with or in close proximity to the spinal canal to apply localized thermal therapy to the spinal canal.

FIGS. 36A-36E illustrate an exemplary thermal device 3602. Except as indicated below, the structure and operation of the thermal device 3602 is substantially identical to the thermal device 3502, and therefore a detailed description is omitted here for the sake of brevity. In the thermal device 3602, the thermally-conductive member can be formed from an ultra-thermally-efficient material such as graphene. For example, one or more side surfaces of the implant can include a strip 3610 of one-atom-thick graphene affixed thereto or seated therein. In use, the thermal probe 3606 can be placed in contact with the graphene strip to apply a thermal effect to the implant.

Figure 37A:
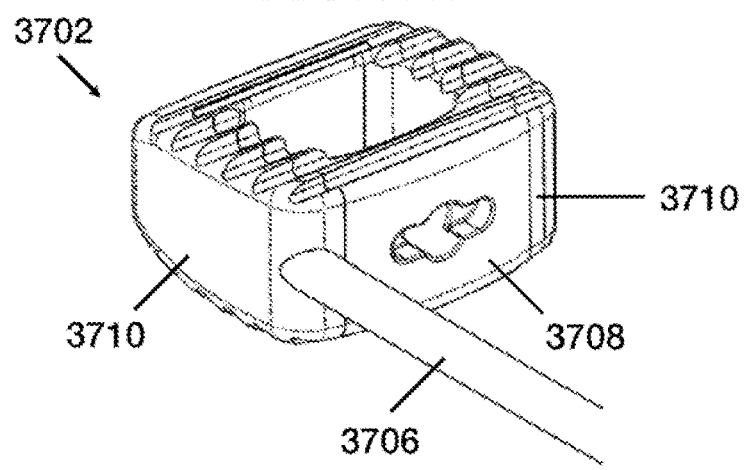
FIG. 37A is a perspective view of an interbody thermal device.
Figure 37B:
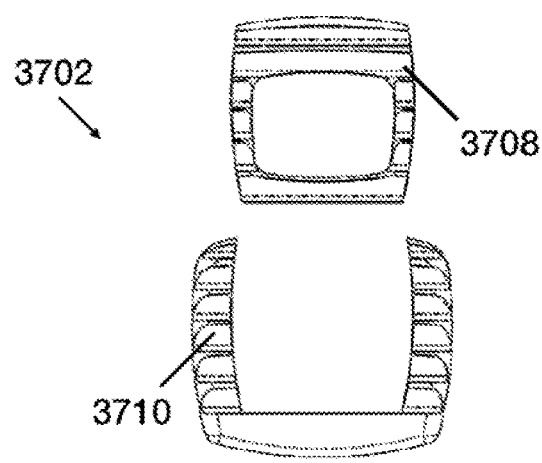
FIG. 37B is an exploded plan view of the thermal device of FIG. 37A.
Figure 37C:
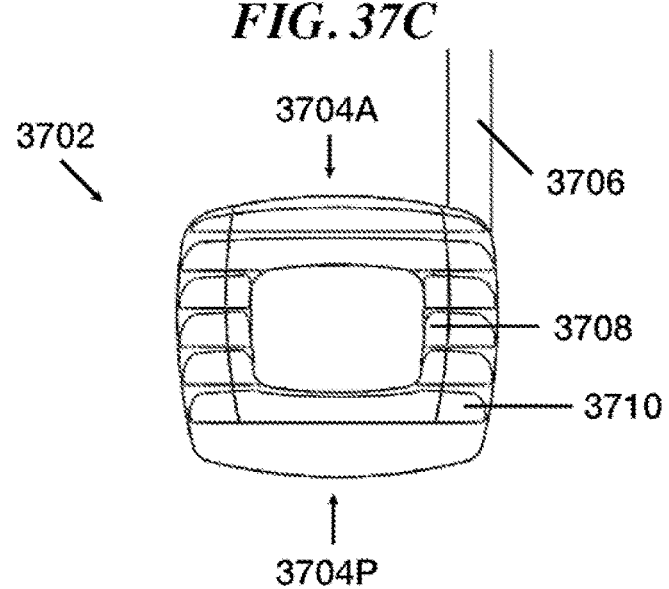
FIG. 37C is a plan view of the thermal device of FIG. 37A.

FIGS. 37A-37C illustrate an exemplary thermal device 3702. Except as indicated below, the structure and operation of the thermal device 3702 is substantially identical to the thermal device 3502, and therefore a detailed description is omitted here for the sake of brevity. In the thermal device 3702, the thermally-conductive plate 3710 extends around three sides of the implant (e.g., a posterior- or spinal-canal-facing side 3704P and first and second lateral sides) such that at least a portion of the plate is exposed to an anterior-facing surface 3704A of the implant. Accordingly, the thermal probe 3706 can be placed in contact with or coupled to either of the lateral sides of the thermally-conductive plate 3710 at a location along the anterior-facing surface 3704A of the implant, while the third side 3704P of the plate is disposed in contact with or in close proximity to the spinal canal to apply localized thermal therapy to the spinal canal.

FIGS. 38A-38C illustrate an exemplary thermal device 3802. Except as indicated below, the structure and operation of the thermal device 3802 is substantially identical to the thermal device 3502, and therefore a detailed description is omitted here for the sake of brevity. In the thermal device 3802, the thermally-conductive plate 3810 can be substantially rectangular or O-shaped such that it extends around four sides of the implant (e.g., a posterior or spinal-canal-facing side 3804P, an anterior side 3804A, and first and second lateral sides). The thermal probe 3806 can be configured to contact or couple to the plate 3810 at any of a variety of locations, including on the anterior surface 3804A as shown. The thermal probe 3806 can serve as an insertion tool for guiding and urging the implant into the disc space. In use, the implant can be coupled to the thermal probe outside of the disc space and the thermal probe can be used to advance the implant into the disc space. A thermal effect can then be delivered to the implant via the thermal probe to apply localized thermal therapy to tissue in proximity to the implant (e.g., a patient's spinal canal in proximity to a posterior surface 3804P of the plate portion 3810 of the implant).

Pad Thermal Devices

Figure 39A:
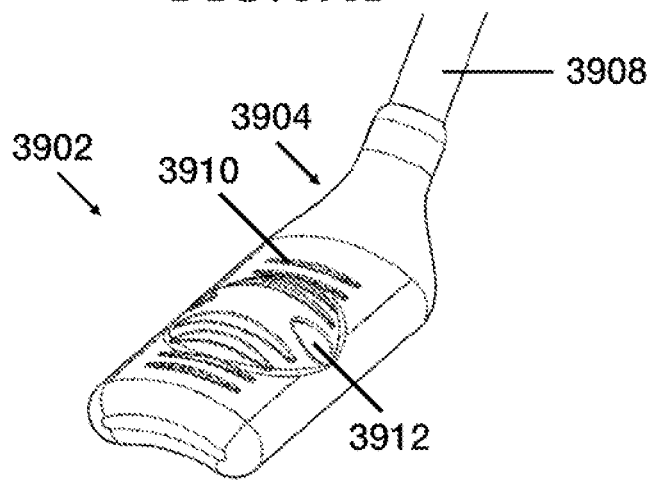
FIG. 39A is a perspective view of a pad thermal device.
Figure 39B:
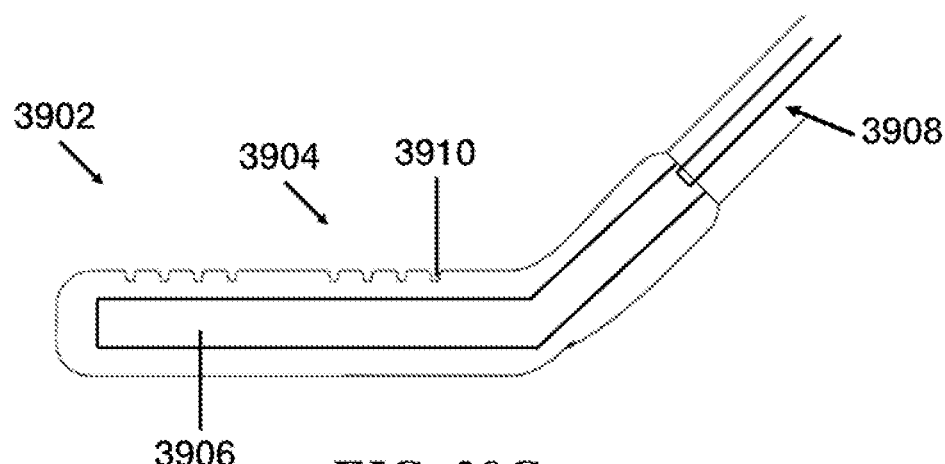
FIG. 39B is a sectional profile view of the thermal device of FIG. 39A.
Figure 39C:
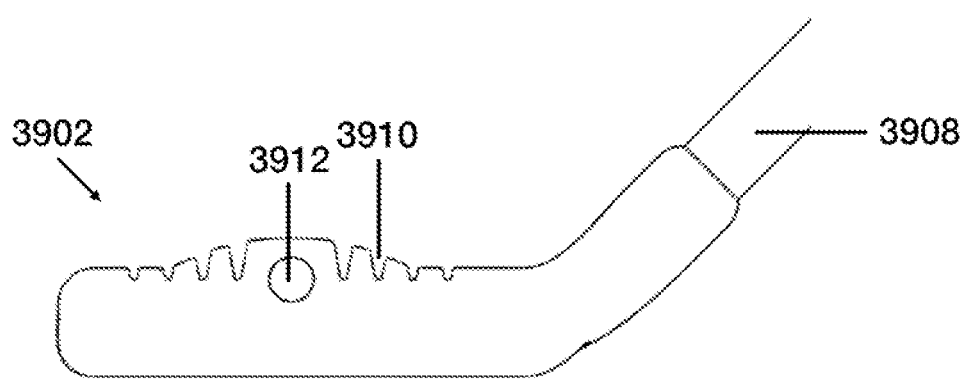
FIG. 39C is a profile view of the thermal device of FIG. 39A.
Figure 39D:
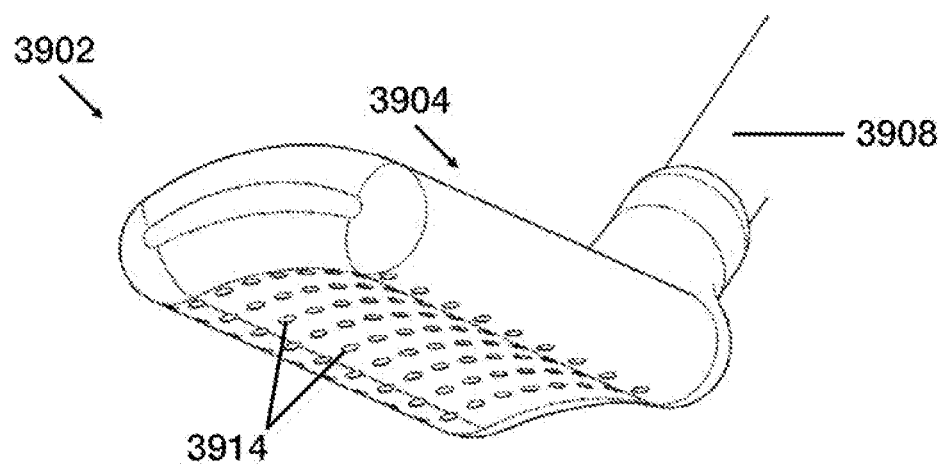
FIG. 39D is a perspective view of a pad thermal device.
Figure 39E:
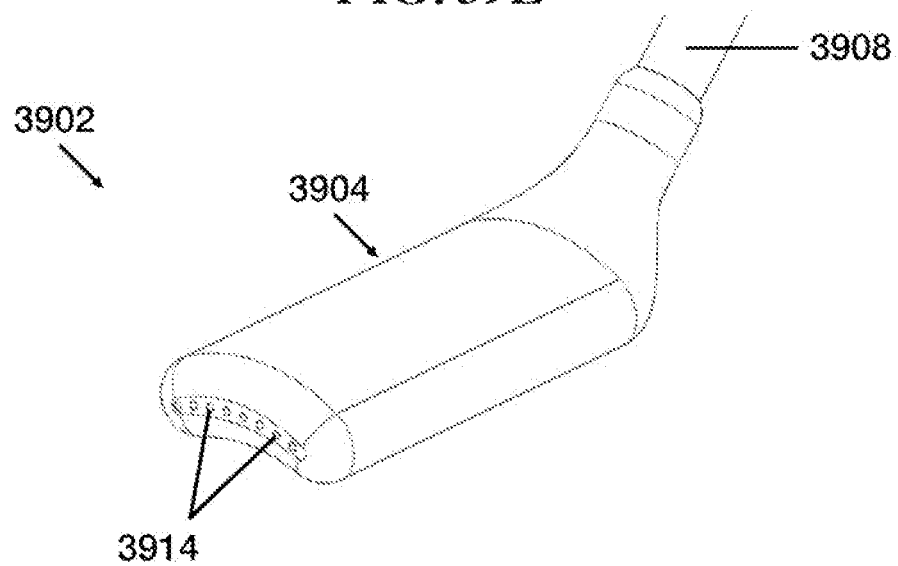
FIG. 39E is a perspective view of a pad thermal device.
Figure 39F:
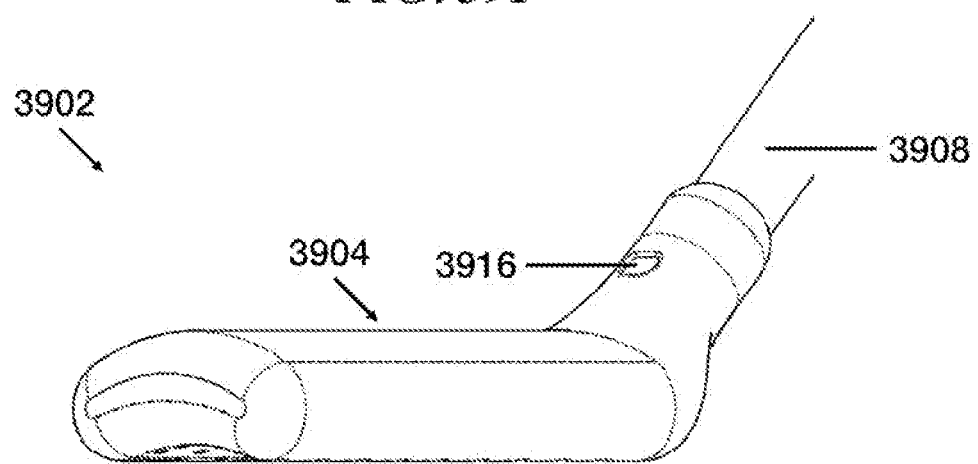
FIG. 39F is a perspective view of a pad thermal device.
Figure 39G:
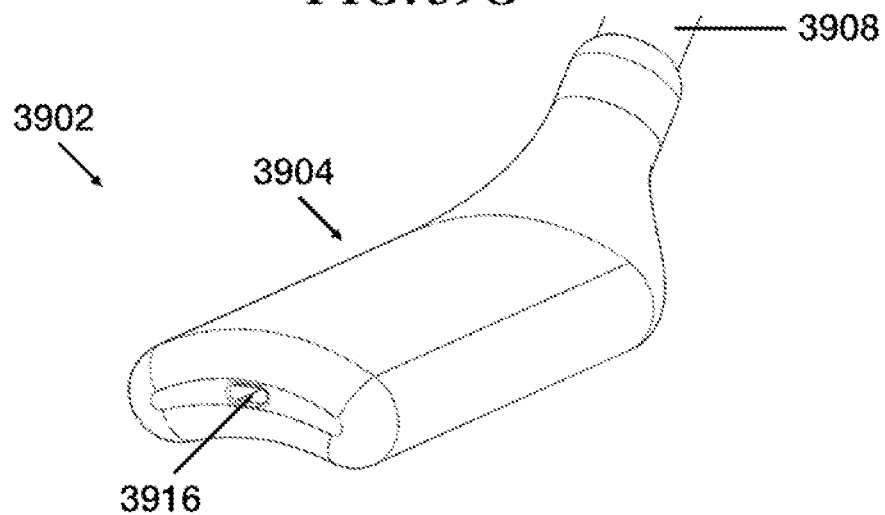
FIG. 39G is a perspective view of a pad thermal device.
Figure 39H:
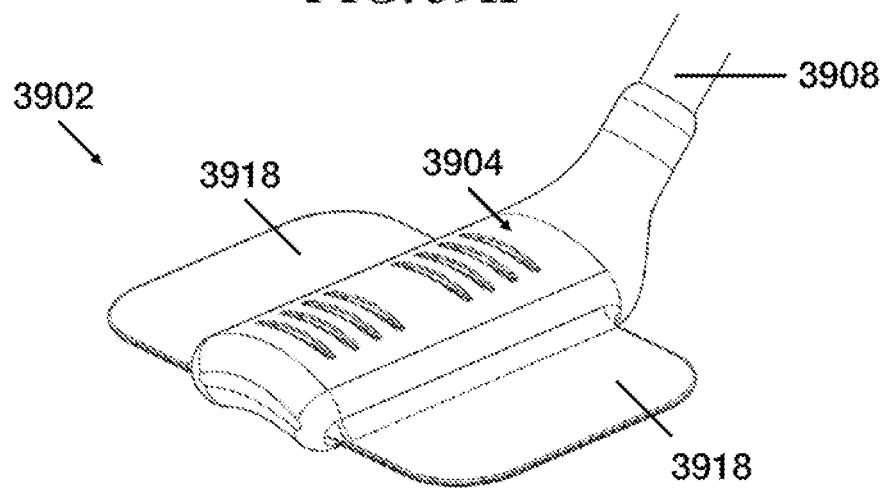
FIG. 39H is a perspective view of a pad thermal device.
Figure 39I:
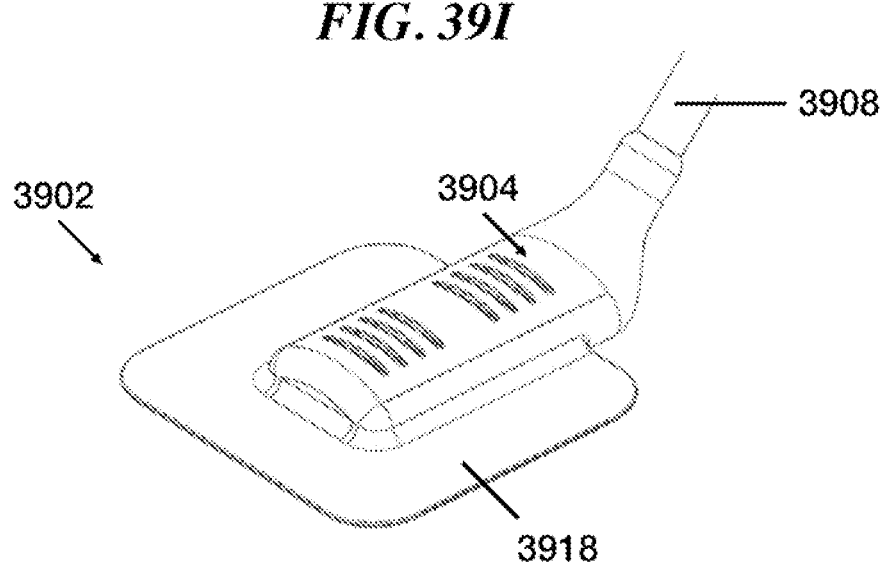

FIG. 39A illustrates an exemplary thermal device 3902. A number of variations on the device 3902 are shown in FIGS. 39B-39O. The device 3902 can be generally in the form pad 3904 that can be positioned adjacent to a target region of a patient to apply thermal therapy thereto. The pad 3904 can have substantially rectangular shape as shown or can have any of a variety of other shapes. In some embodiments, the pad can be sized and shaped based on the anatomy that is targeted for thermal therapy. For example, the pad can have a substantially flat, rectangular shape with rounded corners and convex bottom surface sized to conform to and fit over the exposed dura or spinal cord after a laminectomy. The pad can be positioned in contact with or in close proximity to the dura surrounding the spinal cord. The pad can be placed over the intact lamina between the transverse and spinous processes, or can be placed directly over the exposed dura or spinal cord after a laminectomy. The pad can also be placed over one or more spinal implants, such that the pad covers the implants and/or is in direct contact with or in close proximity to the implants. The convex bottom surface of the pad can be sized to receive at least a portion of the patient's spinal cord. It will be appreciated that the pad can have virtually any size or shape and that the size and shape can be selected based on various factors such as the anatomical location of the target site, the age, weight, species, or sex of the patient, the nature of the injury or condition suffered by the patient, and the types of procedures to be performed in conjunction with thermal therapy (e.g., laminectomy, vertebral fusion, and the like).

The pad 3904 can be rigid or can be resiliently or non-resiliently malleable or deformable such that the pad 3904 can be conformed to the anatomical structures to which it is applied. In particular, the pad 3904 can include a malleable membrane configured to form a substantial negative of the anatomy against which it is placed to maximize the contact surface area between the membrane and the anatomy.

The pad 3904 can be formed from any of a variety of materials. Exemplary materials include Silicone, Polyethylene terephthalate (PET), Nylon, Polyethylene (PE), Polyurethane, Polyvinyl chloride (PVC), Latex, Titanium, Steel, Gold, Cobalt Chrome, and combinations thereof.

The pad 3904 can include a cavity 3906 formed therein through which heated or chilled fluid can be circulated to apply a thermal effect to the device and to tissue proximate thereto. The device 3902 can include inlet and outlet conduits 3908 configured to supply and withdraw fluid, respectively, from the cavity. The conduits 3908 can be selectively detachable from the pad 3904 to facilitate post-surgical withdrawal of the conduits. A multi-lumen conduit 3908 that includes an inlet lumen and an outlet lumen can be coupled to a proximal end of the pad 3904 as shown. Alternatively, or in addition, discrete inlet and outlet conduits can be coupled to the pad. The conduits 3908 can be used as a tether, or the pad 3904 can include a separate dedicated tether, such that the tether can be manipulated from outside the patient to reposition, relocate, or remove the pad.

In use, the pad 3904 can be positioned over a target treatment site of a patient (e.g., an exposed dura of a patient's spinal canal). Cooled or heated fluid can be circulated through the cavity 3906 of the pad 3904 to apply localized thermal therapy to the target treatment site. After completion of the thermal therapy, or at any other desired time, the inlet and outlet conduits 3908 can be separated from the pad 3904 (e.g., by pulling the conduits proximally) and the pad 3904 can be left in place indefinitely. Alternatively, the pad 3904 can be removed with the inlet and outlet conduits 3908. As described in further detail below, the patient can be closed up with just the inlet and outlet conduits extending through the closed incision, such that thermal therapy can be performed after the surgical procedure to implant the thermal pad. Later, the fluid inlet and outlet conduits can be decoupled from the pad in a non-surgical or minimally-invasive procedure by simply pulling the conduits through the closed incision. Alternatively, the fluid inlet and outlet conduits and the pad itself can be removed together in a non-surgical or minimally-invasive procedure by simply pulling the conduits and the pad through the closed incision.

The thermal device 3902 can include one or more attachment features for coupling the thermal device to the patient's anatomy or to one or more ancillary devices (e.g., implants, stabilization hardware, and so forth). For example, as shown in FIG. 39B, the upper surface of the pad can include one or more grooves 3910 for retaining sutures such that the pad 3904 can be sutured down to the patient's anatomy. By way of further example, as shown in FIG. 39C, the pad 3904 can include an enclosed loop 3912 through which a suture can be threaded to suture the pad down to the patient anatomy.

In some embodiments, the pad 3904 can be configured to release at least a portion of the thermal fluid supplied thereto into the surrounding surgical site (e.g., via a controlled micro-drip). For example, as shown in FIG. 39D, the bottom surface of the pad 3904 can include one or more holes 3914 through which thermal fluid can slowly drip to bathe the target treatment site with the thermal fluid. The one or more holes 3914 can be arranged in a grid pattern or in any other pattern, and can be arranged to cover substantially the entire lower surface of the pad 3904. Alternatively, or in addition, as shown in FIG. 39E, the one or more holes 3914 can be formed in a distal-most or front-facing surface of the pad 3904 that is substantially perpendicular to the lower surface of the pad and that is opposite to an end of the pad to which the inlet and outlet conduits 3908 are coupled. The outlet conduit can be omitted in some embodiments, particularly those in which the thermal fluid is configured to be released from the pad through the one or more openings.

The pad 3904 can include one or more suction or vacuum ports 3916 in fluid communication with an aspiration conduit. In some embodiments, the aspiration conduit and the outlet conduit of the thermal device 3902 can be the same structure. In other embodiments, a dedicated aspiration conduit can be provided with the inlet and outlet conduits, either as a separate discrete conduit or as a dedicated lumen within a multi-lumen conduit 3908. The suction port 3916 and aspiration conduit can be configured to extract excess fluid from the surgical site at which the pad 3904 is placed. For example, thermal fluid introduced into the pad 3904 and released through the one or more openings 3914 can be collected and withdrawn from the patient using the aspiration conduit. The suction port 3916 and aspiration conduit can also be used with embodiments that do not release thermal fluid into the surgical site, for example to remove any extra fluid buildup that may naturally exist at the surgical site or be created as part of a surgical procedure ancillary to the delivery of thermal therapy. As shown in FIG. 39F, the suction port 3916 can be formed adjacent a proximal end of the pad 3904, at a junction between the pad and the conduit(s) 3908. Alternatively, or in addition, the pad 3904 can include a suction port 3916 formed adjacent a distal end thereof (e.g., in a distal-facing surface of the pad), as shown in FIG. 39G.

The pad 3904 can include various features to help secure the pad to the patient anatomy or hold the pad in a desired position with respect to the patient anatomy. For example, as shown in FIG. 39H, the pad 3904 can include first and second wings 3918 that extend laterally-outward therefrom. The wings 3918 can be fixed to the patient anatomy using surface tension or natural coagulation of blood present in the surgical site. Alternatively, or in addition, the wings 3918 can be attached to the patient anatomy using an adhesive (e.g., a temporary and minimum-strength adhesive gel). The wings 3918 can also include openings formed therein through which a suture or other fastener can be applied. As shown in FIG. 39I, the pad 3904 can include a unitary C-shaped wing 3918 that extends outward from the lateral sides of the pad and from the distal-facing surface of the pad. The wings 3918 can be formed from any of a variety of materials, including polymers, elastomers, etc.

Figure 39J:
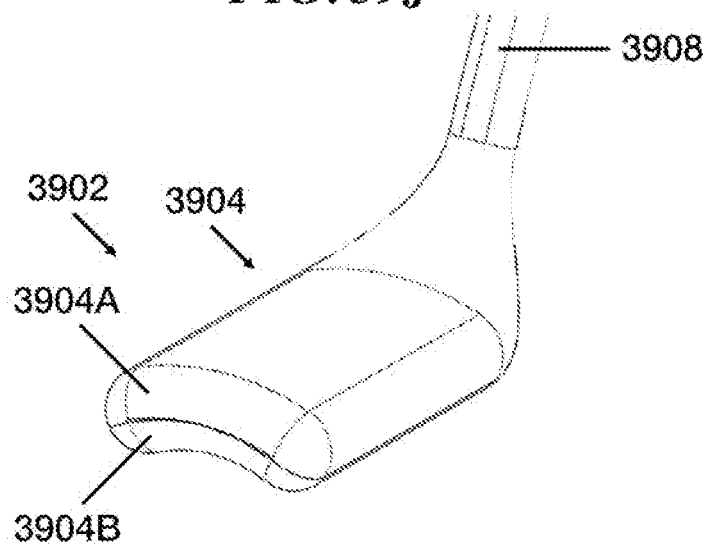
Figure 39K:
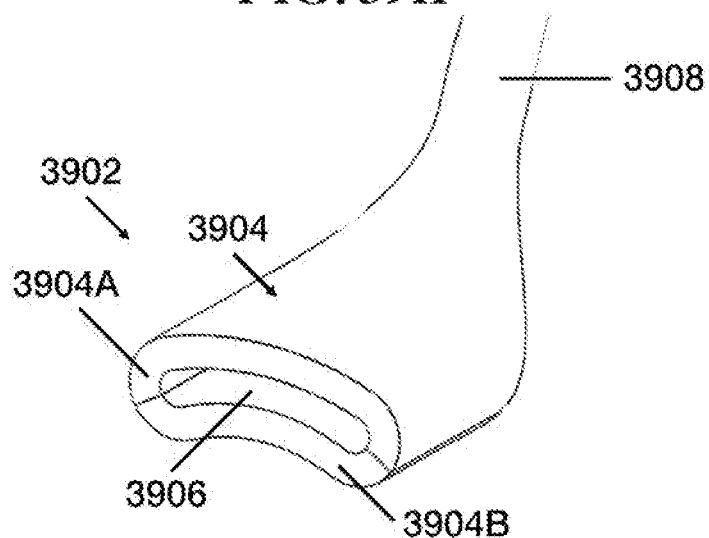
Figure 39L:
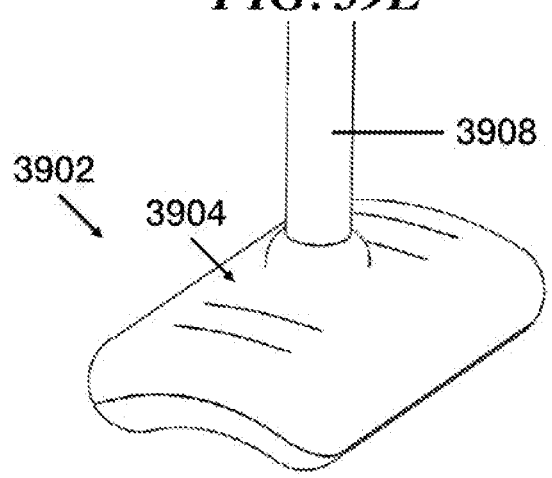
Figure 39M:
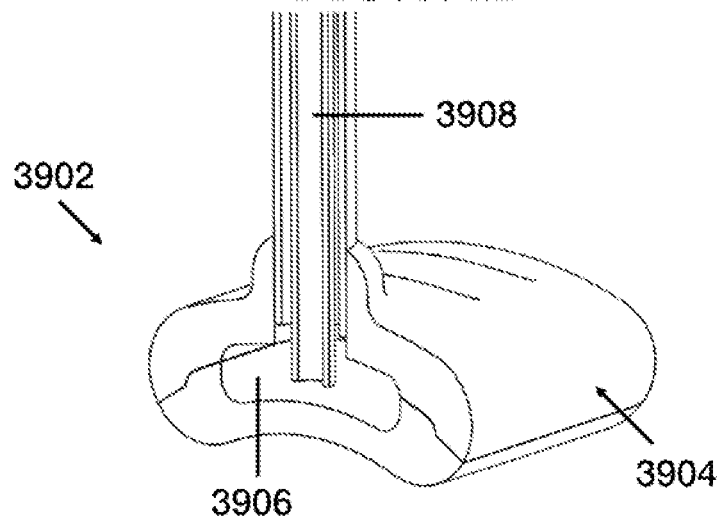
Figure 39N:
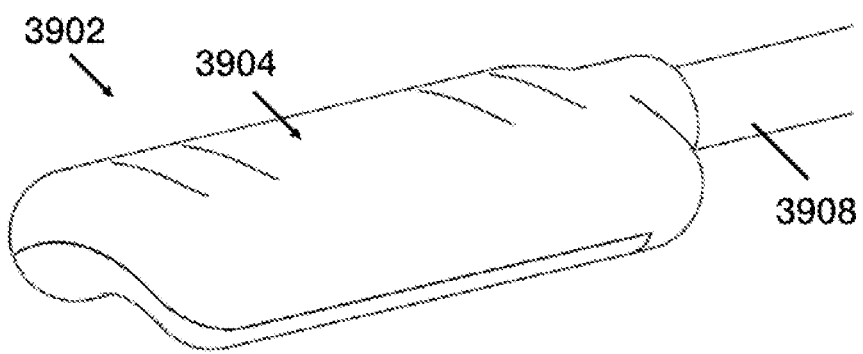
Figure 39O:
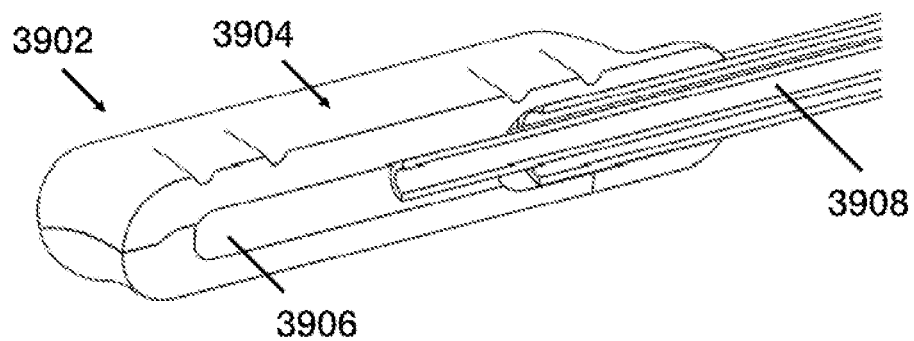

In some embodiments, as shown in FIGS. 39J and 39K, the pad 3904 can be formed from upper and lower shells 3904A, 3904B that define the cavity 3906 therebetween. The shells can be rigid or flexible. In some embodiments, the upper shell 3904A can be thermally-insulated and the lower shell 3904B can be thermally-conductive so as to focus the thermal effect towards the lower surface of the pad 3904 which is disposed adjacent the target anatomy. The fluid inlet and outlet conduits 3908 can be coupled to the pad 3904 at a proximal end thereof, or at any other location on the pad. For example, as shown in FIGS. 39L and 39M, the inlet and outlet conduits 3908 can be coupled to the pad 3904 substantially in the center of the upper surface of the pad. The inlet and outlet conduits 3908 can be concentric tubes as shown or can be discrete, non-concentric conduits.

The fluid inlet and outlet conduits 3908 can extend from the pad 3904 at an oblique angle or at any of a variety of other angles. For example, as shown in FIG. 39O, the inlet and outlet conduits 3908 can extend along an axis that is parallel to a longitudinal axis of the pad 3904.

Figure 40B:
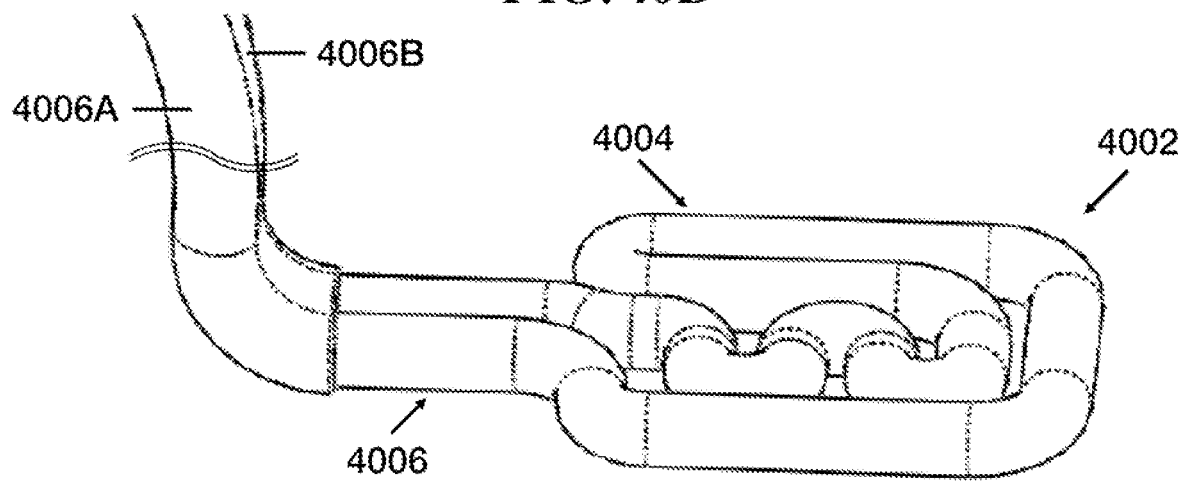
Figure 40C:
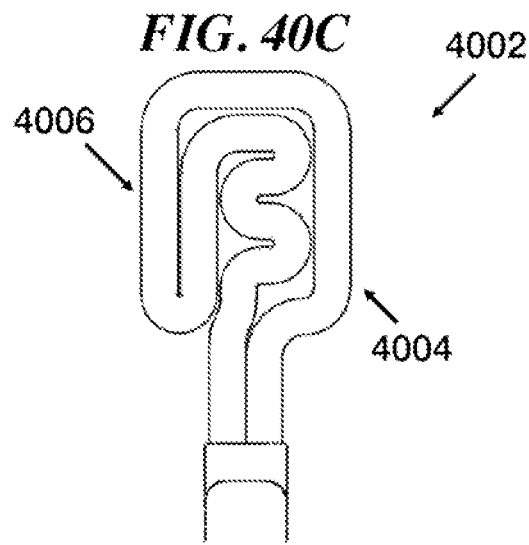

FIGS. 40A-40C illustrate an exemplary thermal device 4002. The device 4002 can be generally in the form pad 4004 that can be positioned adjacent to a target region of a patient to apply thermal therapy thereto. The pad 4004 can have substantially rectangular shape as shown or can have any of a variety of other shapes. In some embodiments, the pad can be sized and shaped based on the anatomy that is targeted for thermal therapy. The pad can be positioned in contact with or in close proximity to the dura surrounding the spinal cord. The pad can be placed over the intact lamina between the transverse and spinous processes, or can be placed directly over the exposed dura or spinal cord after a laminectomy. The pad can also be placed over one or more spinal implants, such that the pad covers the implants and/or is in direct contact with or in close proximity to the implants. It will be appreciated that the pad can have virtually any size or shape and that the size and shape can be selected based on various factors such as the anatomical location of the target site, the age, weight, species, or sex of the patient, the nature of the injury or condition suffered by the patient, and the types of procedures to be performed in conjunction with thermal therapy (e.g., laminectomy, vertebral fusion, and the like).

The pad 4004 can include a length of tubing 4006 and a substrate 4008. The tubing 4006 can be looped, coiled, snaked, wound, etc. to define the overall shape of the pad 4004. While a generally rectangular pad shape is shown, it will be appreciated that the tubing can be positioned in any of a variety of patterns to form any of a variety of shapes. In the illustrated embodiment, the tubing 4006 is looped such that two free ends 4006A, 4006B of the tubing extend proximally away from the substrate 4008 (e.g., through a substantially closed skin incision to a location exterior to the patient).

The substrate 4008 can be a planar sheet to which the tubing 4006 is adhered or otherwise coupled. The substrate 4008 can also be a three-dimensional form in which the tubing 4006 is suspended or encapsulated. The substrate 4008 can be formed from a biodegradable or bioabsorbable material that is configured to dissolve when the device 4002 is disposed in a surgical site within a patient after a predetermined time has elapsed. Exemplary materials from which the substrate 4008 can be formed include polymers such as poly-L lactic acid (PLLA), polyglycolic acid (PGA), polylactic acid (PLA), and combinations thereof. As the substrate 4008 dissolves, the tubing 4006 can become free to unwind or uncoil to facilitate removal of the tubing through a substantially closed skin incision. In other words, with the substrate 4008 no longer holding the tubing 4006 in the wound or coiled configuration, pulling the free ends 4006A, 4006B of the tubing proximally can cause the loop of tubing to straighten out into a single elongate loop that can be easily removed through a narrow passageway.

The tubing 4006 can define a fluid path through which heated or chilled fluid can be circulated to apply a thermal effect to the device 4002 and to tissue proximate thereto. The free ends 4006A, 4006B of the tubing 4006 can define inlet and outlet conduits configured to supply and withdraw fluid, respectively, from the looped or coiled portion of the tubing.

In use, the pad 4004 can be positioned over a target treatment site of a patient (e.g., an exposed dura of a patient's spinal canal). The substrate 4008 can be allowed to biodegrade or dissolve at the treatment site over a predetermined period of time. Cooled or heated fluid can be circulated through the tubing loop 4006 to apply localized thermal therapy to the target treatment site. After completion of the thermal therapy, or at any other desired time, for example after the substrate 4008 dissolves, the free ends 4006A, 4006B of the tubing loop can be pulled proximally to uncoil the loop of tubing and pull the tubing 4006 out of the patient. As described in further detail below, the patient can be closed up with just the free ends of the tubing extending through the closed incision, such that thermal therapy can be performed after the surgical procedure to implant the thermal device. Later, the device can be removed from the patient in a non-surgical or minimally-invasive procedure by simply pulling the loop of tubing through the closed incision.

FIGS. 41A-41C illustrate an exemplary thermal device 4102. Except as indicated below, the structure and operation of the thermal device 4102 is substantially identical to the thermal device 4002, and therefore a detailed description is omitted here for the sake of brevity. In the thermal device 4102, the length of tubing 4106 can include plural interior lumens. For example, the tubing 4106 can be formed from a co-extrusion that includes first and second interior lumens 4110, 4112 which can act as fluid inlet and fluid outlet lumens, respectively. The length of tubing 4106 can include a first proximal free end 4106A and a second distal free end 4106B. The distal free end 4106B of the tubing can be closed and can include a small cavity or crossover to place the distal end of the inlet lumen 4110 in fluid communication with the distal end of the outlet lumen 4112. The tubing 4106 can thus be looped or coiled such that only a single free end 4106A of the tubing extends proximally from the device (e.g., to a location outside of the patient). When the device 4102 is to be removed from the patient, only a single strand of the tubing 4106 needs to be pulled through the incision, thus allowing for a smaller profile than embodiments in which the tubing is looped as it is pulled through simultaneously.

Misc Device Features

As noted above, the thermal devices disclosed herein can include an inner reservoir or chamber. The chamber can house at least a portion of the elements, volumes, nozzles, fluid lumens, channels, paths, and so forth needed to support the cooling means. In implementations in which the cooling means includes expanding gas, the thermal device can include an expansion nozzle through which gas that has entered the thermal device via a cooling delivery conduit expands. The gas is expanded into the chamber, from which it can be exhausted from the thermal device via an exhaust conduit. The expanded gas can be exhausted into the environment, into a chamber or tank, or into a compressor which re-compresses it.

In implementations in which the cooling means is a chilled fluid, the fluid can be passed through the inner chamber of the thermal device to deliver a cooling effect thereto and to surrounding tissue. In some embodiments, the chamber can be in the form of a fluid lumen having a first end coupled to a delivery conduit and a second end coupled to an exhaust conduit. The chamber/fluid lumen can optionally be coiled, snaked, or formed in some other tortuous, surface-area maximizing shape such that heat exchange to/from fluid that is directed through the chamber can be optimized. The fluid can also simply enter the chamber through a delivery conduit, reverse direction, and exit the thermal device through an exhaust conduit.

In implementations in which the cooling means is a Peltier device, the Peltier device can be embedded inside the thermal device and electrical lines can be connected to the Peltier device internal to the thermal device. These electrical lines can extend from the thermal device to a power source and optionally a regulator of the cooling effect, which can regulate the voltage or current on the electrical lines. In some embodiments, the power source and/or regulator can be disposed on or in the thermal device or in a separate implantable unit.

The thermal device can optionally include a plurality of thermal fins formed within the chamber. For example, the thermal fins can extend radially inward from an outer wall of the chamber. In use, an expanded gas or chilled fluid can circulate around and across the thermal fins, which can improve the thermal conduction from the cooling means to the thermal device, and thus to the target tissue. The thermal fins can also improve the mechanical strength of the thermal device. It will be appreciated that the thermal fins can be oriented in a variety of directions and can take on a variety of shapes and sizes.

The delivery conduit can extend well into the chamber, terminating at a location adjacent to a distal end of the chamber. The exhaust conduit, on the other hand, can terminate only a small distance into the chamber, adjacent to the proximal end thereof. With this relative positioning of the conduit outlets, fluid introduced through the delivery conduit must flow through substantially the entire length of the chamber before being removed through the exhaust conduit. In this manner, the thermal transfer between the fluid and the thermal device can be maximized and more evenly distributed along the heat exchanging surfaces of the thermal device. In some embodiments, the chamber and/or the delivery conduit can extend only along discrete portions of the device where cooling is desired.

In some embodiments, the delivery conduit can be helically wound around the perimeter of the chamber. This can advantageously improve thermal transfer between the delivery conduit and the thermal device. In addition, the delivery conduit can act as an internal baffle, routing fluid released from the distal end of the delivery conduit along a helical path back towards the exhaust conduit. Thus, thermal transfer can also be improved between fluid released from the delivery conduit and the thermal device.

Portions of the thermal device other than the regions to be placed against the target anatomy can be coated with a thermally insulating material, such that the cooling effect is focused at the target site, such that surrounding tissue is protected from the cooling effect, and such that a surgeon or other user holding the device is protected from the cooling effect. Exemplary thermally insulating materials include silicone, which can be spray coated onto the device.

It will be appreciated that the devices and hardware described herein are able to be produced using common practices known to those skilled in the art of hardware manufacturing and specifically surgical device manufacturing.

Methods

The thermal devices disclosed herein can be used in any of a variety of associated methods. Various examples of such methods are described below. It should be noted that any ordering of method steps implied by the following is not to be construed as limiting the method to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present invention. Furthermore, two or more of the method steps can be performed simultaneously.

Before beginning a surgical procedure, a surgical plan can be developed, for example using pre-operative imaging of the site that is targeted for thermal therapy (e.g., cooling and/or heating). A thermal device having an appropriate type, size, shape, etc. can be selected as part of the surgical plan, or can be selected in real-time during the actual surgery. As detailed above, the particular thermal device to be used can be selected based on a variety of factors.

Access to the target site can be obtained using various known techniques. For example, a tissue opening can be formed using an open surgical technique (e.g., one in which skin, fat, muscle, connective tissue, etc. overlying the surgical site is incised and retracted). A tissue opening can also be formed using a minimally-invasive surgical technique (e.g., one in which a percutaneous access device is used to form a portal between the patient's skin surface and the target site).

Various steps can be performed to prepare the target site for thermal therapy. For example, in the case of a traumatic spinal cord injury, a decompression procedure (e.g., partial or complete laminectomy) can be performed at one or more vertebral levels. By way of further example, the site can be prepared by decorticating bone in the vicinity of the target site. Thus, in the case of a spinal procedure, the surfaces of the lamina, spinous process, and/or facets can be decorticated.

Various ancillary or related procedures can be performed at the target site before or after initiating thermal therapy. For example, a spinal fusion procedure or a procedure to install spinal stabilization hardware can be performed.

The steps involved in placing the thermal device and applying thermal therapy therewith vary depending on the type of thermal device that is used. Placement of the thermal device can include conforming the device to the target anatomy. Correct placement of the device can be verified visually or using fluoroscopy or other imaging techniques.

Thermal therapy can be applied through the device, for example by circulating a chilled fluid through the device. Embedded sensors can be used to monitor various parameters of the patient or operating environment, and the thermal therapy can be modulated based on the output of the sensors. For example, the temperature and/or flow rate of fluid circulated through the device can be adjusted to maintain a desired temperature. Where only intraoperative therapy is desired, the device can be removed once the desired duration of thermal therapy has been applied and the tissue opening can be closed. Where postoperative therapy is desired, the thermal device and one or more conduits can be left in place and the tissue opening can be closed. The one or more conduits can be left exposed, extending through the closed tissue opening. The one or more conduits can also be left buried beneath the patient's skin, where they are readily accessible in a minimally-invasive follow on procedure to conduct additional thermal therapy or to remove the one or more conduits. In either case, the conduits can be sutured or otherwise secured to prevent excessive movement. Postoperative thermal therapy can be delivered through the one or more conduits for an extended period, as described in more detail below. When the capability to deliver additional thermal therapy is no longer desired, the one or more conduits can be removed (e.g., by pulling them proximally to withdraw them from the patient). The thermal device can be left implanted permanently, and can optionally be configured to be bioabsorbed by the patient over time. Alternatively, the thermal device can be removed with the conduits or in a separate procedure.

FIG. 42 illustrates a method of applying thermal therapy to tissue. In step S4200, a tissue opening is formed. A thermal device is placed at a target site in step S4202 and the tissue opening is closed in step S4204. After closing the tissue opening, thermal therapy is delivered to the target site via the thermal device in step S4206. Thermal therapy can also be initiated or delivered via the thermal device prior to closing the tissue opening in step S4204, and can be continued or re-started in step S4206 after closing the tissue opening. FIG. 43 illustrates a method of applying thermal therapy to tissue. In step S4300, a target site is accessed. The target site is prepared in step S4302, and thermal therapy is applied to the target site via a thermal device in step S4304.

The thermal device can be left implanted for any amount of time (e.g., at least about 1 hour, at least about 4 hours, at least about 12 hours, at least about 18 hours, at least about 24 hours, at least about 48 hours, at least about 72 hours, at least about 5 days, at least about 7 days, at least about 2 weeks, at least about 1 month, at least about 3 months, at least about 6 months, at least about 1 year, at least about 5 years, at least about 10 years, and/or permanently or indefinitely.

Hypothermia Delivery—Temperature & Time

The methods and devices described herein can generally involve applying localized therapeutic hypothermia and, in some cases, cooling the tissue in and around the spinal cord. Various hypothermic instrumentations are described to deliver a cooling effect to the spinal canal, and to the spinal cord itself. "Therapeutic hypothermia" as used herein refers to the reduction of tissue temperature below a patient's normal body temperature, typically about 37 degrees C. Therapeutic hypothermia can also include reduction of tissue temperature below a patient's body temperature when treatment is initiated, which may not be the patient's normal body temperature (e.g., when the patient presents with a fever or in an already-hypothermic state, for example due to previous or ongoing systemic hypothermia treatment).

The degree of hypothermia applied can vary upon a number of factors. Target therapeutic temperatures can range from just below 0 degrees C. to just below normothermia. Tissue exposure to temperatures below 0 degrees C. can lead to cellular damage, however the bones of the spinal column are relatively resilient to such low temperatures and therefore target therapeutic temperatures can be below 0 degrees C. in some embodiments.

In an exemplary embodiment, the target tissue is cooled to within a range of about 0 degrees C. to about 37 degrees C. The target tissue can also be cooled to within a range of about 5 degrees C. to about 36 degrees C., more preferably about 15 degrees C. to about 36 degrees C., more preferably about 25 degrees C. to about 36 degrees C., more preferably about 25 degrees C. to about 35 degrees C., and more preferably about 30 degrees C. to about 34 degrees C. In certain embodiments, the target tissue can be cooled to about 36 degrees C., about 35 degrees C., about 34 degrees C., about 33 degrees C., about 32 degrees C., about 31 degrees C., or about 30 degrees C. In other aspects, the target tissue can be cooled to about 1 degree C. below normothermia, about 2 degrees C. below normothermia, about 5 degrees C. below normothermia, about 10 degrees C. below normothermia, or about 20 degrees C. below normothermia.

Degrees of hypothermia are sometimes described in terms of "mild" hypothermia (e.g., 0-5 degrees C. below normothermia), "moderate" hypothermia (e.g., 5-9 degrees C. below normothermia), "severe" hypothermia (e.g., 9-17 degrees C. below normothermia), and "profound" hypothermia (e.g., more than 17 degrees C. below normothermia). The methods disclosed herein can include cooling of tissue to within any of these ranges, and the systems and devices disclosed herein can be configured to achieve such cooling. Various treatment protocols can also be used in which the tissue temperature is cycled, pulsed, swept, ramped, and/or stepped through these or other ranges. For example, in one treatment method, the tissue temperature can be quickly lowered to a target temperature and then slowly ramped back up to normothermia when it is desired to cease treatment. By way of further example, the tissue temperature can be slowly stepped down to a first target temperature, oscillated between the first target temperature and a second target temperature, and then eventually stepped back up to normothermia.

The duration of exposure of the target tissue to the cooling effect can range from minutes to days, weeks, months, or years depending on a variety of factors, including the patient's condition, the treatment of the patient's other injuries, the prospective treatment protocol for the patient, and monitored or detectable physiological responses, or lack thereof, to the cooling. Therapeutic hypothermia can be applied in a single procedure or multiple times. In either case, a multiplicity of different temperatures can be applied. Preferably, when discussing target temperatures, it is intended to mean the desired therapeutic temperature of the targeted tissue. Alternatively, target temperature at times can also refer to the temperature of the thermal device or the cooling chamber or element of the thermal device. It will be appreciated that it can be necessary in some instances to cool the thermal device to below the target tissue temperature in order for the target tissue to reach the target tissue temperature.

The methods described herein can include cooling the spinal canal tissue and the spinal cord for variable lengths of time and/or at different temperatures. In addition, cooling can occur in multiple doses, where each dose can differ from the others in exposure time and/or temperature. The determination of the exposure time(s) and temperature(s) can be predetermined based on known effective times and temperatures or can be determined based on the condition of the patient and/or when the treatment is applied relative to when the injury occurred. A wide variety of physiological effects, both local and systemic, can arise from the cooling of the target tissue (e.g., spinal canal tissue and the spinal cord) below normal body temperature. Exposure time, doses, and target temperature can be varied during the procedure based on monitored physiological parameters or characteristics as well as parameters of the cooling devices or systems.

These parameters include, but are not limited to, neurological findings, blood pressure, target-tissue temperature, specific tissue temperature (proximate to target tissue), core (rectal) body temperature, venous blood temperature near or exiting target tissue, pulmonary conditions, cardiac conditions, sensory evoked potentials (SEPs, including somatosensory evoked potentials), motor-evoked potentials (MEPs), intrathecal pressure, perfusion pressure, levels of blood oxygen & glucose, ATP concentrations, markers of excitotoxicity, vasogenic edema, apoptosis, inflammation, and enzymatic responses. The target temperature, doses, and exposure time can be selected by initial measurements of these physiological parameters and then modified based upon real-time measurement of these parameters. Effectively, the cooling regimen, in terms of temperatures, exposure times, and doses, can be controlled by measured physiological characteristics of the patient and the cooling devices and systems.

For example, a cooling effect can be applied initially at a predetermined target temperature based on the type and severity of injury incurred, including for example the vertebral level of injury. The cooling effect can be increased, and as such, the target temperature can be reduced, if after a predetermined period of time, the motor-evoked potential responses of the patient appear unremarkable. In one embodiment, if the difference between the arterial blood pressure and the cerebral spinal fluid pressure reduces below a predetermined threshold, the application of the therapeutic hypothermia can be stopped. It should be understood that there are any number of protocols that can be followed in the application of therapeutic hypothermia based on clinical, laboratory, and monitoring markers.

In some embodiments, therapeutic hypothermia is initiated as soon as possible following a spinal injury, e.g., less than 8 hours after the injury. Therapeutic hypothermia can be maintained up to 72 hours, up to 120 hours, or more. It can be desirable to deliver therapeutic hypothermia for a much shorter duration as well, including as little as a fraction of an hour (e.g., 5 minutes, 15 minutes, 30 minutes, or 45 minutes).

The use of therapeutic hypothermia on the spinal cord and the spinal canal can yield a variety of beneficial effects. Such effects can include the reduction of nervous tissue metabolic demand, excitotoxic markers, apoptosis, free-radicals, and inflammation. It should be noted that some of the mechanisms of action associated with therapeutic hypothermia are not fully understood, but experience with its application in a variety of clinical situations suggests a mitigating effect in spinal cord damage from trauma, vascular insult, or surgical insult.

Transosseous Cooling

In some of the methods and devices described herein, a cooling effect is applied transosseously, or through bone. In particular, tissue can be cooled by positioning a thermal device in or over adjacent or nearby bone or over an implant implanted in adjacent or nearby bone. Bone has properties that make it an advantageous cooling platform. Boney structures are readily locatable due to their greater density and rigidity than so-called soft tissues. Furthermore, their geometries are readily mapped radiographically, are relatively consistent between patients, and have easily locatable features or landmarks. Accordingly, particular surrounding or soft tissues are relatively consistently located in a known proximity to these bone structures and landmarks. In particular, vertebral pedicles and lamina lie in close proximity to the contents of the spinal canal, including the spinal cord and nerve roots.

These attributes allow specific surrounding soft tissue to be reliably targeted by using adjacently located bone structures and landmarks of the bone structures as a platform and avenue to put devices near the specific soft tissue. Using bony structures and their landmarks as a means for targeting nearby or adjacent tissues helps avoid a need to directly target the tissue wishing to be treated, leaving the tissue undisturbed.

An advantageous aspect of a transosseous approach for providing a cooling effect to nearby soft tissue is the fact that bone is rigid, allowing for an device to be securely anchored into or on the bone, where the bone is not subject to deformation because of bodily movement or because of the device's presence. The rigid nature of the bone also allows a thermal device applied or anchored thereto without disturbing the tissues outside of the bone.

A transosseous approach for providing a cooling effect to nearby soft tissue allows for the implantation of thermal instrumentation without disturbing the soft tissue itself. That is, by using a bone approach and cooling across the bone wall to the nearby tissue, the targeted nearby tissue is not physically touched, displaced, or incised by the thermal device or by the surgical steps needed to implant the thermal device. Certain tissues, such as spinal cord tissue, are delicate and sensitive to disturbances, and such disturbances could cause permanent injury to the tissues. As such, it can be undesirable to implant thermal devices in these tissues or in nearby soft tissues due to risks of causing injury to the tissues. Bone is very resilient to such disturbances, and typically does not realize a great loss in function or strength and is typically not susceptible to long term injury from such disturbances. It is therefore desirable to apply or affix a thermal device to a bony structure and cool nearby soft tissue transosseously, or across the bone wall, thus allowing for reliable cooling access to soft tissue without physically disturbing the soft tissue itself.

In exemplary embodiments, the soft tissue that is targeted to be cooled is the spinal cord, other spinal canal tissue, and/or nerve root tissue, and the bony structures which act as the cooling platform are parts of a vertebra, including the elements of the posterior arch such as the pedicles, the lamina, and the spinous process. A transosseous approach for providing cooling across pedicle and/or lamina bone to the adjacent spinal canal contents targets the spinal cord without its actual contact, displacement, or penetration. This can be a critical consideration since the spinal cord's tolerance for such intrusions is likely minimal. In some embodiments, however, particularly those in which a decompression procedure is performed, the thermal devices can be placed in direct contact with the spinal cord or the dura.

Concluding Statements

It will be understood that any of the methods and devices disclosed herein can be used on multiple vertebrae at once and/or multiple bony structures of each vertebra at once, by utilizing multiple thermal devices at the same time or a single, larger thermal device. It will be understood that the methods and devices disclosed herein can be used for conditions other than traumatic spinal cord injury, including for cooling other tissues. The methods and devices can be used for other types of spinal cord injury, as well as for treating nerve root damage. The methods and devices can be used prophylactically. The methods and devices can be used before, during, and/or after an injury occurs and can be used pre-operatively, peri-operatively, intra-operatively and/or post-operatively with regard to any particular procedure that can be conducted.

Furthermore, the methods and devices can be used for non-injury related purposes. In particular, the methods and devices described herein can be used as an adjunctive procedure to an aneurysm repair surgery, such as thoracoabdominal aortic aneurysm repair or abdominal aortic aneurysm repair. In these procedures, it is common for blood flow to the spinal cord to be compromised, thus introducing a risk of ischemic spinal cord injury. The methods and devices described herein can provide a protective therapy during such ischemic periods.

Further, the methods and devices described herein can also be used for spinal fusion procedures where cooling is not initially intended. The methods and devices described herein can be used for fusion with the understanding that an intraoperative complication can occur (example: iatrogenic injury caused during scoliosis correction surgery) where having the capability to deliver a cooling effect can be desired.

The methods and devices described herein can be used prophylactically to deliver a cooling effect to nerve roots. Though such delivery of a cooling effect can be achieved with one thermal device, it can be better achieved by having two or more thermal devices placed above and below the particular root that is being targeted. The delivery of a cooling effect to a nerve root can also occur peri-operatively or post-operatively.

It will be appreciated that the methods and devices disclosed herein can be used in other parts of a mammalian body, and in particular, can be used with orthopedic procedures to deliver a cooling effect to surrounding tissues.

The described aspects above are given as illustrative examples of those that fall within the scope of the subject matter described, but are not intended to limit that scope. The described devices and methods can be the sole devices and methods used and performed in the spine at the time of the herein described therapy or can accompany other devices and procedures such as those related to spinal decompression, reduction, stabilization, and fusion.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used device is obtained and if necessary cleaned. The device can then be sterilized. In one sterilization technique, the device is placed in a closed and sealed container, such as a plastic or TYVEK bag. The container and its contents are then placed in a field of radiation that can penetrate the container, such as gamma radiation, x-rays, or high-energy electrons. The radiation kills bacteria on the device and in the container. The sterilized device can then be stored in the sterile container. The sealed container keeps the device sterile until it is opened in the medical facility.

Further details on methods and devices for cooling tissue, including methods and devices which can be used in conjunction with those described herein, are discussed in U.S. Pat. No. 8,523,930 issued on Sep. 3, 2013, entitled "METHODS AND DEVICES FOR COOLING SPINAL TISSUE"; U.S. Pat. No. 8,721,642 issued on May 13, 2014, entitled "TISSUE COOLING CLAMPS AND RELATED METHODS"; and U.S. application Ser. No. 14/276,265 filed on May 13, 2014, entitled "IMPLANTABLE DEVICES FOR THERMAL THERAPY AND RELATED METHODS"; which are each hereby incorporated by reference herein in their entirety.

The foregoing description has been presented for purposes of illustration and description. Many modifications and variations of the subject matter described will be apparent to those skilled in the art. Although the invention has been described by reference to specific embodiments, it should be understood that numerous changes can be made within the spirit and scope of the inventive concepts described. Accordingly, it is intended that the invention not be limited to the described embodiments, but that it have the full scope defined by the language of the following claims.

The invention claimed is:

1. A method of applying localized thermal therapy to a patient, the method comprising:
   implanting a bone anchor into a bone structure of the patient, wherein the bone anchor includes a surface with a docking hole for a connector and the surface also includes a fluid inlet port and a fluid outlet port;
   attaching the connector having a fluid delivery conduit and a fluid exhaust conduit to the bone anchor to place the fluid delivery conduit in fluid communication with the fluid inlet port and the fluid exhaust conduit in fluid communication with the fluid outlet port; and
   circulating a cooled fluid through the bone anchor via the connector such that the fluid enters the bone anchor through the fluid delivery conduit and exits the bone anchor through the fluid exhaust conduit to apply a thermal effect to the bone anchor, the bone structure of the patient, and tissue adjacent to the bone structure of the patient.

2. The method of claim 1, wherein attaching the connector comprises attaching the connector to a head portion of the bone anchor such that a distal-facing surface of the connector abuts a proximal facing surface of the head portion of the bone anchor.

3. The method of claim 1, wherein circulating the cooled fluid through the bone anchor comprises circulating the fluid through a proximal head portion of the bone anchor.

4. The method of claim 1, further comprising closing a skin incision through which the bone anchor is implanted in the patient such that the fluid delivery conduit and the fluid exhaust conduit extend through the incision and, thereafter, circulating the fluid.

5. The method of claim 4, further comprising closing the incisions and, thereafter, detaching the connector from the bone anchor and removing the connector from the patient without re-opening the incision.

6. The method of claim 2, wherein the proximal surface of the bone anchor post includes the surface that contains the fluid inlet port and the fluid outlet port.

7. The method of claim 1, wherein the docking hole includes a first docking hole and a second docking hole to engage respective lateral posts of the connector.

8. A method of applying localized thermal therapy to a patient, the method comprising:
   implanting a bone anchor with a pre-assembled fluid conduit connector into a bone structure of the patient, wherein the bone anchor includes a surface with a docking hole for the connector, the connector includes a fluid delivery conduit and a fluid exhaust conduit, and the surface includes a fluid inlet port and a fluid outer port in fluid communication with the fluid delivery conduit and the fluid exhaust conduit; and
   circulating a cooled fluid through the bone anchor via the connector such that the fluid enters the bone anchor through the fluid delivery conduit and exits the bone anchor through the fluid exhaust conduit to apply a thermal effect to the bone anchor, the bone structure of the patient, and tissue adjacent to the bone structure of the patient.

9. The method of claim 8, wherein a surgical incision is closed around the fluid delivery and exhaust conduits that extend from the connector to a cooling system, and thermal therapy is applied.

10. The method of claim 9, wherein the connector and fluid delivery and exhaust conduits are removed from the bone anchor without re-opening the incision.

11. The method of claim 8, wherein after thermal therapy is completed, the connector is removed from the bone anchor and the bone anchor remains implanted.

* * * * *